United States Patent
Yin et al.

[11] Patent Number: 5,919,442
[45] Date of Patent: Jul. 6, 1999

[54] HYPER COMB-BRANCHED POLYMER CONJUGATES

[75] Inventors: Rui Yin; Donald A. Tomalia; David M. Hedstrand; Douglas R. Swanson, all of Midland; James R. Baker, Jr.; Jolanta F. Kukowska-Latallo, both of Ann Arbor, all of Mich.

[73] Assignees: Dendritech, Inc., Midland; University of Michigan, Ann Arbor, both of Mich.

[21] Appl. No.: 08/694,787

[22] Filed: Aug. 9, 1996

Related U.S. Application Data

[60] Provisional application No. 60/002,202, Aug. 11, 1995, provisional application No. 60/002,833, Aug. 25, 1995, provisional application No. 60/003,105, Sep. 1, 1995, and provisional application No. 60/004,108, Sep. 21, 1995.

[51] Int. Cl.$^6$ .......................... A61K 31/74; A01N 25/10
[52] U.S. Cl. .................................. 424/78.18; 424/78.19; 424/84; 424/85.1; 424/85.8; 424/78.01; 424/1.11; 424/1.33; 424/1.37; 424/9.1; 424/178.1; 424/184.1; 424/193.1; 424/280.1; 424/405; 424/406; 424/422; 424/486; 424/487; 424/DIG. 16; 514/772; 525/417; 525/539; 525/902

[58] Field of Search ...................... 424/401, 405, 424/406, 422, 486, 487, 84, 85.1, 85.8, DIG. 16, 78.01, 78.02, 78.08, 1.11, 1.33, 1.37, 9.1, 178.1, 184.1, 280.1, 193, 78.17–78.19; 523/105, 122; 525/410, 417, 539, 902, 279, 280; 514/772

[56] References Cited

U.S. PATENT DOCUMENTS

| | | | |
|---|---|---|---|
| 3,251,664 | 5/1966 | Dickson et al. | 44/66 |
| 4,558,120 | 12/1985 | Tomalia et al. | 528/363 |
| 4,599,400 | 7/1986 | Tomalia et al. | 528/405 |
| 5,527,524 | 6/1996 | Tomaus et al. | 424/1.33 |
| 5,631,329 | 5/1997 | Yin et al. | 525/417 |

*Primary Examiner*—Neil S. Levy
*Attorney, Agent, or Firm*—Price, Heneveld, Cooper, Dewitt & Litton

[57] ABSTRACT

A novel class of hyper comb-branched polymers conjugated with carried materials are disclosed.

92 Claims, 28 Drawing Sheets

Scheme I Synthesis of Hyper Comb-Branched Polymers.
1. Polymerization
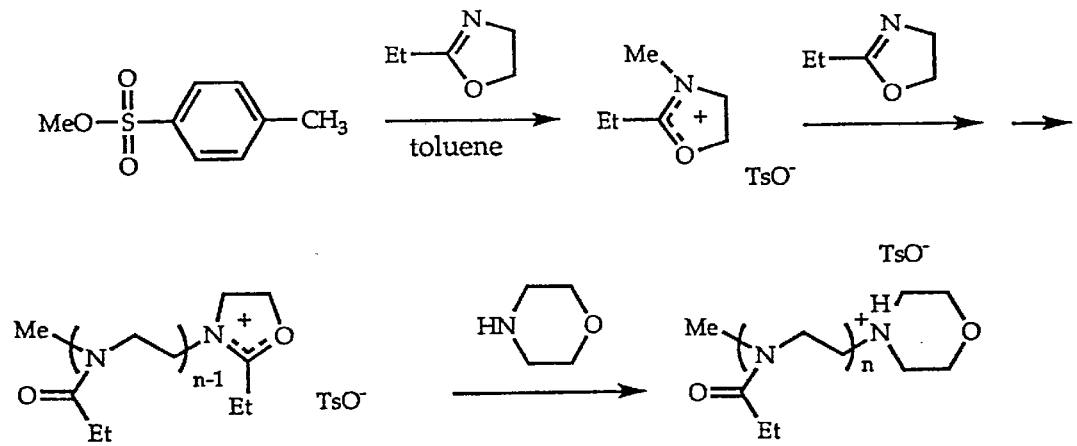
2. Hydrolysis
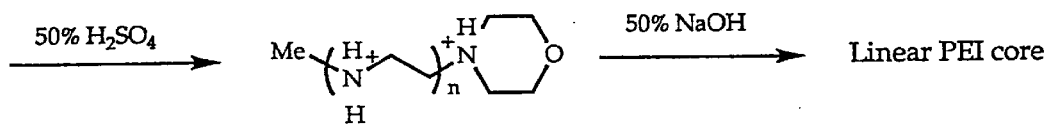
3. Grafting
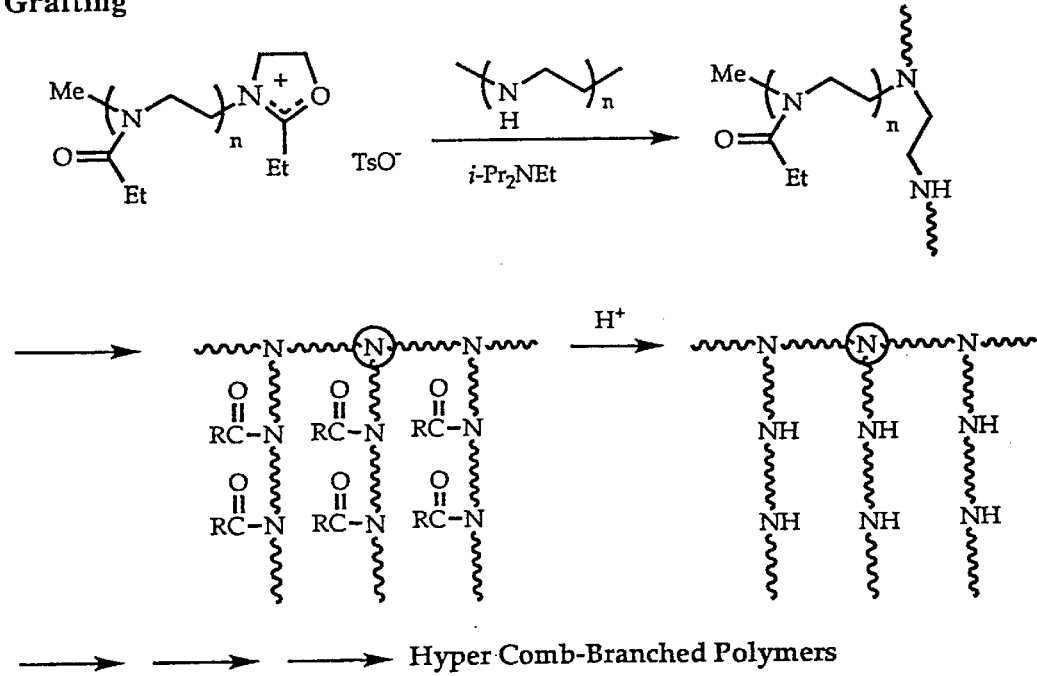
Fig. 14

1. Synthesis of Block Copolymers
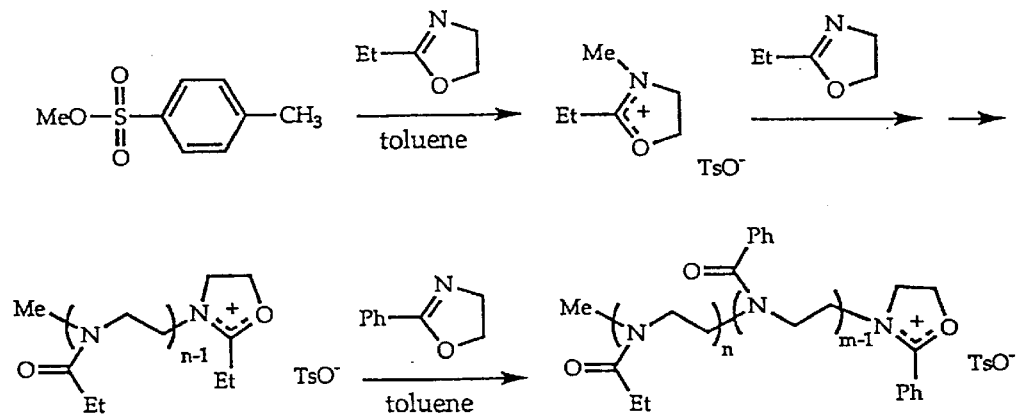
2. Grafting
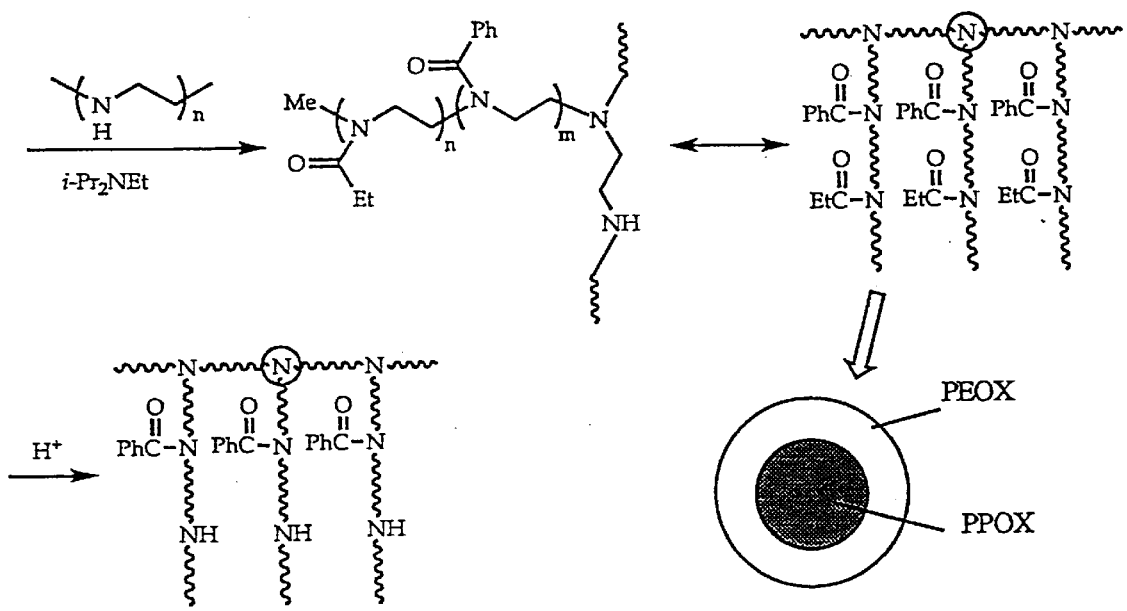
→ → Amphiphilic Hyper Comb-Branched Polymers
Fig. 21

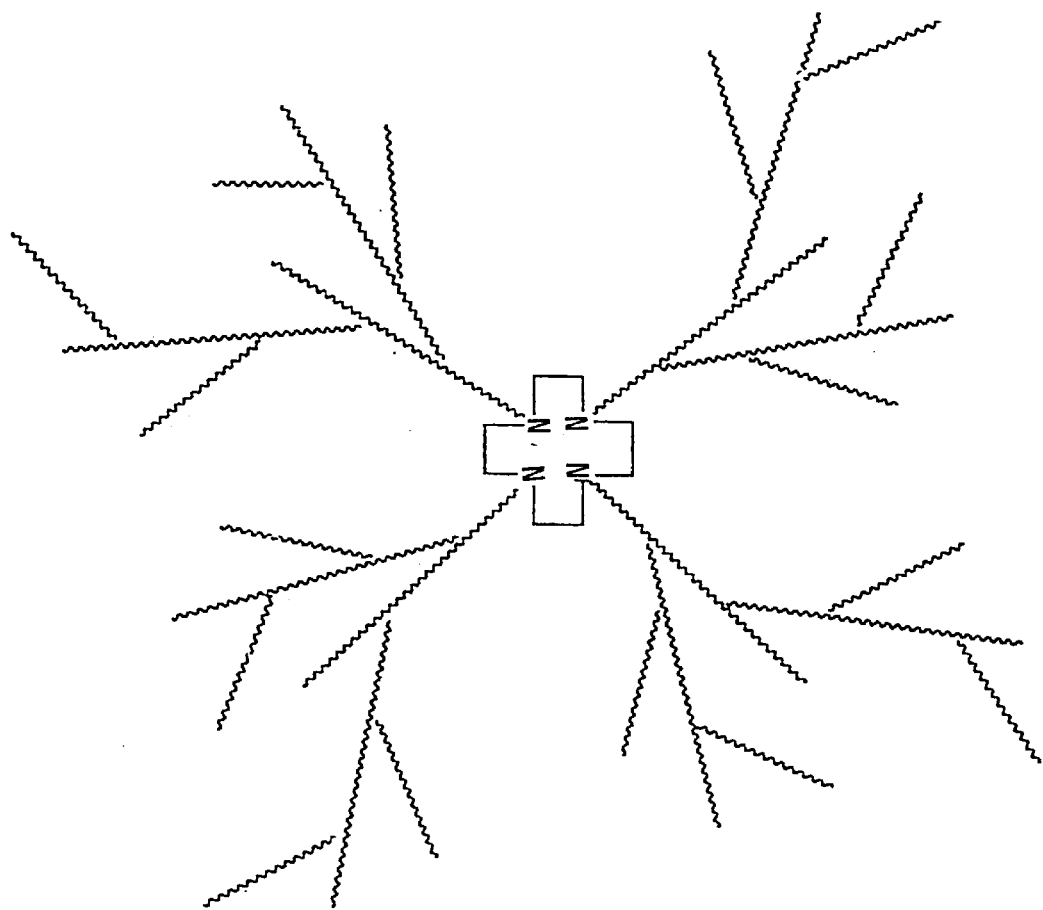
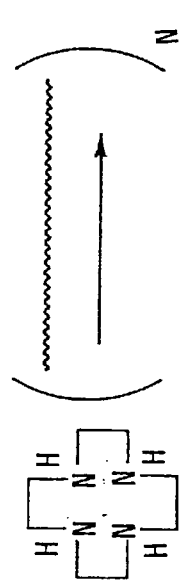
Fig. 27

HYPER COMB-BRANCHED POLYMER CONJUGATES

This application claims the benefit of U.S. Provisional application No. 60/002,202, filed Aug. 11, 1995, U.S. Provisional application No. 60/002,833, filed Aug. 25, 1995, U.S. Provisional application No. 60/003,105, filed Sep. 1, 1995, and U.S. Provisional application No. 60/004,108, filed Sep. 21, 1995.

BACKGROUND OF THE INVENTION

It is believed that there is no art defined field to which the present invention relates. The closest which one might come to categorizing the present invention would be to analogize it to the emerging experimentation involving the attachment of a carried material to a macromolecule.

For example, branched polyethyleneimine (PEI), polylysine, DEAE-dextran and polyvinylpyridinium salts have been used to carry genetic material into cells. Recently issued U.S. Pat. No. 5,338,532, entitled STARBURST™ CONJUGATES, discloses conjugating a variety of carried materials, including genetic materials, with dense star polymer marcromolecules.

Beyond these examples, Applicants know of no other types of macromolecules which are being used to carry materials.

Further, these types of macromolecules are so distinctively different that the appropriateness of categorizing them in the same field is questionable. The present invention relates to the use of yet another strikingly different type of macromolecule to carry materials for a variety of purposes.

SUMMARY OF THE INVENTION

Surprising and nonobvious advantages are achieved by conjugating carried materials with a unique class of macromolecules referred to herein as hyper comb-branched polymers. The present invention is directed to polymer conjugate materials comprising hyper comb-branched polymers associated with desired carried materials, processes for preparing those conjugates, compositions containing the conjugates, and methods of using the conjugates in compositions.

BRIEF DESCRIPTION OF THE DRAWINGS

FIG. 14 illustrates a synthesis for the preferred hyper comb-branched polymers of the present invention;

FIG. 21 illustrates a synthesis for producing hyper comb-branched polymers via a block copolymerization method;

Figure 28:
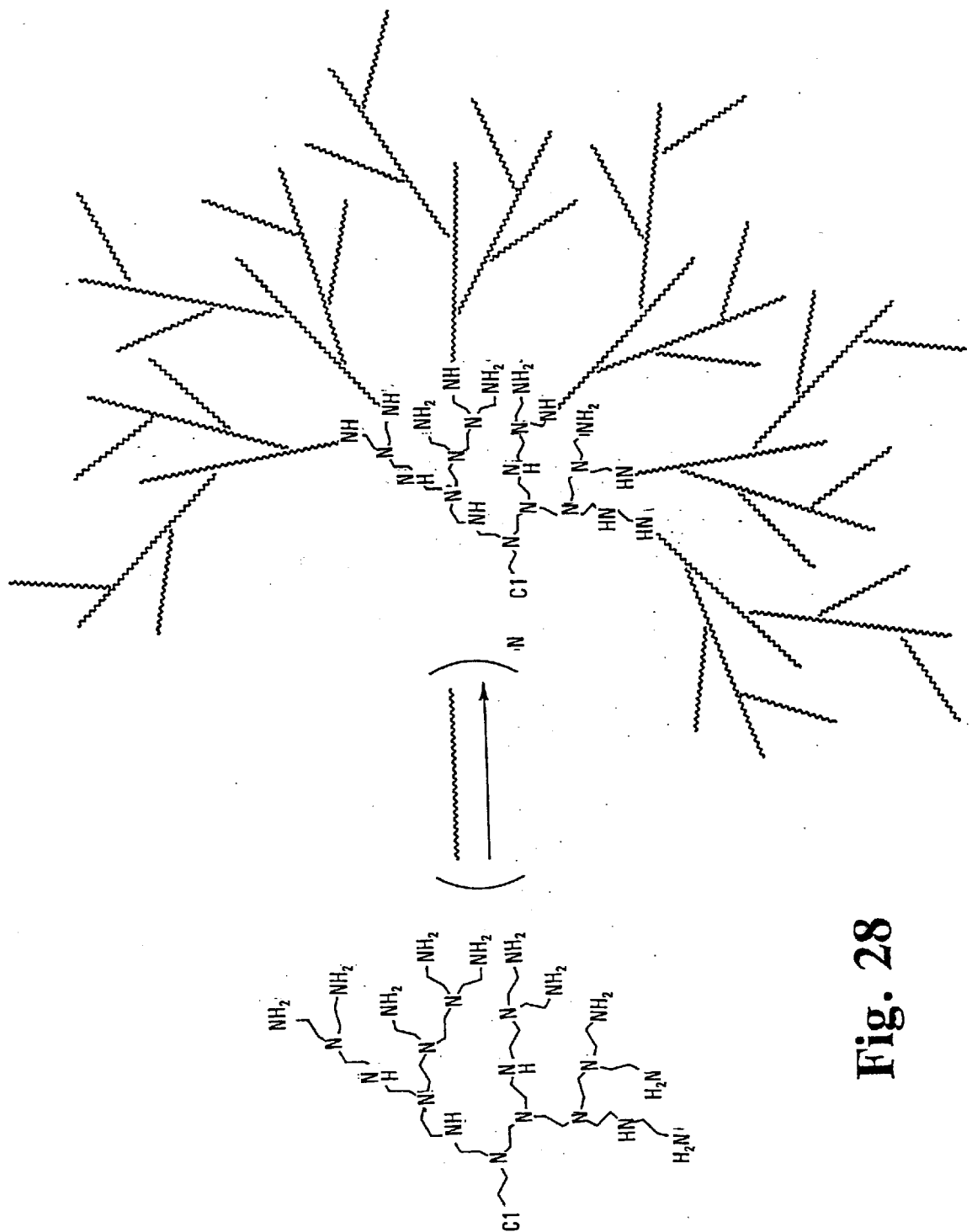

2 is the first grafting and first branching and generation 0;

3 is second grafting and second branching and generation 1;

4 is third grafting and third branching and generation 2;

5 is fourth grafting and fourth branching and generation 3;

6 is $(i+1)^{th}$ grafting and $(i+1)^{th}$ branching and generation i; and 7 is $(i+2)^{th}$ and all iterative grafting and $(i+2)^{th}$ and all iterative branching, and generation (i+1) and all subsequent generations;

FIG. 27 illustrates the grafting of oligomer branches to cyclen, and the subsequent grafting of branches upon branches; and FIG. 28 shows the grafting of oligomer branches onto a polyethyleneamine dendrimer core, and the subsequent grafting of branches upon branches.

Figure 29:
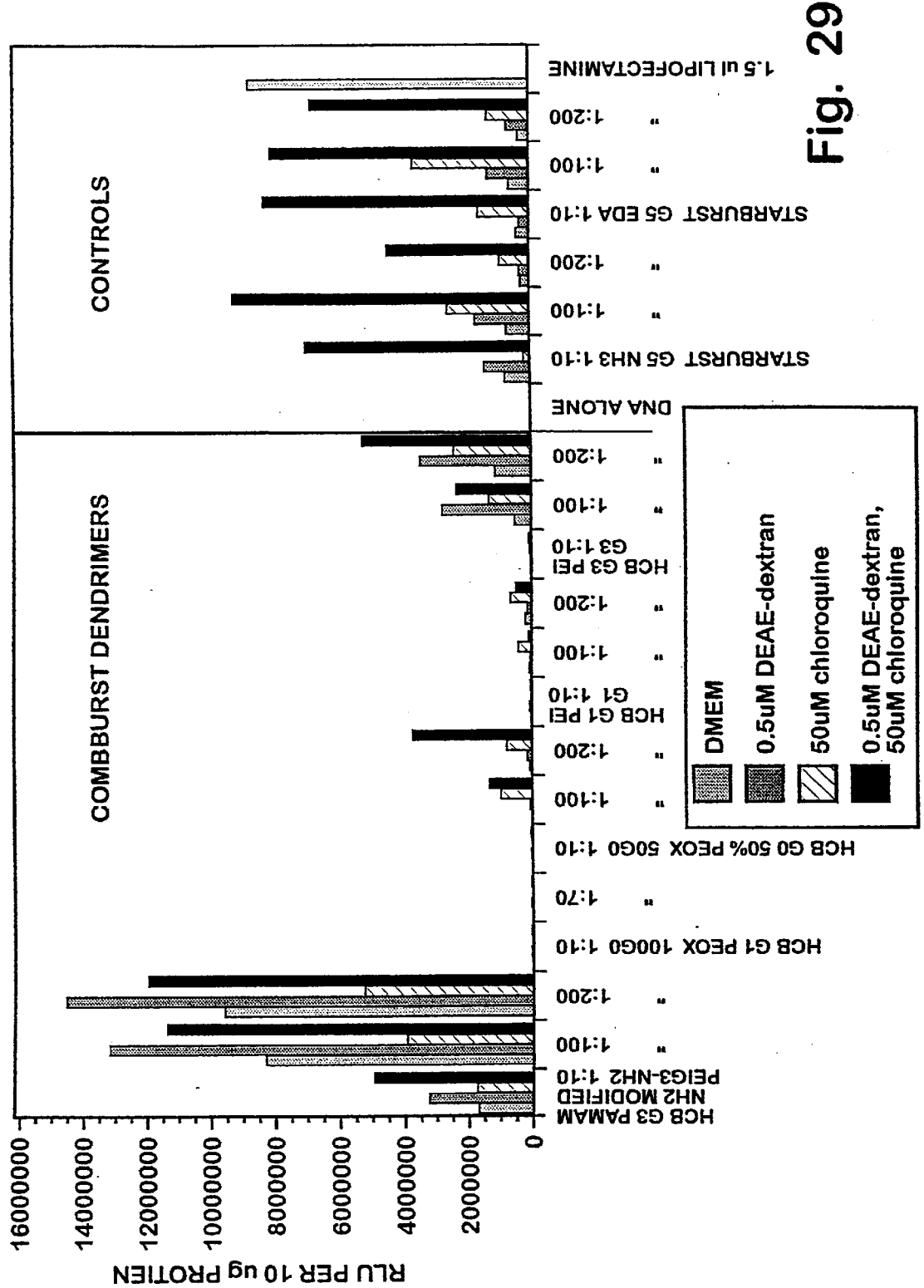
Figure 30:
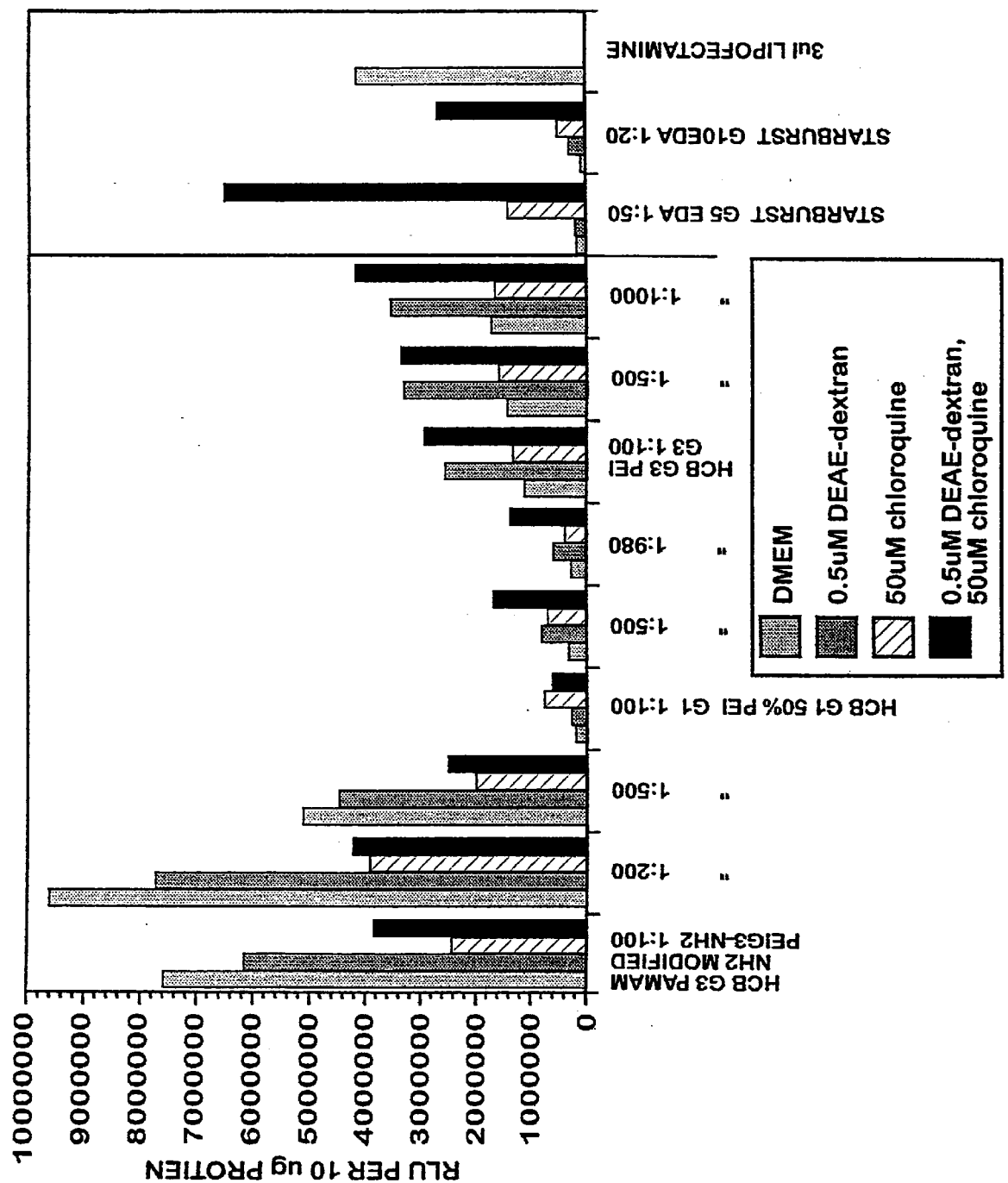
Figure 31:
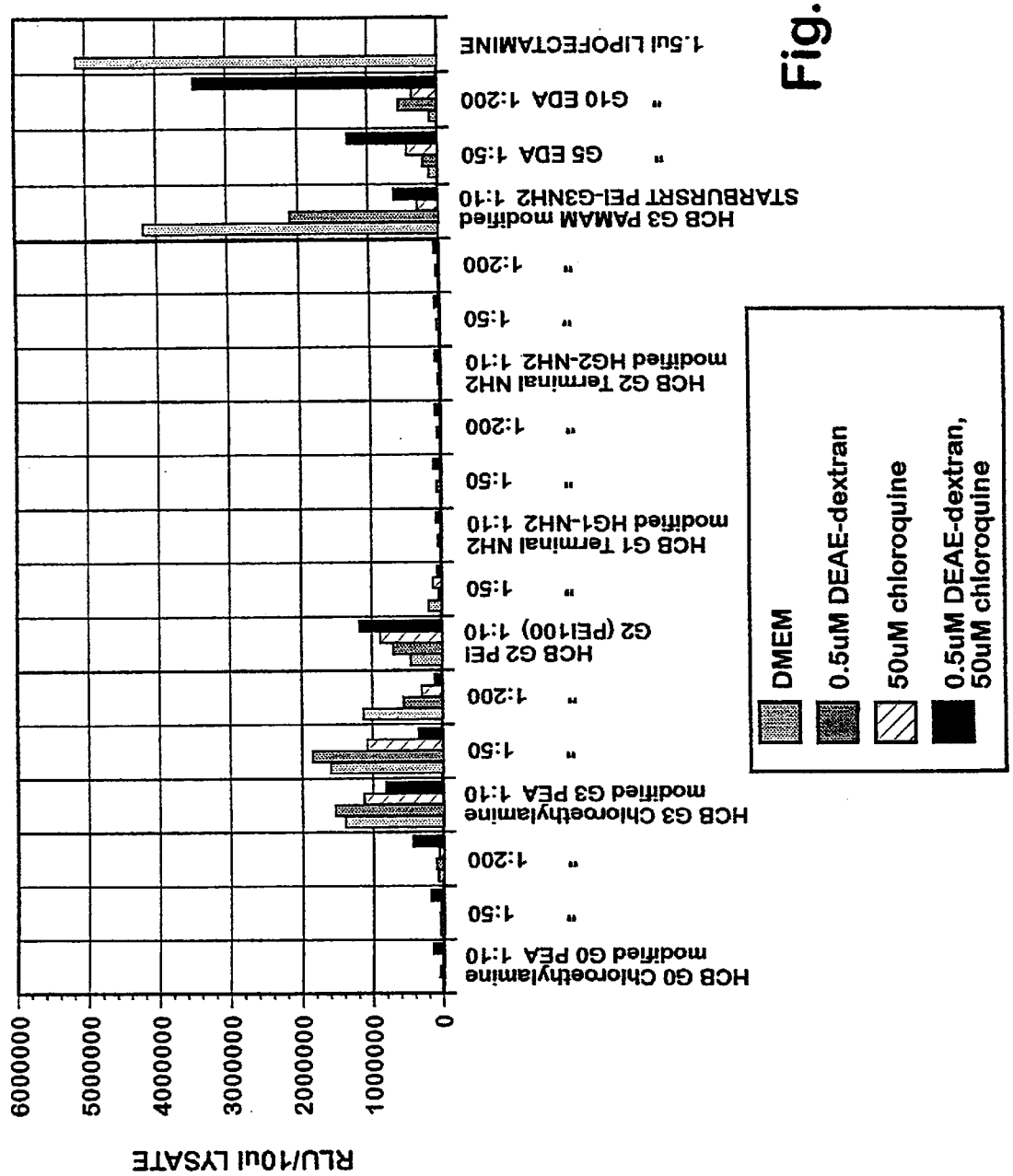
Figure 32:
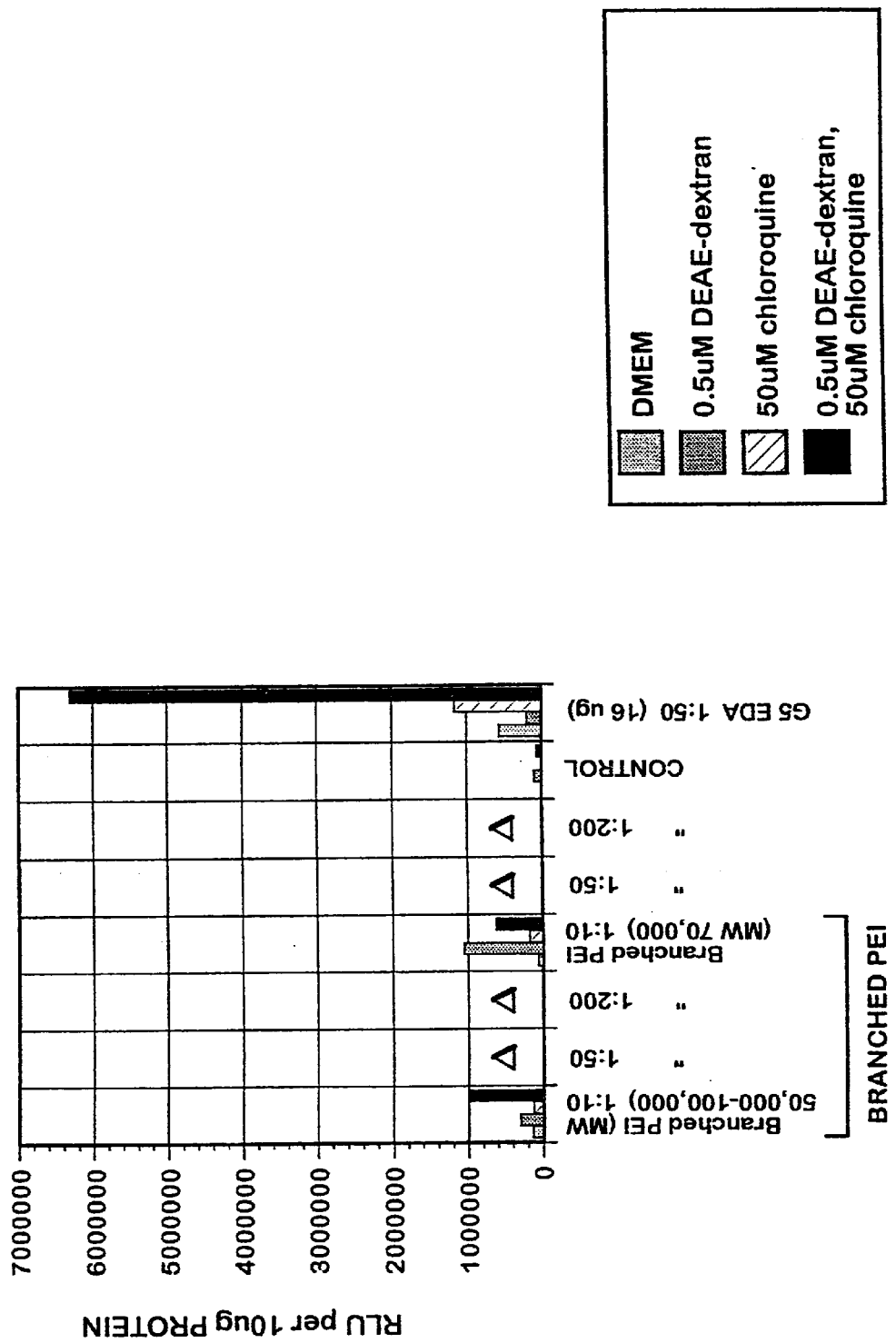
Figure 33:
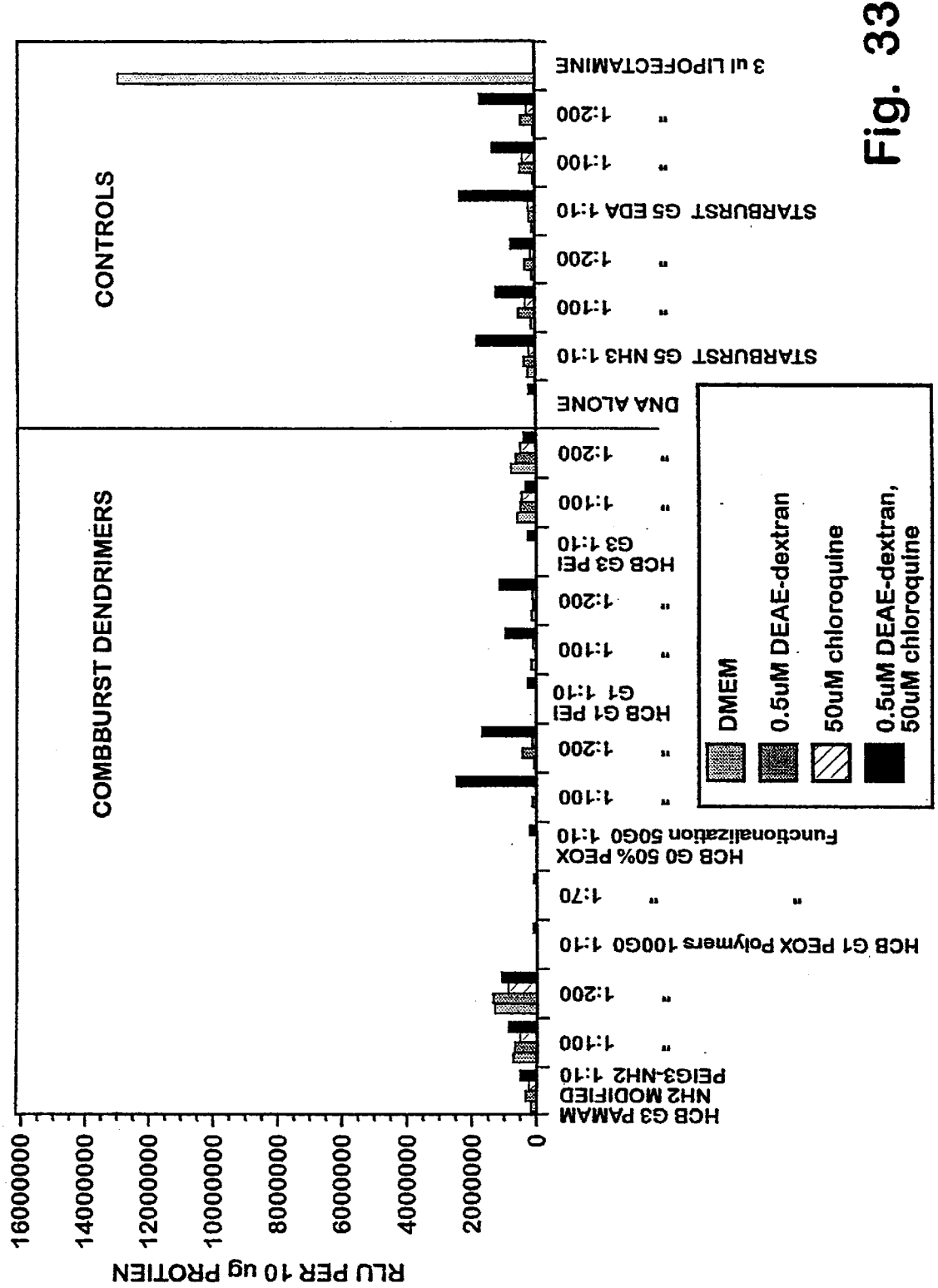
Figure 34:
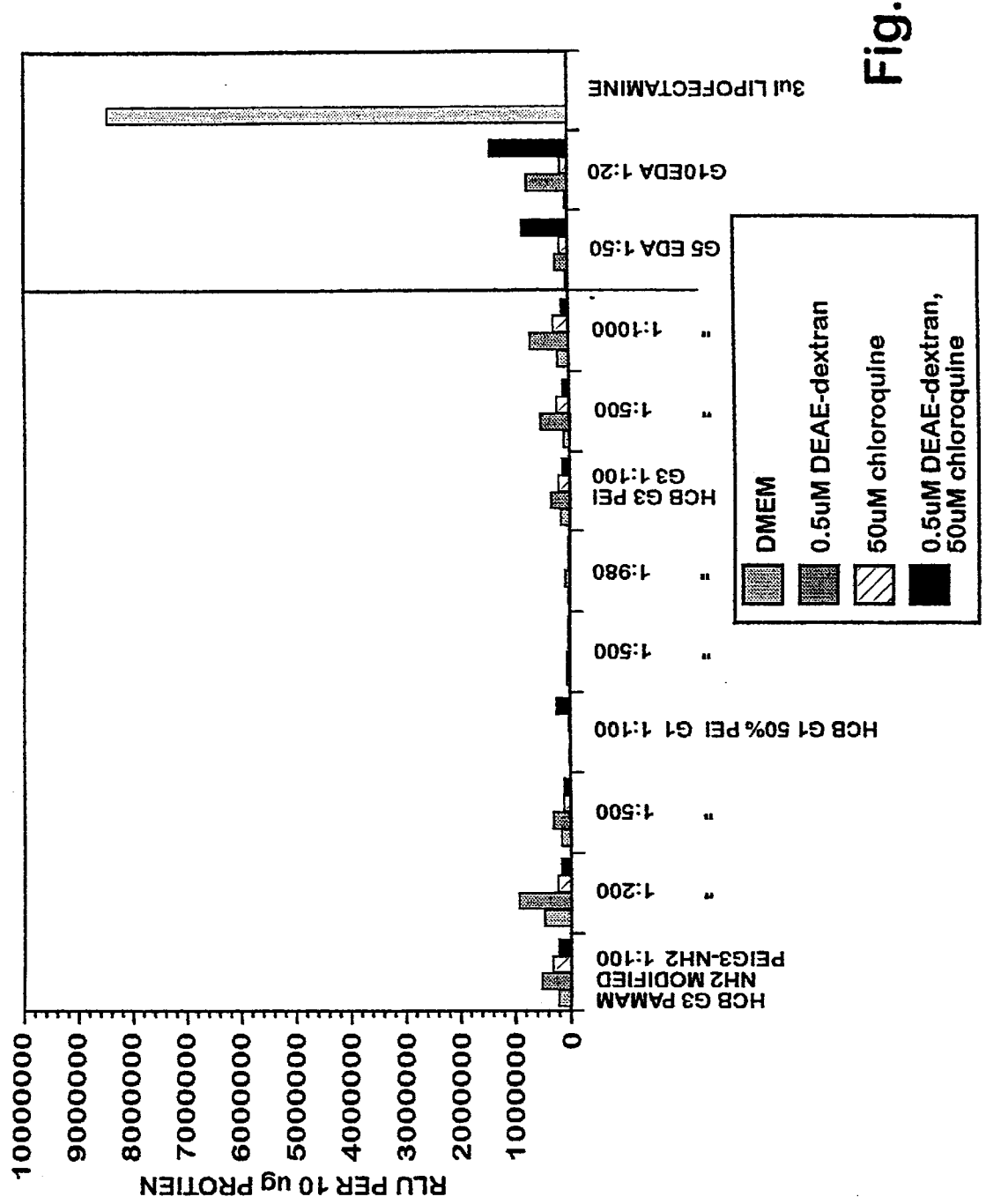
Figure 35:
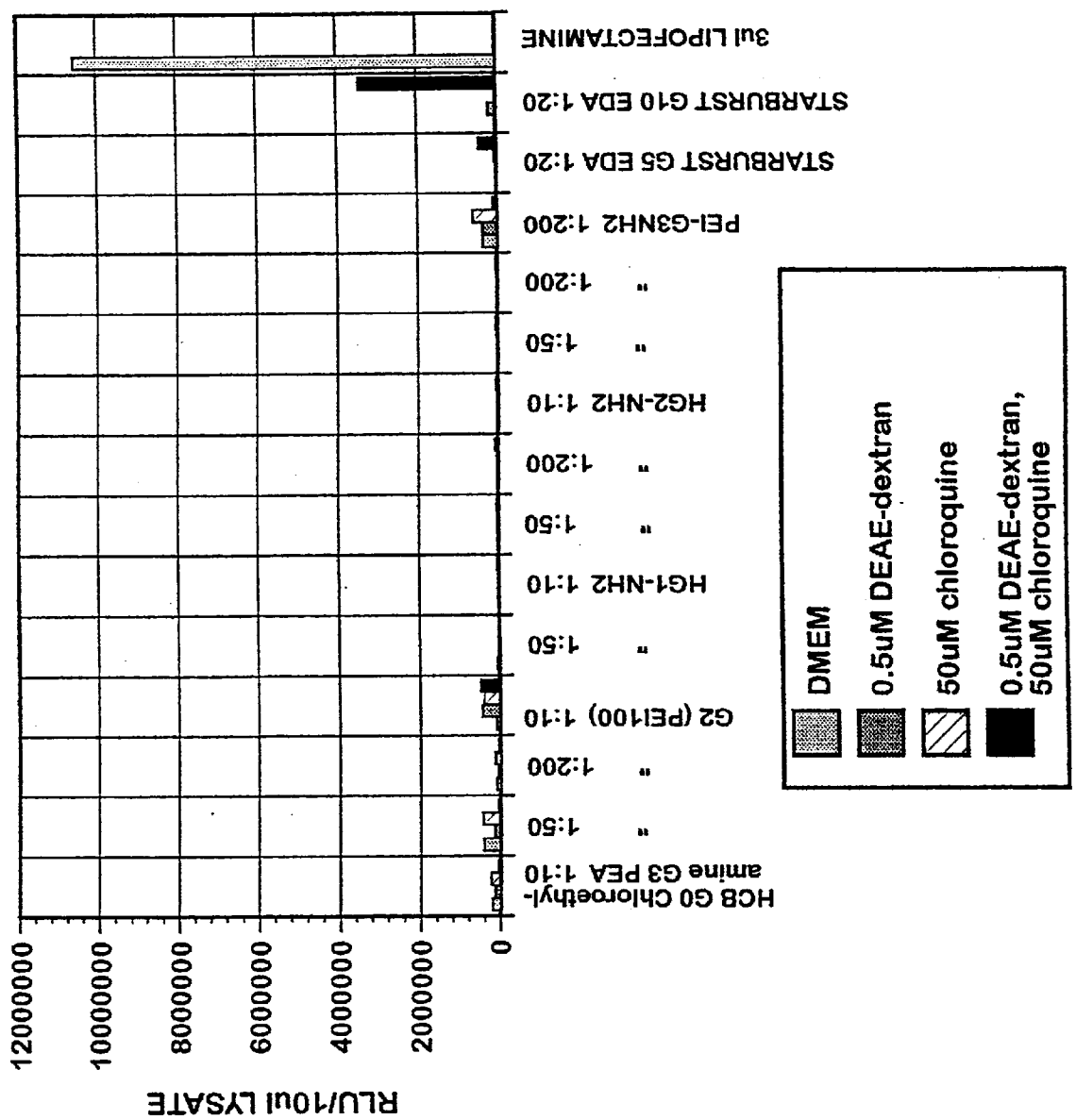
Figure 36:
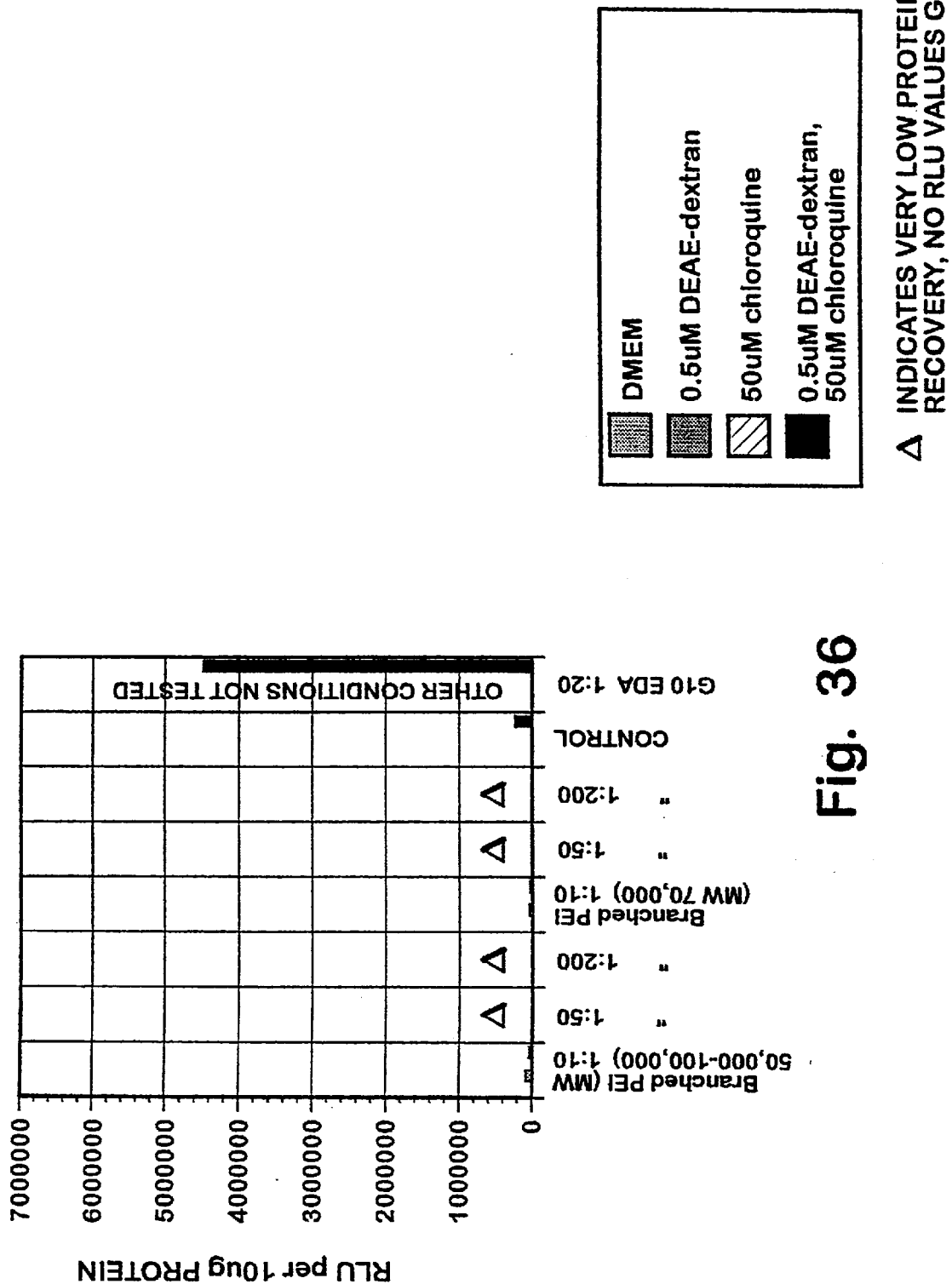
Figure 37:
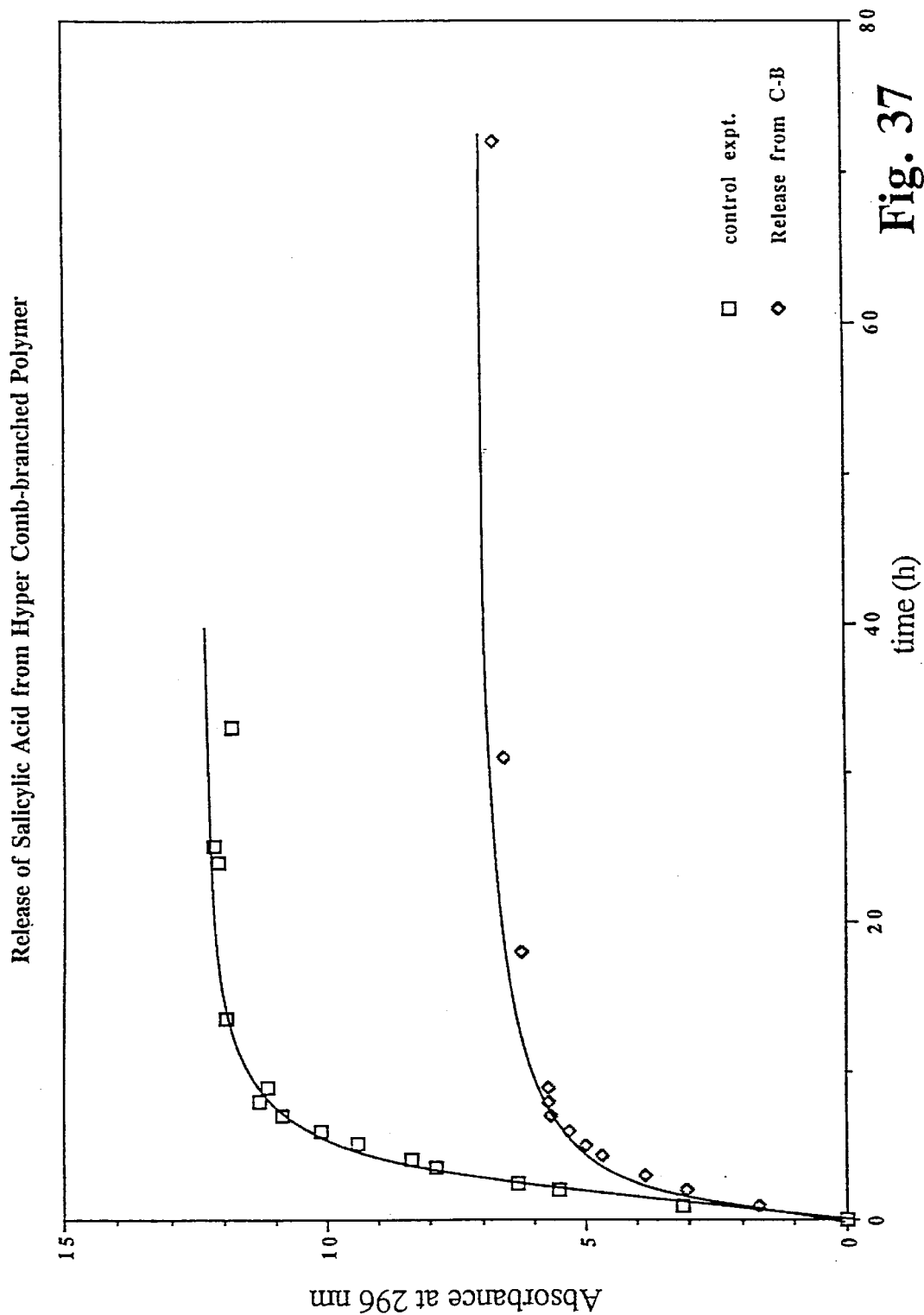

FIG. 29 illustrates luciferase activity in Cos1 cells after transfection using hyper comb-branched polymer conjugates;

FIG. 30 illustrates luciferase activity in Cos1 cells after transfection using hyper comb-branched polymer conjugates;

FIG. 31 illustrates luciferase activity in Cos1 cells after transfection using hyper comb-branched polymer conjugates;

FIG. 32 illustrates luciferase activity in Cos1 cells after transfection using branched PEI conjugates;

FIG. 33 illustrates luciferase activity in Rat2 cells after transfection using hyper comb-branched polymer conjugates;

FIG. 34 illustrates luciferase activity in Rat2 cells after transfection using hyper comb-branched polymer conjugates;

FIG. 35 illustrates luciferase activity in Rat2 cells after transfection using hyper comb-branched polymer conjugates;

FIG. 36 illustrates luciferase activity in Rat2 cells after transfection using branched PEI conjugates; and FIG. 37 illustrates release of salicylic acid from hyper comb-breached polymer.

DETAILED DESCRIPTION OF THE PREFERRED EMBODIMENTS

The Hyper Comb-Branched Polymers

Figure 1:
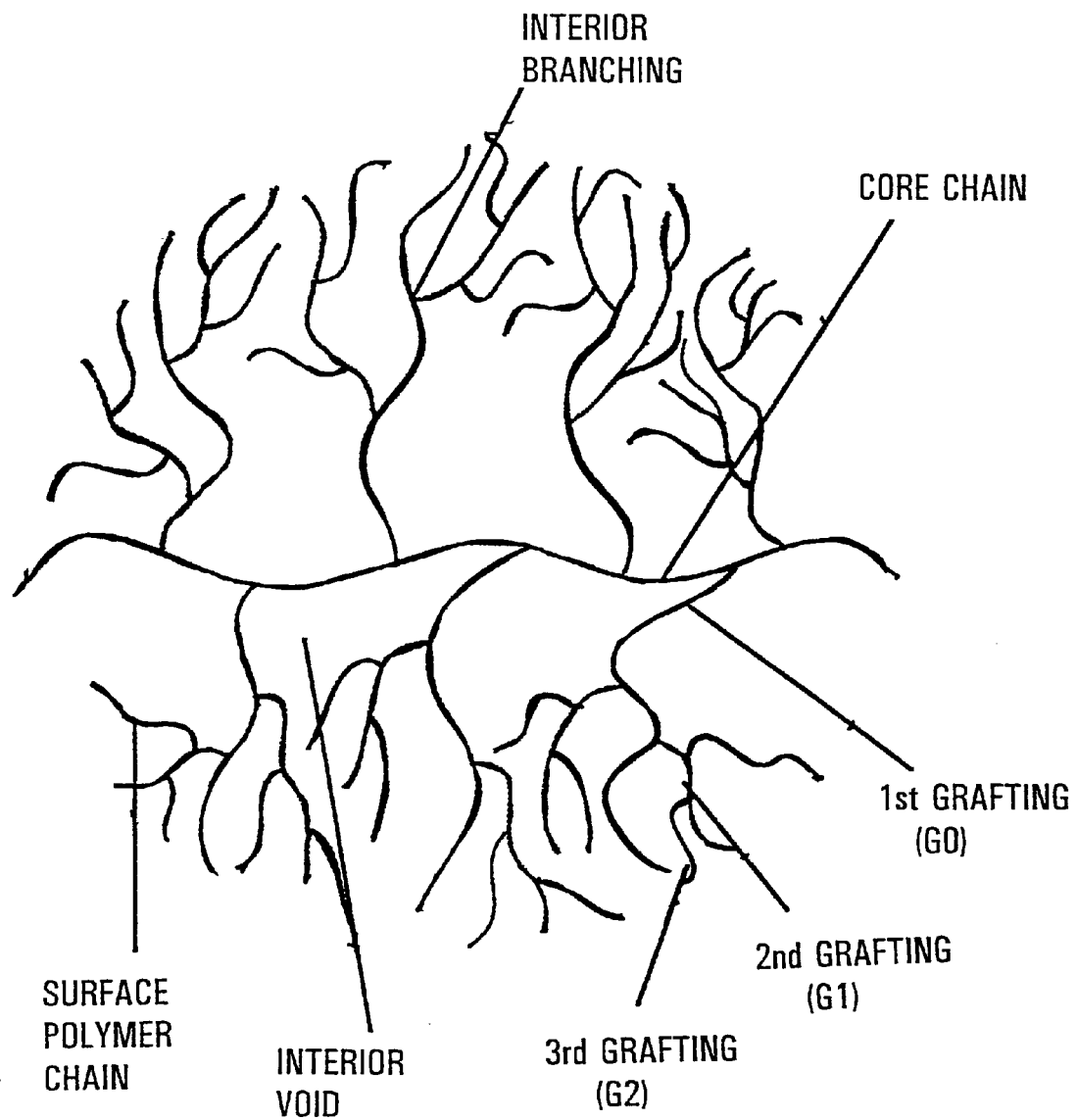
FIG. 1 illustrates a preferred embodiment hyper comb-branched polymer used in the conjugates of the present invention.

A hyper comb-branched polymer of the preferred embodiment as illustrated in FIG. 1 comprises a generally linear core chain, successive generations of oligomers branching off the core and prior generations of branches, an exterior surface formed by the termini of the last generation of branches, and interior voids within the polymer molecule.

A comb-branched polymer comprises an elongated core with a plurality of arms branching therefrom to give the appearance of a comb. "Hyper comb-branched" polymers comprise successive generations of branches branching off of prior generations of branches. The resulting structure has an exceedingly high degree of branching, and so is referred to as "hyper comb-branched." Hyper comb-branched polymers are sometimes referred to herein by their trademark: hyper comb-branched polymer™.

Figure 2:
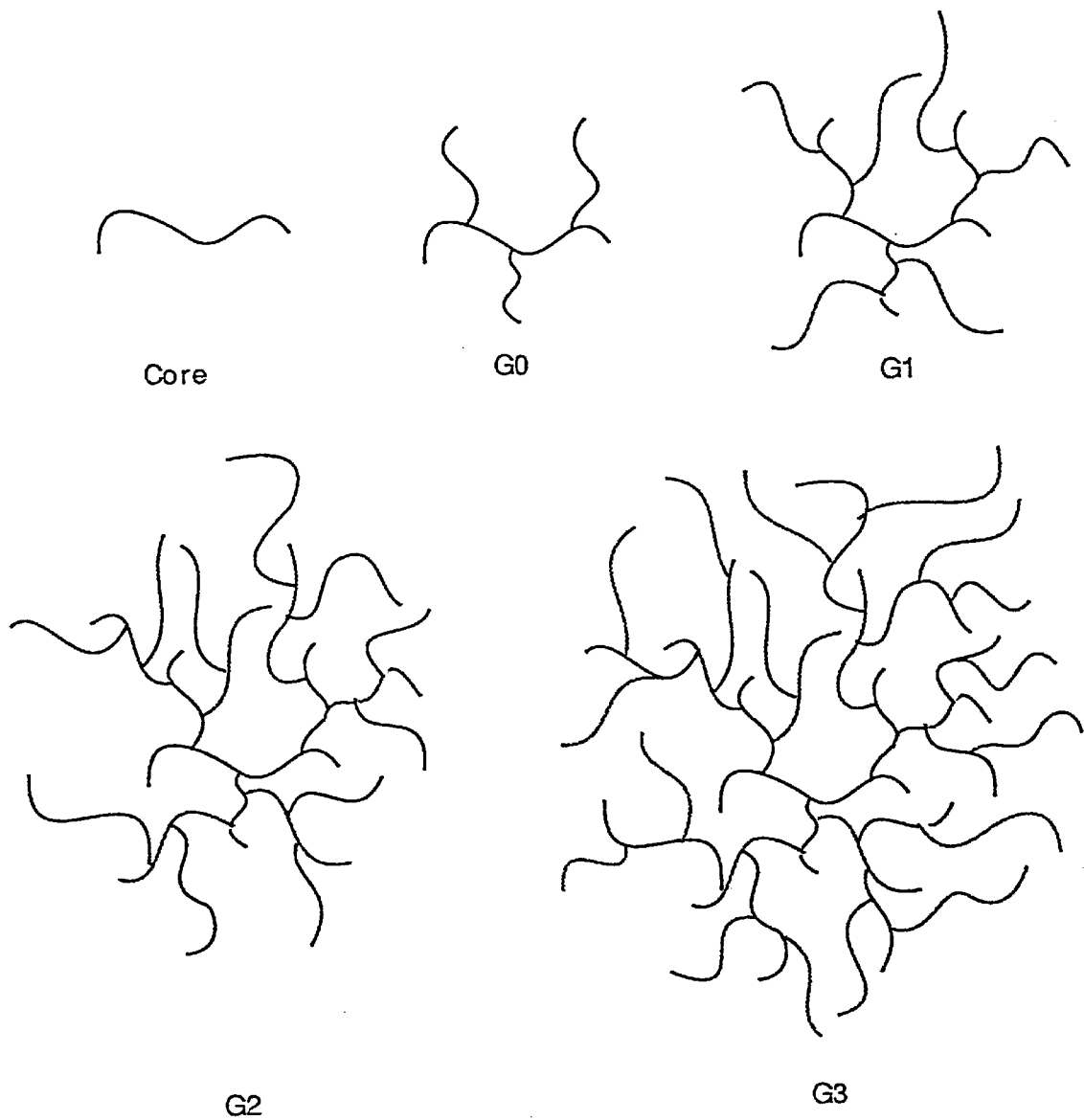
FIG. 2 illustrates the constituents of hyper comb-branched polymers comprising a core and four successive branching generations.

Hyper comb-branched polymers are defined based upon the number of generations or grafting steps. As illustrated in FIG. 2, a hyper comb-branched polymer is constructed by grafting or attaching a series of branching arrays to a core, or predecessor branches. The first grafting array is defined as generation 0 (G0), the second grafting array is generation 1 (G1), the third grafting array is generation 2 (G2), the fourth array is generation 3 (G3), and so on. This novel design not only significantly reduces the synthetic effort for obtaining higher molecular weight (i.e. greater than 10 million, with a molecular weight distribution of about 1.2) or larger size (i.e. a diameter greater than about 100 nm) dendritic polymers, but also enables the designer to tailor particular structural attributes of the hyper comb-branched polymers.

Structural aspects that may be varied include, but are not limited to, interior grafting density, interior void volume or "cargo space," spacing between generations, types of branches utilized in each generation, the number and types of terminal moieties or functional outer groups disposed at or near the surface of the polymer molecule, and lateral cross-sectional diameter or geometric configuration of the polymer.

Figure 3:
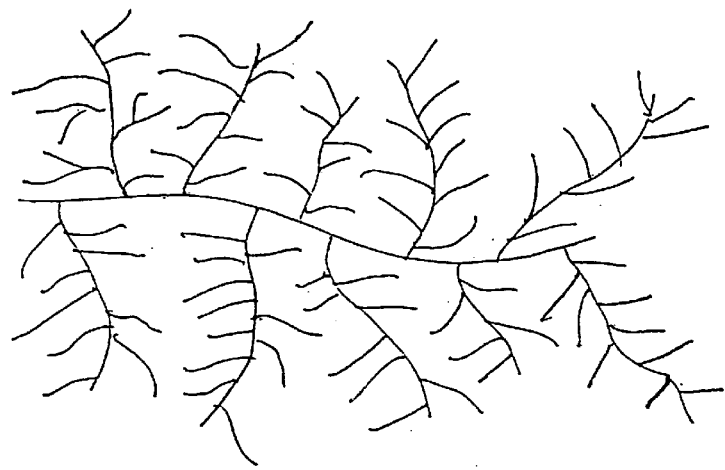
FIG. 3 illustrates a preferred embodiment hyper comb-branched polymer having a relatively high grafting density.
Figure 4:
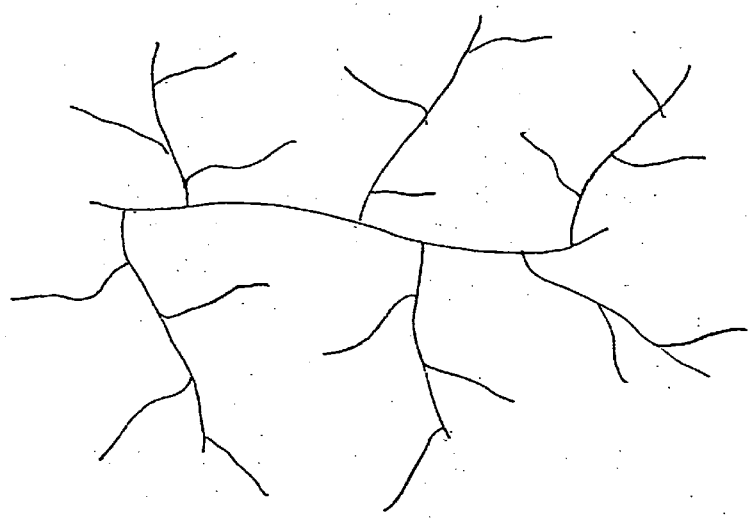
FIG. 4 illustrates a preferred embodiment hyper comb-branched polymer having a relatively low grafting density.

FIGS. 3 and 4 illustrate two preferred hyper comb-branched polymers having different grafting densities. FIG. 3 depicts a polymer having a relatively high grafting density in which adjacent branches are tightly packed or closely situated to one another. In contrast, FIG. 4 illustrates a polymer having a relatively low grafting density, in which the polymer has a much looser structure. Grafting density can be controlled by the choice of branching or repeating unit type employed at each generation, number of reactive sites of the core and branches, and reaction conditions utilized during assembly of the hyper comb-branched polymers. The hyper comb-branched polymers utilized in the present invention can have a grafting density of from about 0.1% to about 90% or higher such as 100%. Grafting density as referred to herein is defined as the number of attachment or graft sites on a constituent, i.e. core or branch, of the hyper comb-branched polymer expressed as a percentage of the total number of sites in the polymer available for grafting or attachment thereto during assembly of the polymer. Generally, relatively high grafting densities can be achieved by utilizing small core and branch structures.

Figure 5:
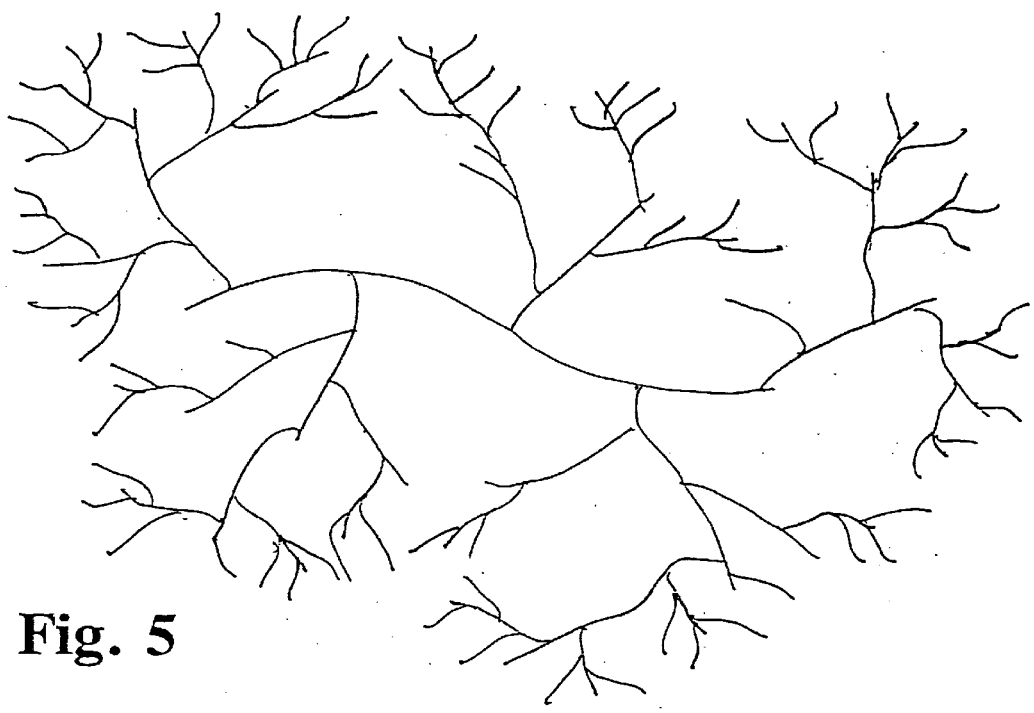
FIG. 5 illustrates a preferred embodiment hyper comb-branched polymer having a relatively large interior void volume.
Figure 6:
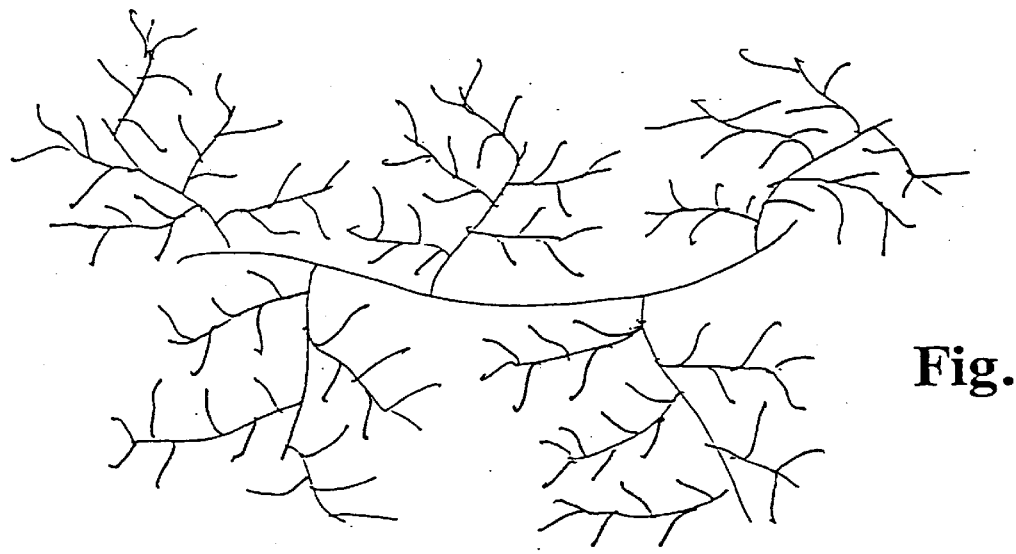
FIG. 6 illustrates a preferred embodiment hyper comb-branched polymer having a relatively small interior void volume.

FIGS. 5 and 6 illustrate two preferred hyper comb-branched polymers having significantly different interior void volumes. FIG. 5 depicts a polymer having a relatively large interior volume while FIG. 6 illustrates a polymer having a relatively small interior volume. Different interior void spaces can be achieved by varying grafting densities, core and branch chain length, number of reactive sites on the core and early generation branches, spacing between branches, and combinations of these parameters. The hyper comb-branched polymers utilized in the present invention can have an interior void volume of about 10 angstroms to about 500 angstroms or more. Void volume as referred to herein generally refers to the void size, and in most instances the interior cavity diameter.

Figure 7:
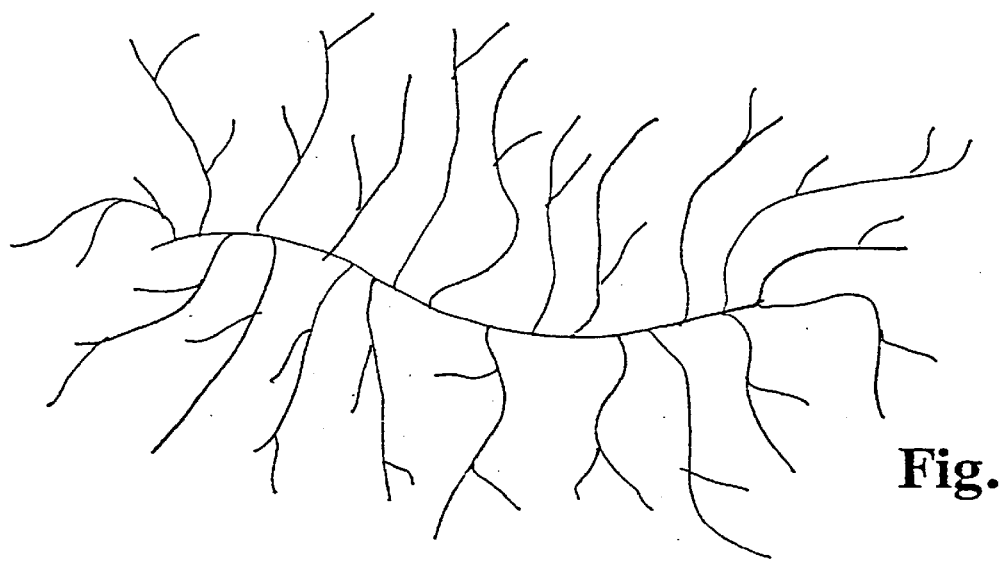
FIG. 7 illustrates a preferred embodiment hyper comb-branched polymer having relatively close spacing between first generation branches and relatively distant spacing between second generation branches.
Figure 8:
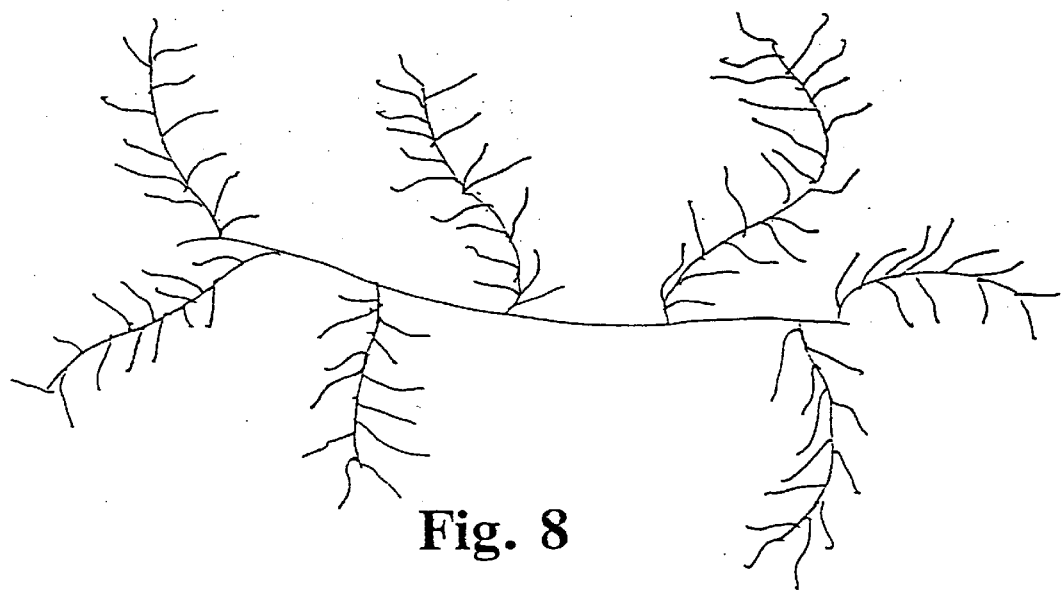
FIG. 8 illustrates a preferred embodiment hyper comb-branched polymer having relatively distant spacing between first generation branches and relatively close spacing between secondary branches.

FIGS. 7 and 8 illustrate hyper comb-branched polymers having different spacing configurations between successive generations. The polymer depicted in FIG. 7 has a much closer spacing between first generation branches than the polymer illustrated in FIG. 8. However, the polymer of FIG. 8 has a much closer spacing between second generation branches than the polymer illustrated in FIG. 7. Successive branching generations can be specifically tailored as previously described with respect to adjusting grafting density and interior void volume, to produce particular spacing configurations at desired regions within the hyper comb-branched polymer. In one embodiment, a hyper comb-branched polymer comprises multiple regions of different grafting densities. Thus, such a polymer could comprise alternating regions of different grafting densitites such as a first region having a grafting density less than about 50%, and another region having a grafting density of more than about 50%.

Figure 9:
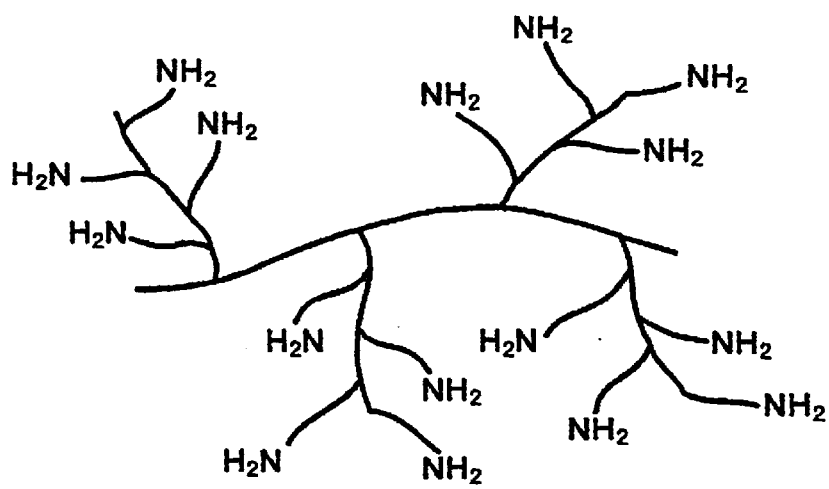
FIG. 9 illustrates a preferred embodiment hyper comb-branched polymer having $NH_2$ groups as terminal moieties.
Figure 10:
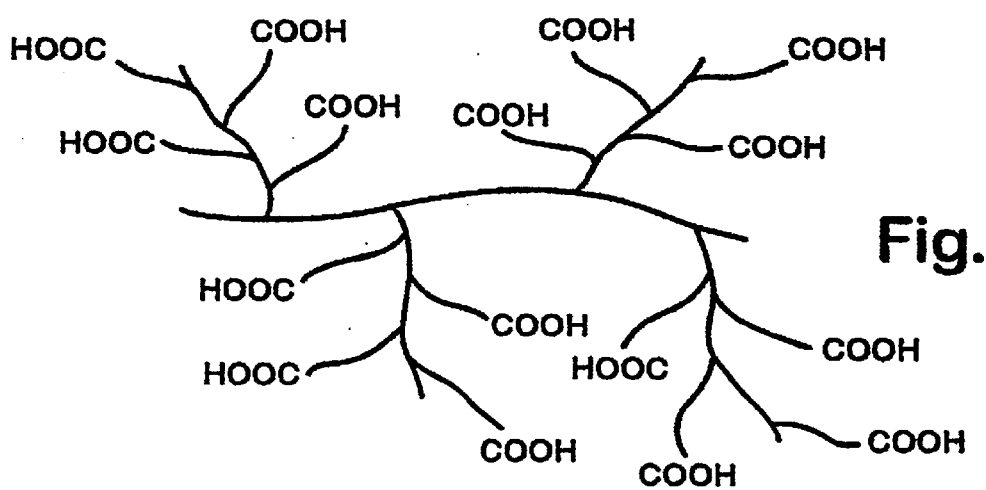
FIG. 10 illustrates a preferred embodiment hyper comb-branched polymer having COOH groups as terminal moieties.

FIGS. 9 and 10 illustrate hyper comb-branched polymers having particular chemical moieties disposed generally about the periphery of each molecule. Various physical and functional characteristics can be imparted to the hyper comb-branched polymer depending upon the types, combinations, and/or degree of surface congestion or number of terminal moieties disposed about the periphery of the polymer. Functionalization of the polymer surface can be achieved either by direct modification of hyper comb-branched polymers with various organic reagents (i.e. alkylene oxide), or by forming hyper comb-branched polymers having —$NH_2$, —COOH, —COOMe, —$NH_4$, —PEOX, —PEG, —PEO, or combinations thereof, followed by functionalization with the desired surface molecules (FIGS. 8 and 9). In addition to functionalization of the polymer surface, a wide variety of chemical moieties may be disposed at different regions within a polymer molecule by incorporating the desired moieties in particular branching generations.

Figure 11:
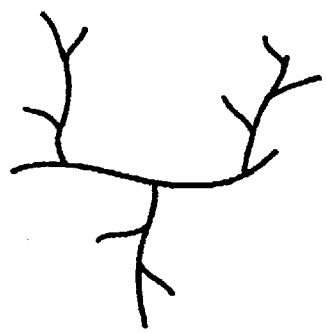
FIG. 11 illustrates a preferred embodiment hyper comb-branched polymer of relatively small outer dimensions.
Figure 12:
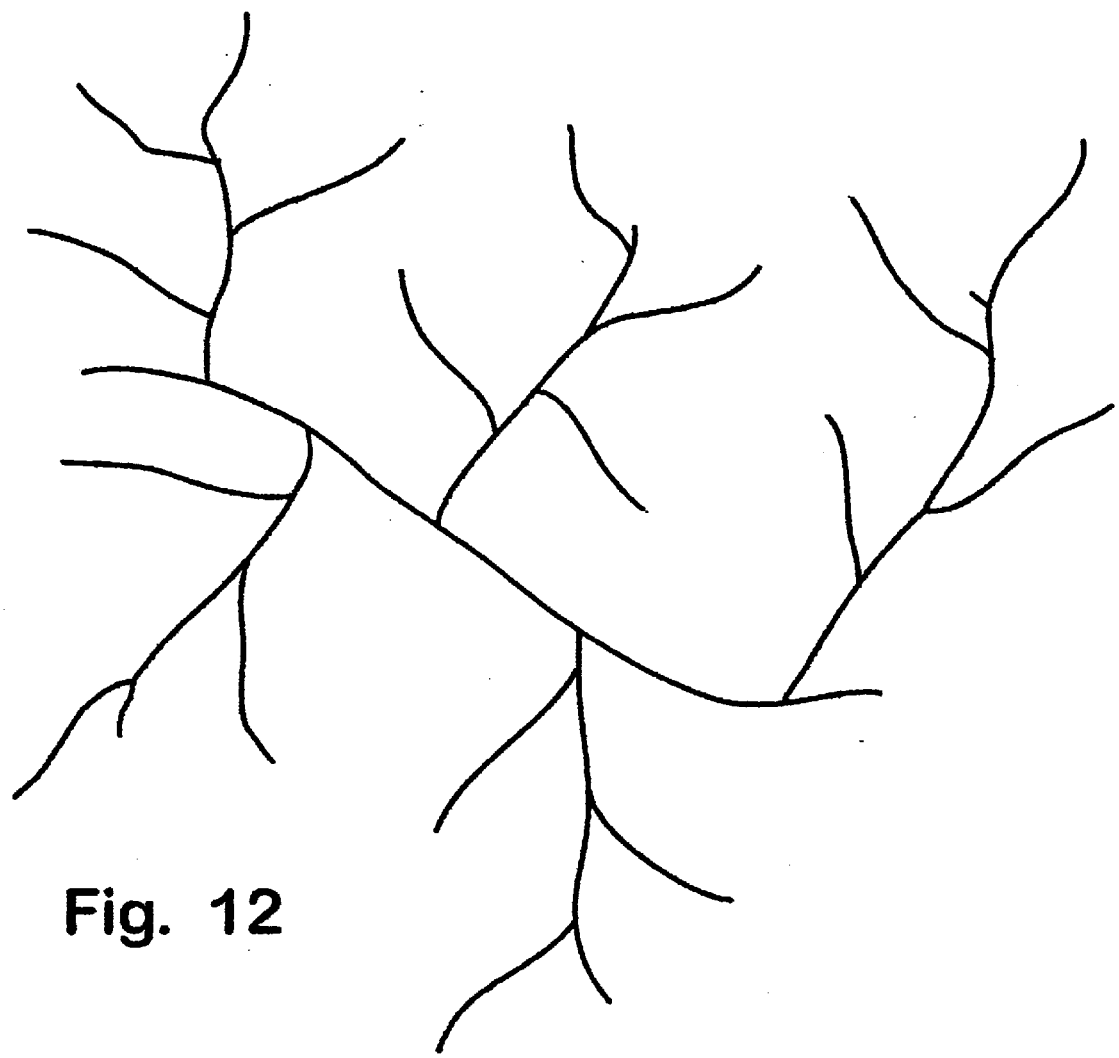
FIG. 12 illustrates a preferred embodiment hyper comb-branched polymer of relatively large outer dimensions.

The overall size of a hyper comb-branched polymer may be varied as shown in FIGS. 11 and 12. Relatively large hyper comb-branched polymers, such as that depicted in FIG. 12 can be prepared, as disclosed below, by utilizing relatively long core and branching chains as constituents for building the hyper comb-branched polymers. That is, the maximum diameter for such large polymers is generally about 100 nm. The inventors contemplate however that even larger polymers could be formed. Alternatively, relatively small hyper comb-branched polymers as shown in FIG. 11 can be formed by utilizing short core and branching chains. Hyper comb-branched polymers having particular geometries and shapes may be constructed by appropriate selection of core and branching components.

Figure 13A:
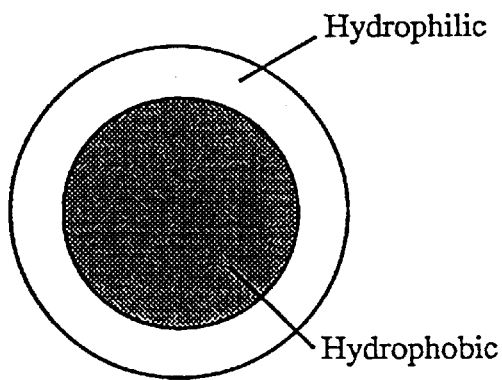
FIG. 13 illustrates several embodiments of hyper comb-branched polymers having various combinations of hydrophilic and hydrophobic branching generations.
Figure 13B:
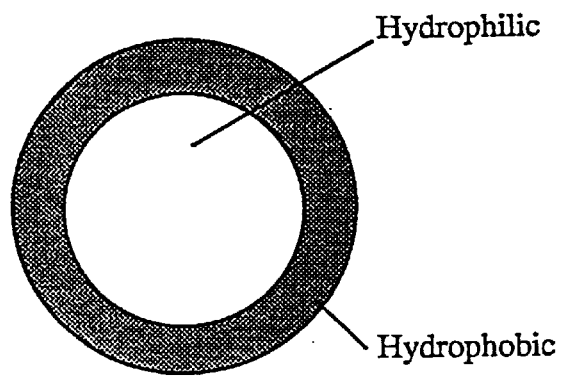
Figure 13C:
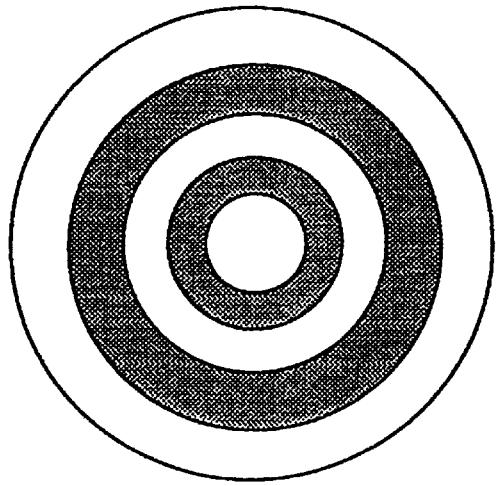

In addition to controlling structural aspects of the hyper comb-branched polymers described herein, particular functional characteristics may be incorporated in the polymer during its assembly. For example, as illustrated in FIG. 13(*a*), a hyper comb-branched polymer with a hydrophobic interior and a hydrophilic exterior can be obtained by sequential synthesis of an initial hydrophobic interior and then a hydrophilic exterior. Alternatively, such a polymer may be produced by functionalizing the exterior or last generation branching array with hydrophilic polymers, followed by modification of the interior with hydrophobic monomers. Hydrophilic functionalization can be achieved by grafting hydrophilic polymers such as poly(2-ethyloxazoline), poly(2-methyloxazoline), polyethylene glycol, polyethylene oxide, polyacrylic acid, polyacrylic amide, polyvinyl pyrrolidone, and combinations thereof at the desired grafting step. Conversely, a hyper comb-branched polymer with hydrophobic outer surfaces as shown in FIG. 13(*b*) can be prepared by grafting hydrophobic polymers such as polyethylene, polydimethylsiloxane, polybutadiene, polystyrene, polymethyl-methacrylate, perfluoropolymer, and poly(2-alkyl or phenyl oxazolines) etc. at the last grafting step. In applications employing poly(2-alkyl oxazolines), hydrophobicity is achieved when the alkyl group has about 4 or more carbon atoms. In addition, a hyper comb-branched polymer with alternating hydrophobic-hydrophilic layers as depicted in FIG. 13(*c*) may be prepared by using amphiphilic polymers between each grafting step.

Hyper comb-branched polymers have also been referred to as non-crosslinked, polybranched polymers. They have the general formula:

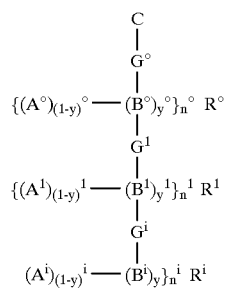

wherein:

C is a core molecule;

each R is the residual moiety of an initiator selected from a group consisting of free radical initiators, cationic initiators, anionic initiators, coordination polymerization initiators and group transfer initiators;

A and B are polymerizable monomers or comonomers capable of withstanding the conditions required for branching therefrom or grafting thereto, at least during the polymerization of the {(A)—(B)} linear polymer chain and during its grafting to a prior {(A)—(B)} branch or the {(A)—(B)} core branch;

each G is a grafting component, and the designation

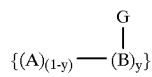

indicates that G can attach to either an (A) unit or a (B) unit;

n is the degree of polymerization of the indicated generation comb branches;

y is the fraction of B units in the indicated generation branch, and has a value of 0.001 to 1;

the superscripts 0, 1 and i designate the comb-branch generation level, with i beginning at "2" and continuing for the number of reiterative branch set generations in the polymer; and at least $n^\circ$ and $n^1$ are $\geq 2$.

One process for producing hyper comb-branched polymers uses the following scheme: (1) forming a first set of branches by initiating the polymerization of a first set of monomers which are either protected against or non-reactive to branching and grafting during said polymerization, each of said branches having a reactive end unit upon completion of said polymerization, said reactive end units being incapable of reacting with each other; (2) grafting said branches to a core (preferably polymeric) having a plurality of reactive sites capable of reacting with said reactive end groups on said branches; (3) either deprotecting or activating a plurality of monomeric units on each of said branches to create reactive sites; (4) separately forming a second set of branches by repeating step (1) above with a second set of monomers; (5) attaching said second set of branches to said first set of branches by reacting said reactive end groups of said second set of branches with said reactive sites on said first set of branches.

Stated another way, the basic process for forming hyper comb-branched polymers comprises:

(I) forming a core having at least one reactive site;

(II) reacting essentially all of the reactive sites of said core with a reactive polymer having the unit formula

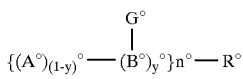

to form multiple branches which contain reactive (B°) sites on each branch, using a reactive scheme such that the reactive monomer units (B°) are capable of withstanding the conditions required for branching therefrom or grafting thereto to ensure that said reactive polymer

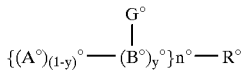

reacts with said reactive sites of said core, but that no reactions occur at said (B°) sites;

(III) repeating step (II) sequentially by reacting reactive polymer having the unit formula

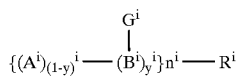

with the reactive sites of said polymerizable $B^{(i-1)}$ monomers or comonomers of the previous generation to form successive generation of branches to give the desired non-crosslinked poly-branched polymer.

There does not seem to be any limit to the size of the hyper comb-branched polymers except that dictated by practicality and/or sterochemistry of the molecules formed. Molecular weights preferably range from about 10,000 to about 100,000,000 though there may be applications where molecular weights outside of this range would be appropriate. More preferable are those having molecular weights of 10,000,000 or less. For most applications those molecules having a molecular weight of 500,000 or less are especially preferred.

The value of n° can have a range of 2 to a value of in excess of 100, but the preferred value is from 2 to 100. In addition, values of $n^1$, $n^2$, and $n^i$ can be in the range of 1 to a value in excess of 100, such as up to about 10,000 or even higher, but the preferred range is from 1 to 100. The core itself can be a linear polymer having a degree of polymerization $n^c$, whose value can be from 2 to a value in excess of 300, but a preferred range for the value of $n^c$ is from 2 to 300.

As indicated above, each of $R^0$, $R^1$, $R^2$, $R^3$, and $R^i$ in these inventive polymers is selected as a residual moiety from a radical initiator, a moiety from a cationic initiator, a moiety from an anionic initiator, a coordination polymerization initiator, or a group transfer initiator. $R^0$-$R^1$ can be for example hydrogen, an alkyl group, Lewis acids, or the like, such materials being known in the art.

The $G^i$ group is the grafting component formed by the reaction of the living end, or a derivative of the living end, of the $i^{th}$ generation oligomer with the reactive groups of the (i-1) generation material. Thus, an anionic oligomer may be reacted directly with an electrophilic precursor generation, or it may be terminated by, for example, a halogen such as chlorine, bromine, or iodine, to create an electrophilic end group for grafting to a nucleophilic precursor. Similarly, a cationic oligomer may be reacted directly with a nucleophilic precursor generation, or terminated with, for example, water, hydrogen sulfide, or an amine to give a nucleophilic end group for reaction with an electrophilic precursor.

Figure 26:
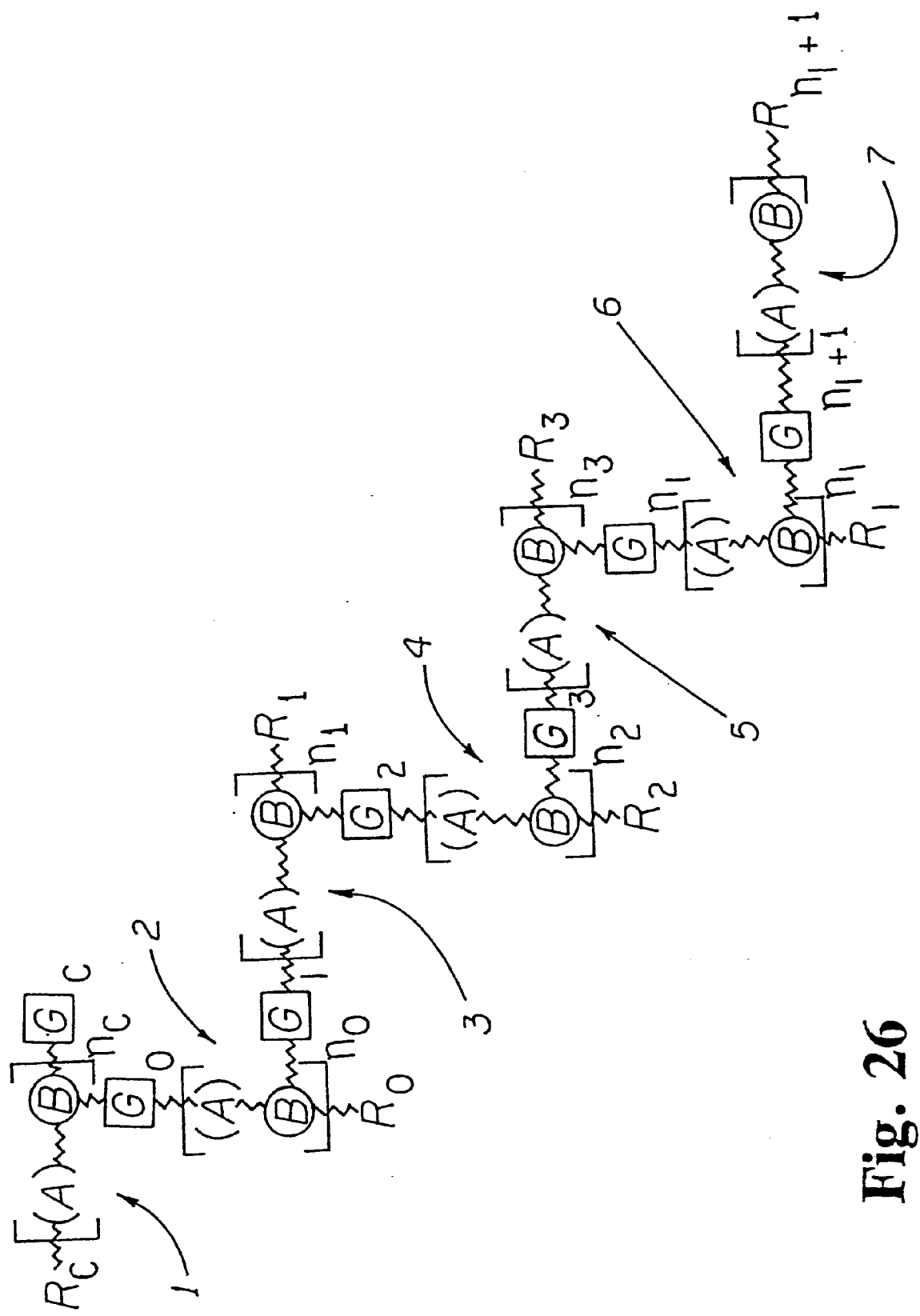
FIG. 26 is a schematic in two dimensions of a polymer configuration of the polymers of the instant invention wherein 1 is the initiator core (initiator core molecule)

As illustrated in FIG. 26, the core may itself be a polymer having the formula $R^c$-$\{(A^c)—(B^c)\}_n {}^c G^c$. In the case of $G^c$, the "graft" is to a monofunctional molecule, which may be as simple as quenching the active end with a proton or hydroxide, as would be the case with normal termination of ionic oligomers with water, or trapping with a specific molecule in order to introduce a single desired functional group to the molecule. Other telechelic groups suitable for grafting purposes may be found in Goethals, "Telecheic Polymers: Synthesis and Applications," CRC Press (1989).

The oligomeric and polymeric segments of these materials can be homopolymers or copolymers, it being understood that the formulae herein represent bonding of the grafting G groups to either segment A, if it is present, or to segment B, and it being further understood that the grafting to any A segment is at the terminal end of the molecule, any other segment A grafting would result in the potential for crosslinking the polymers. Each A segment can be monomeric or, oligomers or polymers formed from polymerizable monomers, the only condition being that the said monomers, oligomers and polymers must be capable of withstanding the conditions required for preparation of subsequent graft junctures. As illustrated in the formulae, the bond from G to the next generation is indicated by a vertical line about halfway between the A segments and the B segments to illustrate that G can be bonded to either A, if it is present, or to B, which is always present in the molecule.

An example of a G group that fits this description would be a urea formed by the reaction of an isocyanate with an amine group. This is formed by the activation of the amines of a poly(vinyl amine) segment with phosgene to create a polyisocyanate precursor molecule which, then, is reacted with an amine terminated poly(vinyl acetamide). The same G group can be formed by treating the poly(vinyl acetamide) with phosgene to form the telechelic oligomer with isocyanate end group, followed by reaction with the poly(vinyl amine) precursor molecule.

An example using the A group bonded to the G group would be the use of a copolymer of ethyl oxazoline and ethylene oxide. The hydroxyl group on the oxyethylene is the terminal group on the reactive oligomer segment. Activation of the hydroxyl group with phosgene gives a chloroformate which is reacted with the amine of poly(ethyleneimine) segment on the precursor generation to form a urethane. Thus, the A group of the reactive oligomer is the "unreactive" oxyethylene and the B group is the masked iminoethylene, N-propionyl iminoethylene.

The range of possible G groups is limited only by the types of coupling reactions that are possible. In addition to ureas and urethanes, imide, thiourea, thiocarbamate, and anhydride linkages are readily available from similar reagents. Precursor molecules containing olefins that result from polymerization or copolymerization of butadiene or ring opening metathesis polymerization of cyclic olefins can be activated by halogenation for subsequent reaction with a nucleophilic end group, or reacted directly with mercaptans via radical addition, or be coupled with a silane end group via catalyzed hydrosilylation methods. Ether and ester linkages can be derived from hydroxyl groups on either the precursor molecule or the reactive oligomer end group.

Segments of A include for example, $—CH_2CH_2—$, $—CH_2CH=CHCH_2—$, $—CH_2C(CH_3)_2—$, $—CH_2CH(CN)—$,

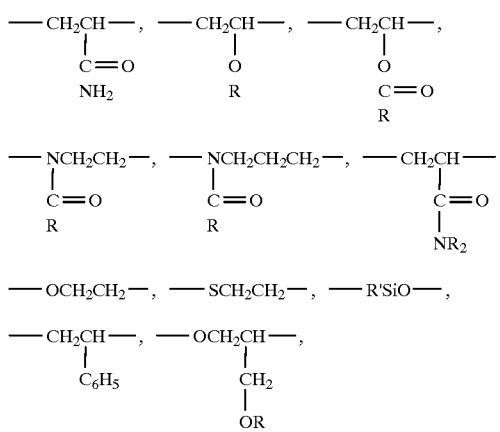

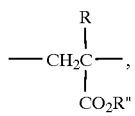

where R' is an alkyl group, aryls, arylalkyl, hydrogen, or carboalkoxy and R is an alkyl group, aryls, or hydrogen;

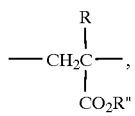

wherein R has the same meaning as set forth above, and wherein R" can be an alkyl group.

Preferred as A segments are —CH₂CH₂—,

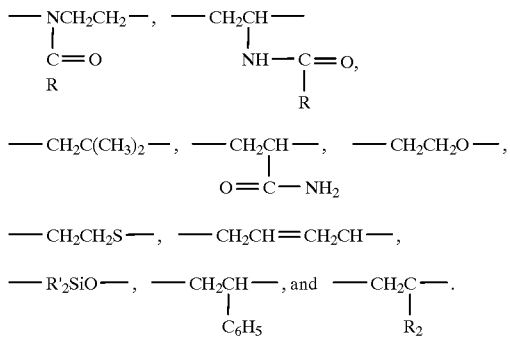

Most preferred are the A segments

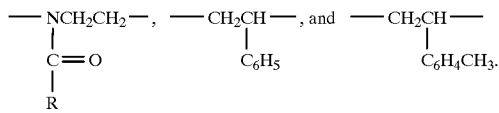

Examples of the B segment can be monomers, or oligomers or polymers formed from polymerizable monomers, wherein said monomers, oligomers and polymers must be capable of withstanding the conditions required for preparation of a graft polymer and further, the B segments must contain at least one unit which is nucleophilic or electrophilic in character.

The groups B contain the reactive sites to which the oligomers may be grafted. Indeed, there are embodiments in which the only difference between A and B groups is that by definition, the A or B group from a succeeding generation branch is grafted to the "B" group. The A groups have the same reactive sites, but they do not get grafted to.

In many cases, these B groups may need to be present in latent or masked form if they would otherwise be incompatible with the oligomerization process. For example, polymerization of aziridine leads to randomly branched polyethyleneimine oligomers which are not useful for this invention because the secondary amines formed are also reactive under the polymerization conditions. Thus it is difficult to control the interior void size, grafting density, size, shape, and nature of surface groups. Oxazoline polymerization leads to linear polyethyleneimine in a protected form, and the secondary amines can be unmasked for grafting by hydrolysis. For vinyl acetate oligomerizations, hydroxyl groups intended for use as future graft sites would need to be masked as, for example, esters to ensure polymerization. Latent reactive sites can then be formed by hydrolyzing the ester groups of the polymerized vinyl acetate into alcohol groups.

Thus, B as a nucleophile can be selected from such groups as

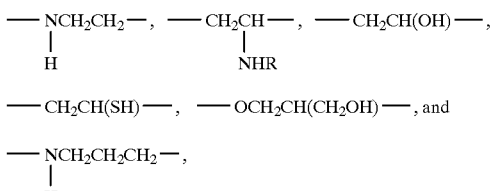

while B as an electrophile can be selected from such groups as

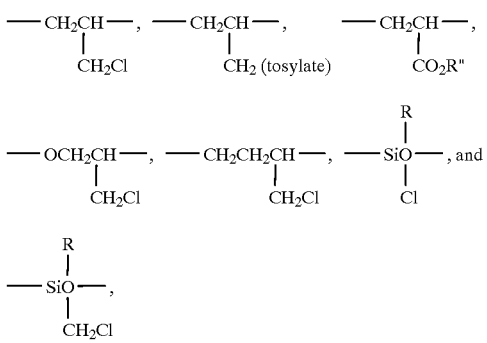

wherein R and R" have the meanings set forth above.

It should be understood that homopolymers consist of only the B segment, while copolymers can be had by combining the B segments with the A segments. Copolymers can also be prepared by using different monomers for the B segment of different generations, for example $B^1$ being different from $B^2$. There must be at least one B segment and therefore the ratio of A segments to B segments ranges from 0 to 1 to 100 to 1.

The core may or may not be produced by "living" polymerization, utilizing "living polymers" or "living oligomers," which oligomers and/or polymers are generally known to those skilled in the art. "Living systems" are preferred in order to control polydispersity of the hyper comb-branched polymers. Using specific chemistry, this is illustrated by reference to "Polymeric Amines And Ammonium Salts," edited by E. J. Goethals, Pergamon Press, (1980), with particular reference to pages 55 et seq. wherein there is taught one method of producing living polymers in a paper entitled "Linear Polyalkylenimines," Saegusa, T. and Kobayashi, S.

Using the example of Saegusa, page 58, one can observe that an initiator such as methyl iodide is first reacted with an oxazoline in the following sequence to give an oligomeric "living oligomer" having, in this case, two protected reactive sites designated as lines and the polymerization mechanism has been determined to be cationic, producing a "living polymer." This allows the preparation of polymer samples with well defined

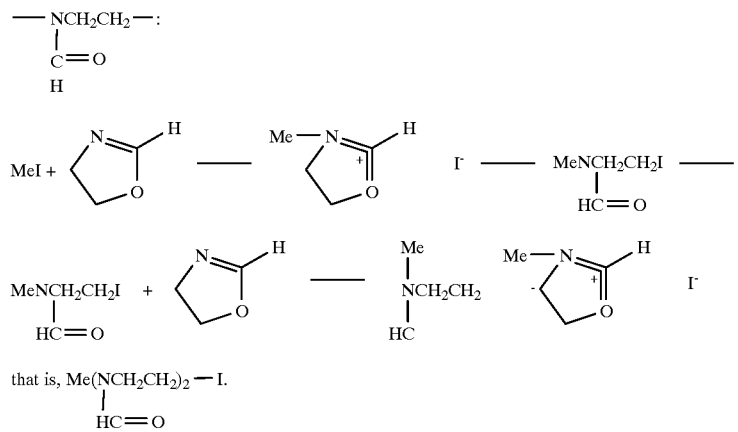

that is, Me(NCH₂CH₂)₂ — I.
            |
          HC=O

Referring to FIG. 26, the initiator core in the specific case described just above would be shown in FIG. 26 as $R^c(B^c)_{nc} G^c$; where $R^c$ is methyl and $G^c$ is as described above.

Reaction sequences are then chosen to deprotect the nitrogen groups so that each of the two reactive sites adds a reactant possessing its own, new reactive site, or sites, which introduces multiplicity, to obtain a comb polymer —$\{(A°)$—$(B°)\}_{no}$—$R°$ of generation 0 (see FIG. 1). As can be observed from the reaction sequence set forth above, this process requires that protection-deprotection strategies are used to ensure that the reactant reacts with all reactive ($B^c$) sites, but does not react any (B°) sites. Protection-deprotection strategies are generally known to those skilled in the art and great detail does not have to be set forth herein. Suffice it to suggest that the living oligomer set forth above has the protective group

on each nitrogen of the oligomer whereupon the oligomer is then hydrolyzed with an acid to give polymeric units having reactive amine groups i.e.

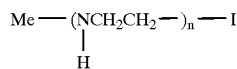

which are then used as the reactive sites to form the next generation, it being understood that the reactive sites of the polymer being grafted to the amine groups are protected before this reaction takes place, and that they too are hydrolyzed after the grafting reaction to give additional reactive sites for the next generation of branching. Additional iterative sequences involving addition of new reactants having reactive sites is then undertaken in order to add branches onto branches to form the poly-branched polymer of this invention until the polymers will not form due to steric hinderance referred to as dense packing.

One of the processes used to prepare hyper comb-branched polymers used in this invention relies on the polymerization of 2-ethyl-2-oxazoline. Methyl p-toluenesulfonate has been shown to polymerize oxazomolecular weight and low polydispersity. The end of the growing polymer chain contains an oxazolinium ion as disclosed above, that can be terminated or quenched by a variety of nucleophiles. For example, to graft the living poly(2-ethyl-2-oxazoline) chains during the first reaction step, the living chain ends are terminated with the secondary amine groups contained on linear poly(ethyleneimine) (LPEI). After grafting onto the linear poly(ethyleneimine) has been accomplished, hydrolysis of the poly(2-ethyl-2-oxazoline) grafts will generate poly(ethyleneimine) branches. This allows further living poly(2-ethyl-2-oxazoline) chains to be grafted onto the poly(ethyleneimine) branches. Repetition of the grafting and hydrolysis forms the inventive polymers with the structures shown herein.

FIGS. 27 and 28 and Examples EE and FF below illustrate branching "0" generation branches onto cores comprising ring compounds and dendrimers respectively, wherein "dendrimer" has the same or similar meaning as that used by Tomalia et al., in Angewandte Chemie, 29/2 (1990), pages 138 to 175. In FIG. 27, branches which can be generated in the manner described above are attached to the four nitrogens in the ring compound 1,4,7,10-tetraazacyclododecane (cyclen), much as they are grafted to the nitrogens of a linear polyethyleneimine core molecule as discussed above. First generation branches are then grafted upon the "0" generation branches, second generation branches are grafted upon the first generation branches, etc. as discussed above.

In FIG. 28, "0" generation branches are grafted to the surface nitrogens of a hyper-terminal-branched or dendrimer core molecule, specifically, a second generation polyethyleneamine. At the generation 2 level (designating the first generation as generation 0), such hyper-terminally-branched molecules are typically referred to as "dendrimers." Hyper-terminal-branched or dendrimer cores can be prepared in various manners known to those skilled in the art including without limitation by the techniques disclosed in U.S. Pat. Nos. 4,507,466 entitled "DENSE STAR POLYMER BRANCHES HAVING CORE, CORE BRANCHES, TERMINAL GROUPS," 4,558,120 entitled "DENSE STAR POLYMER," 4,568,737 entitled "DENSE STAR POLYMERS AND DENDRIMER," 4,587,329 entitled "DENSE STAR POLYMER HAVING TWO-DIMENSIONAL MOLECULAR DIAMETER," 4,631,337 entitled "HYDROLYTICALLY-STABLE DENSE STAR POLYAMINE," 4,737,550 entitled "BRIDGED DENSE STAR POLYMER," 4,599,400 entitled "STAR/COMB-BRANCH POLYAMIDE," 4,690,985 entitled "STAR/COMB-BRANCHED POLYAMINE," 4,694,064 entitled "ROD-SHAPED DENDRIMER," and 4,857,599 entitled "MODIFIED DENSE STAR POLYMERS." Similarly, any of the dendrimer molecules described in said patents could be used as the hyper-branched dendrimer core to which oligomer branches are grafted in reiterative fashion in accordance with the present invention. One need only develop an appropriate strategy for attaching the oligomer branches to the surface moieties of such hyper-branched cores, and various alternatives will be apparent to those of ordinary skill in the art.

For purposes of clarifying terminology, it should be noted that the hyper-terminal-branched core molecule disclosed in FIG. 28 and in Example FF, and those disclosed in the United States patents discussed above are built by reiterative terminal branching rather than reiterative comb-branching. That is to say, one attaches subsequent generation branches to the terminal moieties of a previous generation, thus limiting the degree of branching to the functionality of the previous generation terminal moiety, which would typically be two or three. In contrast by branching oligomers upon prior generation oligomer branches in accordance with the present invention, one can dramatically increase the degree of branching from generation to generation, and indeed can vary the degree of branching from generation to generation.

In another process, the non-crosslinked poly-branched polymers, or hyper comb-branched polymers, are produced in a remarkably low number of iterations by utilizing a particular combination of process parameters and reactants having certain characteristics. It has been surprisingly discovered that hyper comb-branched polymers having a molecular weight of about 1 million and up to about 10 million or even higher can be produced in only several reaction iterations by this preferred embodiment process. A hyper comb-branched polymer product having a molecular weight exceeding 10 million was formed in only 4 iterations from a core of linear PEI 20, and side chains of PEOX 10 for the first iteration and PEOX 100 for the next 3 iterations, by the preferred embodiment process described below. It is contemplated that hyper comb-branched polymers having a molecular weight ranging from about 10 million to about 50 million could be produced in about 4 iterations. It is further contemplated that even higher molecular weight products could be formed such as products having a molecular weight of about 100 million or more by continuing the iterations. Such remarkably high molecular weight polymers are produced in a surprisingly few number of iterations primarily by utilizing longer side chains, a particular grafting ratio, shorter reaction time periods, and utilizing a proton trap to increase grafting yields and prevent chain scission of the comb-branched intermediates and resulting hyper comb-branched polymer product. In another aspect of the process, a novel separation technique is provided for separating a hyper comb-branched polymer product from a reaction mixture, that is both economical and rapid.

The present inventors have discovered that grafting yields may be significantly increased by utilizing a particular grafting ratio of living chain ends to secondary amines, and in some instances, by also employing a proton scavenger during grafting operations. Prior to the present discovery, when producing comb-branched polymers from PEI cores and PEOX 5 to PEOX 10 as grafting chains at a grafting ratio of 0.3 living chain ends per secondary amine, grafting yields typically ranged from about 10% to about 15%. In the present preferred process, it is preferred to utilizing a grafting ratio of from about 0.8 to about 1.2 living chain ends per secondary amine, and most preferred to utilizing a grafting ratio of about 1:1 of living chain ends to secondary amines. These grafting ratios result in significantly improved grafting yields.

At these grafting ratios, i.e. about 0.8 to about 1.2:1, it has been found that it is also beneficial to utilize a proton scavenger during grafting to trap or scavenge protons which are generated during grafting, such as when a living PEOX chain is grafted onto a secondary amine such as PEI. Without such scavengers, expelled protons are transferred to basic secondary amine sites along the PEI polymer backbone, thereby blocking and thus rendering those sites inaccessible for further grafting. In the preferred embodiment process, the use of a proton scavenger and a grafting ratio of about 1:1 has been found to significantly increase grafting efficiency, such as up to about 75% to 95% when grafting PEOX 5 or PEOX 10 branches onto a PEI core.

Proton scavengers may comprise nearly any suitable base that is compatible with the core and side chain reactants. A preferred proton scavenger for use when grafting PEOX chains onto PEI is a relatively hindered, tertiary amine such as i-Pr$_2$NEt. However, it is contemplated that a wide array of suitable bases could be utilized instead of, or in addition to i-Pr$_2$NEt, such as triisobutylamine, triisooctylamine and triethylamine. The proton scavenger is preferably utilized in the grafting mixture in a concentration of from at least about 1 to about 2 equivalents of the proton scavenger for every living or reactive chain end. It is envisioned that even higher ratios may be utilized in certain instances.

As previously noted, the remarkably high molecular weight polymeric products are produced in a surprisingly few number of iterations by increasing grafting yield, and by preventing chain scission of the comb-branched intermediates and resulting hyper comb-branched polymer products. In the case of utilizing PEOX and PEI to produce a hyper comb-branched polymer, chain scission often occurs when there exists an excess of chain ends to secondary amines in the reaction environment. An excess of chain ends to secondary amines promotes the formation of quaternary amines along the polymer backbone, which readily undergo Hofmann degradation to produce undesirable lower molecular weight fragments upon heating.

It has been discovered that chain scission may be essentially prevented or significantly minimized by employing one or more of the following practices: (a) utilizing shorter reaction periods, (b) utilizing relatively long chains for grafting onto polymer backbones, (c) ensuring that NaOH or other salts are completely removed, or nearly so, from the reaction mixture(s) throughout the various stages of the process, and (d) ensuring that the resulting hyper comb-branched product is maintained at relatively low temperatures and not exposed to high temperatures. It is preferred to employ all of these practices to prevent chain scission, and most preferred to employ all of these practices in conjunction with utilizing the previously described grafting ratios and proton scavenger during grafting operations to increase grafting yields.

Shorter reaction periods are utilized for both polymerization of the reactants, e.g. core and branches, and grafting operations in the preferred embodiment process since shorter reaction periods have been found to reduce the tendency for quaternary amines to be formed. Quaternary amines, as previously noted, are prone to undergo Hofmann degradation and thereby cause chain scission. When forming PEOX side chains from PEOX 10 or PEOX 20, for later use in preparing hyper comb-branched polymers, it is preferred to utilize a time period of less than about 5 hours for the polymerization of PEOX. When forming PEOX side chains from PEOX 100, longer time periods may be required such as up to about 10 hours. It is particularly preferred to employ relatively short time periods during grafting operations, such as a grafting reaction time of less than about 1 hour for grafting polymerized PEOX chains onto a PEI core.

In addition to forming side chains from PEOX, it is possible to utilize a wide array of monomer units such as, but not limited to, any 2-4-, or 5-substituted oxazoline;

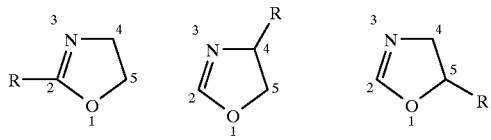

any 2-unsubstituted 5,6-dihydro-4H-1,3-oxazines;

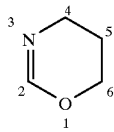

any 2-substituted 5,6-dihydro-4H-1,3-oxazines;

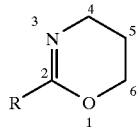

or any block copolymers containing 5,6-dihydro-4H-1,3-oxazines and 2-alkyloxazolines. Hyper comb-branched polypropyleneimine polymer obtained by hydrolysis of poly (5,6-dihydro-4H-1,3-oxazines), both 2-substituted and 2-unsubstituted, were found to exhibit a relatively high degree of thermal stability as compared to those having PEI side chains.

The tendency for chain scission is further reduced by utilizing relatively long chains for grafting onto a polymer backbone. Once a long side chain is grafted onto a secondary amine to generate a tertiary amine site along the polymer backbone, it is nearly impossible to introduce another chain, particularly another long chain, at this tertiary amine site due to steric inhibition. In the case of forming hyper comb-branched polymers from PEOX and PEI, it has been discovered that the preferred length for PEOX side chains or branches are at least about 50 monomer units, and most preferably at least about 100 monomer units.

In another embodiment, relatively short chains are utilized during the early stages in forming the hyper comb-branched product, i.e., generation 0, (G0) and relatively long side chains are utilized during later stages, i.e., generations 1 (G1) and above. This practice has been found to increase interior branching density, and reduce the previously described tendency for chain scission to occur at higher generations.

Chain scission may also occur after initial formation of the poly-branched polymer or hyper comb-branched polymer, such as during or after neutralization of the hydrolyzed polymer product. After formation of the comb-branched polymer product and addition of acid to hydrolyze the product, the polymer product is neutralized and separated from the reaction mixture by adding base to form an oily layer containing the polymer product. This is typically accomplished by adding a base such as NaOH followed by heating until an oily layer separates from the mixture, that layer containing the high molecular weight product. The oily layer is then cooled to harden or solidify it, wherein it can be readily removed. It has been discovered that after neutralization with NaOH, the PEI moieties in the polymer product tend to chelate the sodium cations, thereby freeing hydroxyl ions and increasing the pH of the environment, and further promoting Hofmann degradation of any quaternary amines present upon heating, which in turn leads to chain scission. Additionally, unwanted amounts of NaOH or other salts may contaminate the reactants used in forming the polymer product, such as linear PEI. Such contamination can later promote chain scission. Removal of NaOH or other salts from the poly-branched polymer, and/or from the components used to form such product, has been discovered to reduce the tendency of chain scission of the poly-branched or hyper comb-branched polymer. NaOH or other salts may be removed from the reaction mixture at various points of the process by a wide variety of techniques such as exhaustive washing with water of precipitated polymer product or of the reactants used to form the polymer product which are believed to contain NaOH, and then dissolving the polymer product in toluene, in which NaOH is insoluble, heating to remove water by azeotropic distillation, then filtering or otherwise separating the hot polymer product from the NaOH and/or other salts. The various points of the process in which it is desirable to remove NaOH or any other salts include the stage in which the reactants are polymerized to form chains for subsequent grafting onto the polymer core or backbone, and the stage in which the grafting occurs.

Chain scission is also minimized in accordance with the preferred embodiment process by not exposing the resulting poly-branched or hyper comb-branched polymer product to temperatures that are significantly above room temperature, such as when drying by ovens in which case, temperatures of 100° C. or more are often reached. Conventional drying procedures in which PEI polymer was dried at 80° C. in an oil bath and under vacuum overnight were found to degrade the comb-branched polymer into undesirable numerous smaller fragments. Thus, it is preferred that PEI poly-branched or hyper comb-branched polymer product is dried at temperatures less than about 60° C., and it is most preferred that the PEI product be stored at room temperatures, i.e. about 20° C. It has been found that PEOX-PEI comb-branched polymers exhibit greater thermal stability than PEI comb-branched polymers. Thus, it is preferred to store hyper comb-branched polymers in the PEOX-PEI stage and hydrolyze the polymers to PEI hyper comb-branched polymers prior to use.

In another aspect of the process, a novel separation technique is provided for separating a poly-branched or hyper comb-branched polymer product from a reaction mixture containing lower molecular weight products that is both economical and rapid. Currently known techniques for separating high molecular weight, highly branched polymers from reaction mixtures generally involve some type of ultrafiltration process. Ultrafiltration, although satisfactory in many respects, is undesirable in view of the relative high cost of ultrafiltration equipment and the inefficiencies associated with separating high molecular weight products from undesired low molecular weight products. The present inventors have discovered a separation technique, whereby ultrafiltration is avoided and the polymer product is separated by a polymer refractionation technique.

The preferred polymer refractionation technique is performed by separation of hyper comb-branched polymer product from a reaction mixture comprising the product and unwanted lower molecular weight components at the PEOX-PEI stage, by a first addition of an alcohol solvent in which both high molecular weight and low molecular weight products are soluble, and a second incremental addition of a poor solvent in which the high molecular weight product is less soluble than the unwanted low molecular components. Addition of the poor solvent to the alcohol and dissolved components causes the high molecular weight polymer product to precipitate from solution. Examples of suitable poor solvents include, but are not limited to, diethyl ether or other ether-based solvents and hexane.

An example of the preferred refractionation technique is as follows. An alcohol solvent such as methanol is added to the reaction mixture, until all of the components in the mixture, including unwanted low molecular weight components and the high molecular weight polymer product, are dissolved and are in solution. Then, a poor solvent such as diethyl ether, is incrementally added to preferentially precipitate the desired high molecular weight components from the alcohol phase containing the low molecular weight products. Poor solvent is added until all, or substantially all, of the high molecular weight product is in the precipitate. Periodically, the resulting oil sludge bottom product, i.e. precipitate, and/or top layer containing the dissolved low molecular weight products are analyzed for the presence of the high molecular weight polymer product. Analysis may be performed by SEC (size exclusion chromatography) methods. Once the high molecular weight polymer product no longer precipitates from the resulting mixture of alcohol solvent, poor solvent, and low molecular weight components, and thus is in the precipitate, addition of the poor solvent is halted. The mixture remaining above the precipitate and containing the low molecular weight product, is then removed. The high molecular weight poly-branched or hyper comb-branched product remains in the bottom precipitate layer and can be redissolved in water and subsequently dried by lyophilization.

The present invention also provides hyper comb-branched polymers that are joined to one another by crosslinking or by other types of bridging. Very large macromolecules can also be formed without cross-linking or bridging between polymer molecules. Either type of macromolecule can be suitable as a carrier, and are all included within the class of hyper comb-branched polymers described herein.

The Conjugates

The conjugates of the present invention comprise the previously described hyper comb-branched polymers conjugated with one or more carried materials. The preferred embodiment conjugates have the formula:

$$H_v\text{—}M_b$$

wherein
H is a hyper comb-branched polymer as described herein that may comprise one or more functional groups disposed generally about the periphery of the polymer;
M is a carried material;
v is an integer of 1 or greater; and
b is an integer of 1 or greater.

The most preferred hyper comb-branched polymer conjugates are those in which the carried material M, may be any one or more of a 1) diagnostic agent, 2) agricultural agent, 3) bioactive agent, 4) industrial agent, 5) environmental agent, and 6) consumer product agent. Examples of diagnostic agents include, but are not limited to, metal ions, radioactive drugs, radioactive tracers, radio-opaques, radionuclides, signal generators, signal reflectors, signal absorbers, diagnostic opacifier agents, fluorescent moieties, and dye moieties. Agricultural agents may include, but are not limited to, agricultural materials, pheromones, pesticides, herbicides, and bioactive agents suited for agricultural uses. Examples of bioactive agents include, but are not limited to, pharmaceutical agents or drugs, pharmaceutical intermediaries, radioprotective agents, toxins, antibodies or fragments thereof, hormones, biological response modifiers, scavenging agents, imuno-potentiating agents, genetic materials, antigens, and polypeptides. Examples of industrial agents include, but are not limited to, scavenging agents, agents for material modifiers such as adhesives and colloid dispersants, stabilizing agents, and chromophores. Examples of environmental agents include, but are not limited to, radioprotective agents, scavenging agents, pollutants, and agents for agricultural materials. Examples of consumer product agents include, but are not limited to, fragrance moieties, stabilizing agents, material modifiers and chromophores.

The present invention also provides derivatives and variations of the preferred embodiment conjugates. The preferred embodiment conjugate variations include target directors and have the formula:

$$H_v\text{—}M_b\text{—}T_z$$

where T is a target director and z is an integer of 1 or greater. Examples of T include agents that target the carried material, M, such as a bioactive agent, to, for example, a plant or pest or a particular factor in a target organism. Other examples of target directors include, but are not limited to, entities which when used in the conjugates of the present invention result in at least a portion of the hyper comb-branched conjugate being delivered to a desired target, for example, a protein, lipid, a targeted cell, a targeted organ, antibodies, preferably monoclonal antibodies, antibody fragments, hormones, biological response modifiers, and the like. Target director T includes proteins, antibodies, antibody fragments, saccharides, and oligosaccharides.

The preferred embodiment conjugate derivatives also include derivatives having more than one carried material M', different than the primary conjugated carried material M, and/or target material T, of the formula:

$$T_z\text{—}H_v\text{—}M_b\text{—}M'_a$$

where a is an integer of 1 or more. Examples of M' include all of the previously described agents for M.

Figure 15:
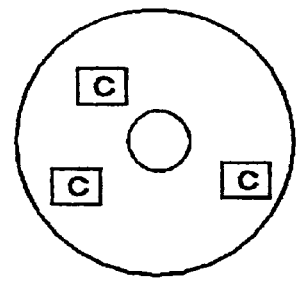
FIG. 15 illustrates a hyper comb-branched polymer conjugate having carried material disposed within the interior of the polymer.
Figure 16:
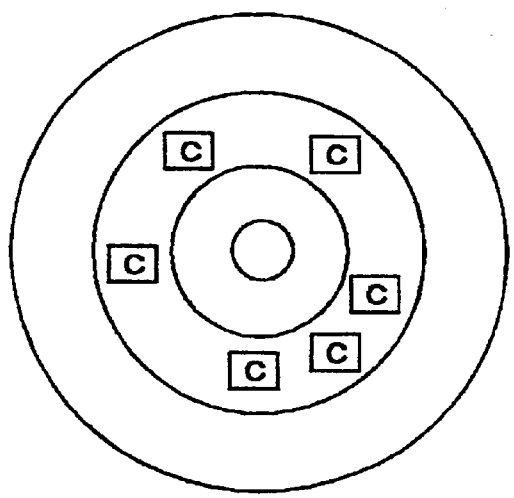
FIG. 16 illustrates a hyper comb-branched polymer conjugate having carried material disposed throughout a particular layer or generation.
Figure 17:
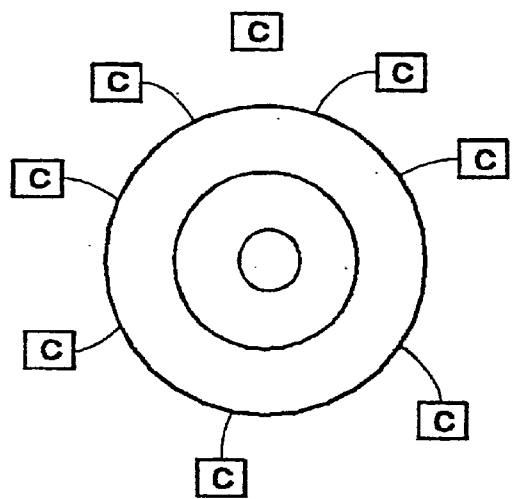
FIG. 17 illustrates a hyper comb-branched polymer conjugate having carried material disposed at the surface of the polymer.

There are numerous ways in which the carried material may be conjugated with the hyper comb-branched polymer. The carried material may be disposed generally within the polymer, such as depicted in FIG. 15. This is accomplished by incorporating the carried material in the core or one or more of the beginning branching generations. Alternatively, or in addition, carried material may be disposed between layers, as illustrated in FIG. 16. Carried material may also be disposed on the surface of the hyper comb-branched polymer, as illustrated in FIG. 17. In this embodiment, the carried material is incorporated in one or more of the latter branching generations. The carried material can also be attached to the outer periphery as a terminal moiety. In all of these embodiments, the carried material may be conjugated with the hyper comb-branched polymers by physically encapsulating or entrapping the carried material within the core of the polymer, dispersing the carried material partially or fully throughout the polymer, or attaching or otherwise linking the carried material to the polymer, whereby the attachment or linkage is by means of covalent bonding, hydrogen bonding, adsorption, absorption, metallic bonding, van der Waals forces, ionic bonding, or any combination thereof.

Moreover, since the size, shape and functional group density of the hyper comb-branched polymers can be precisely controlled, there are numerous other ways in which the carrier material can be conjugated or associated with the polymer. For example, conjugation may be effected by covalent, coulombic, hydrophobic, or chelation type association between the carried materials and entities, typically functional groups, located at or near the surface of the hyper comb-branched polymer. There can be covalent, coulombic, hydrophobic or chelation type association between the carried materials and moieties located within the interior of the hyper comb-branched polymer. The polymer can be prepared to have an interior which is predominantly hollow allowing for physical entrapment of the carried materials within the interior, i.e. void volume, wherein the release of the carried material can optionally be controlled by congesting the surface of the polymer with diffusing controlling moieties.

There may be instances in which it is desirable, or even necessary to control the distance between the hyper comb-branched polymer and the carried material. This can be accomplished by utilizing a spacer group between the polymer and carried material. The preferred lengths for these spacers generally range from about 2 angstroms to about 20 angstroms or higher. Typically, the use of such spacers results in optimization of the reactivity of the conjugate.

As described below, there are numerous applications for hyper comb-branched polymers conjugated with carried materials. Examples of such applications include, but are not limited to, protein conjugation, drug encapsulation, signal amplification, metal chelation, and gene transfection.

Protein Conjugation

Figure 18:
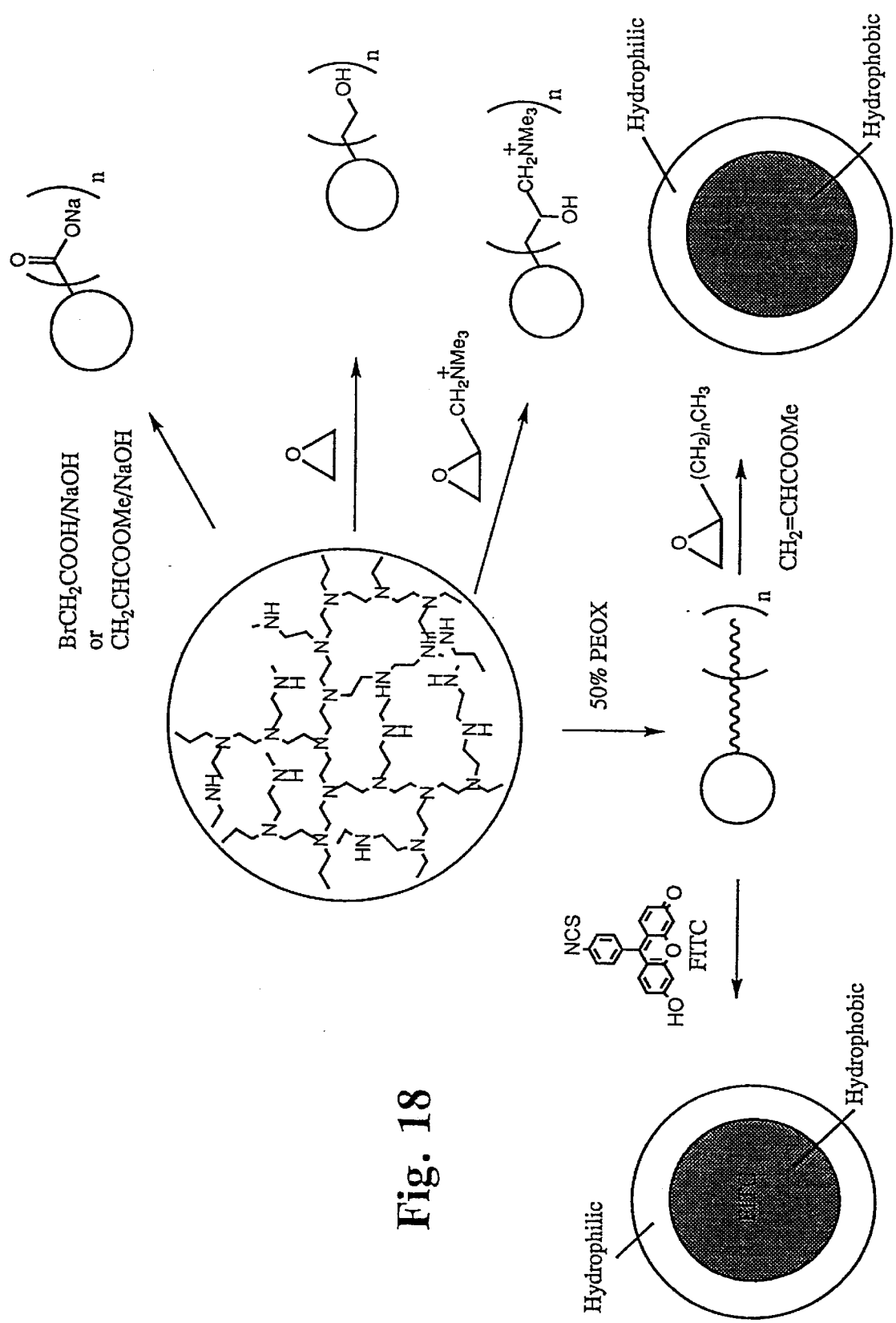
FIG. 18 illustrates several process schemes for modifying hyper comb-branched polymers.
Figure 19:
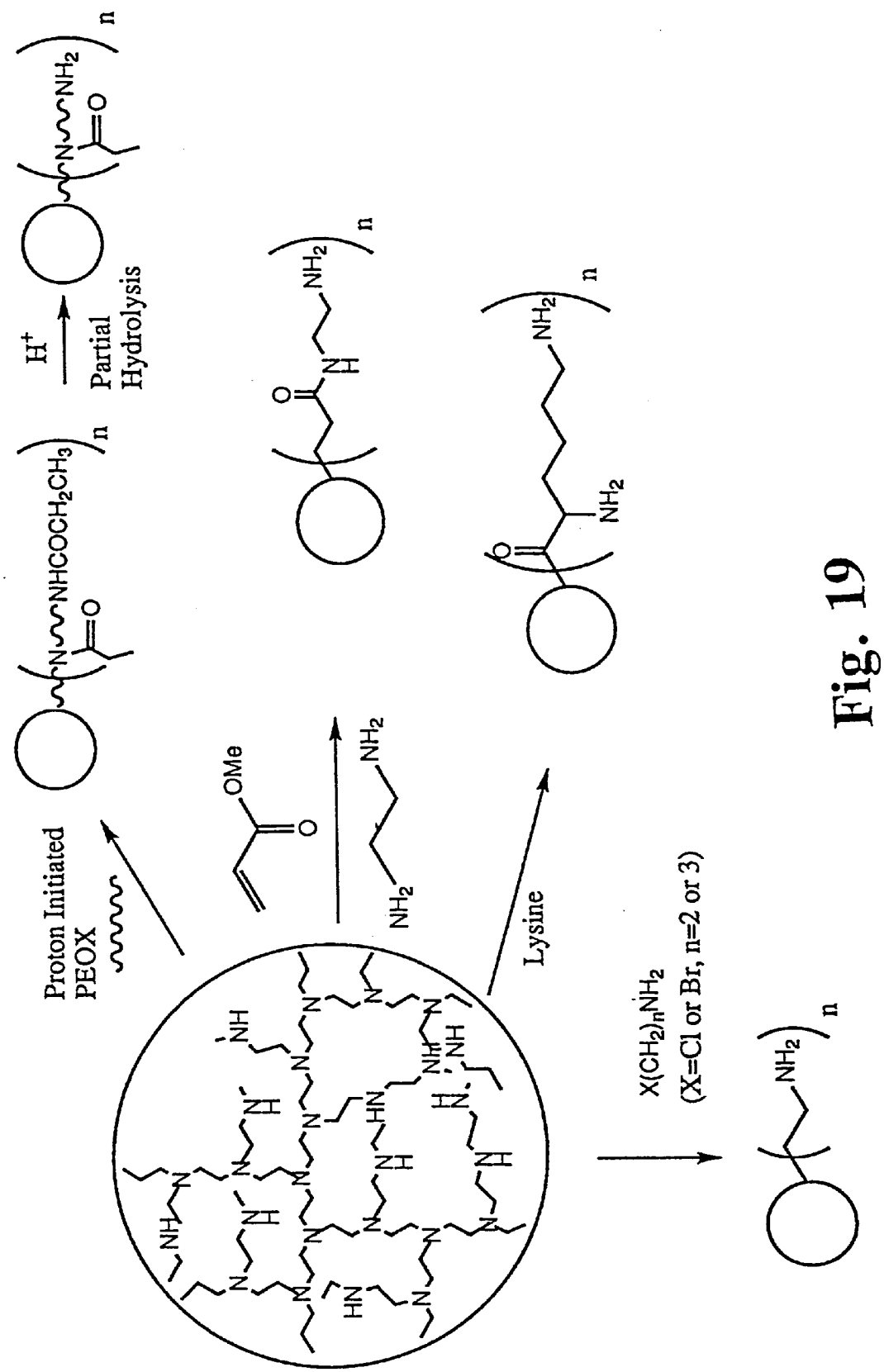
FIG. 19 illustrates several additional process schemes for modifying hyper comb-branched polymers.

Generally, the stability of proteins in solution is very poor. The hyper comb-branched polymers described herein can conjugate proteins and thereby stabilize the protein by minimizing structural transformation of the protein such as refolding and maintain protein activity. As described in Examples 1–8 set forth below, water soluble hyper comb-branched polymers with PEOX, COOH, COONa, and —NH$_2$ surfaces were obtained by grafting water soluble polymers (i.e. PEOX) or small organic molecules onto the outermost generations of hyper comb-branched polymers, as illustrated in FIGS. 18 and 19. In all cases, hyper comb-branched polymers with superior water solubility as compared to that of unmodified hyper comb-branched PEI polymers were obtained. Since both NH$_2$ and COOH are naturally occurring functionalities in proteins and peptides, the bioconjugation of such hyper comb-branched polymers can be achieved under physiological conditions without denaturing the proteins.

Figure 20:
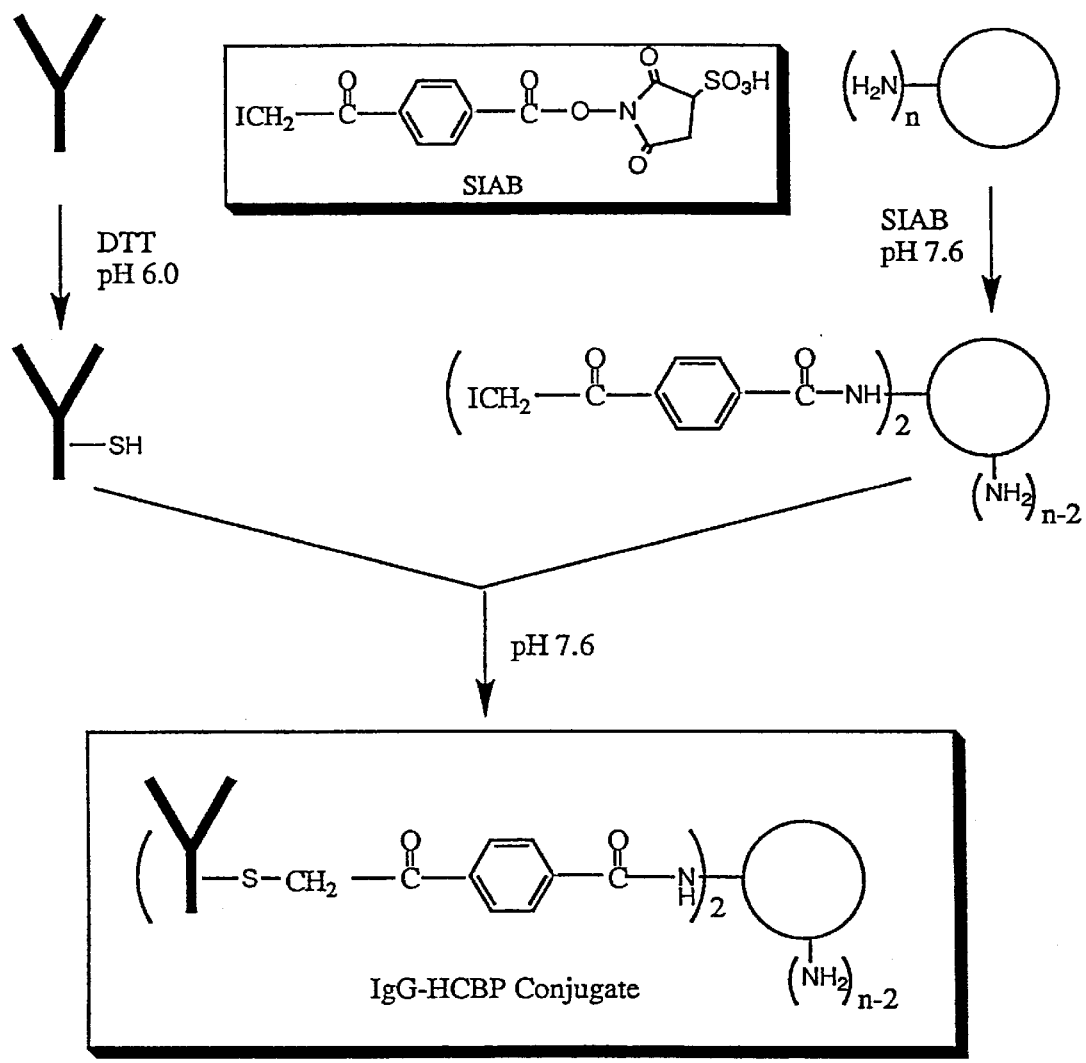
FIG. 20 illustrates a process for producing a monoclonal antibody bioconjugate.

As described in Example 9 set forth below, and illustrated in FIG. 20, a hyper comb-branched polymer was first derivatized with sulfo-SIAB, a reagent, to generate an iodoacetyl modified hyper comb-branched polymer. The resulting polymer product was then reacted with sulfhydryl functionalized monoclonal antibody formed by the antibody with reducing dithiothreitol (DTT) at pH 7.6. The conjugate was characterized by UV radiation at 280 nm, and the activity of the antibody after conjugation was maintained as indicated by creatin kinase monoclonal antibody (CKMB) assay. This monoclonal antibody bioconjugate could be utilized in diagnostic assays and targeted drug deliveries both in vitro and in vivo.

It is envisioned that a wide array of enzymes and proteins can be stabilized by conjugating such with the hyper comb-branched polymers described herein. Examples of such enzymes include, but are not limited to, glutamate pyruvate transaminase (GTP), alkaline phosphatase, acid phosphatase, glutamate oxalacetate transaminase (GOT), creatinine kinase, and lactate dehydrogenase. Examples of such proteins include, but are not limited to, troponin, ferritin, prolactin, gastrin, and calcitonin.

EXAMPLE 1

Synthesis of Hyper Comb-Branched Polymers [HCB G0]

The synthesis of PEOX100-g-PEI20 is provided as a general procedure for the preparation of hyper comb-branched PEOX-PEI and PEI polymers. A mixture of MeOTs (0.1845 g, 0.9906 mmol) in 150 ml of toluene was azeotroped to remove water with a distillation head under Ar for 10 minutes. After cooling to about 90° C., 2-ethyloxazoline (10 ml, 99.06 mmol) was cannulated in and the mixture was allowed to reflux for 5–10 hours. To this mixture was added morpholine terminated LPEI 20 (49.5 mg, 0.9906 mmol of NH), which was dried by azeotropic distillation from toluene, followed by immediate addition of i-Pr$_2$NEt (1 to 2 eq.). The mixture was refluxed for 1 hour, and then cooled. The top layer was decanted and the bottom layer (polymer product) was redissolved in methanol, followed by fractionation by methanol/diethyl ether mixture to remove the unreacted monomers, oligomers and catalysts. The entire separation process was monitored by SEC. The purified product was rotary evaporated and lyophilized to produce a hyper comb-branched G0 PEOX-PEI polymer as a white powder. This white powder was further hydrolyzed in 50% H$_2$SO$_4$ at 100° C. and then neutralized by 50% NaOH solution. This solution (pH of about 10 to 11) was heated to boil under N$_2$, and the product (G0 PEI) floated on top as an oil layer. After cooling to room temperature, the top layer became a solid cake on the surface which was subsequently removed and redissolved in 600 ml deionized, boiling water. After slow sedimentation overnight, the white precipitate was filtered by suction funnel. The pure hyper comb-branched PEI polymer was obtained by azeotropic removal of water from a toluene solution of the polymer, followed by a gravity filtration and then rotary evaporation of the toluene at 60° C. Both hyper comb-branched PEOX-PEI and PEI polymers were characterized by size exclusion chromatography (SEC), nuclear magnetic resonance (NMR), thermal gravimetric analysis (TGA), and differential scanning coulimetry (DSC). Other hyper comb-branched polymers with different grafting chain lengths, branched cores, and generations were prepared in a similar manner.

EXAMPLE 2

Functionalization of Hyper Comb-Branched PEI Polymers with 50% PEOX10 [HCB G1 (50% PEOX)]

The reaction procedure is similar to the preparation of hyper comb-branched PEOX-PEI polymers described in Example 1 except the ratio of the living chain end of PEOX10 to NH was 0.5:1.

EXAMPLE 3

Hyper Comb-Branched Polymer-COOMe [HCB G3 (COOMe)]

To a 100 ml round bottom flask containing 1.0256 g of hyper comb-branched G3 PEI polymer was added 4.709 g of methyl acrylate solution in MeOH (50%) at 0° C. The resulting mixture was then diluted with 20 ml MeOH. The mixture was reacted at 37° C. for 24 hours, and then dried by rotary evaporation and $N_2$ bubbling (80% yield). The product was analyzed by NMR.

EXAMPLE 4

Hyper Comb-Branched Polymer-$NH_2$ (PAMAM Modified) [HCB G3 (PAMAM)]

To a 1 L polyethylene jug containing 740 ml ethylene diamine (EDA)/methanol (MeOH) mixture (78 wt. % of EDA) was added ester functionalized hyper comb-branched polymer (from Example 3) at a ratio of EDA/ester of about 300:1. The mixture was allowed to react at −5° C. for 5 days, and the pure product was obtained by rotary evaporation of EDA and MeOH, followed by ultrafiltration with Amicon 10,000 molecular weight cut off membrane. The resulting product was characterized by NMR and SEC (molecular weight of about 29,000, molecular weight distribution of about 1.11). Other generations of hyper comb-branched polymers with such primary amine modifications were prepared in a similar manner.

EXAMPLE 5

Hyper Comb-Branched Polymer-$NH_2$ (Chloroethylamine Modified) [HCB G3 (CEA)]

To a 100 ml round bottom flask containing 0.44 g hyper comb-branched G3 PEI polymer dissolved in 30 ml MeOH was added 0.48 g chloroethylamine hydrochloride (dissolved in 5 ml of MeOH), and 2 eq. of NaOH dissolved in MeOH. The reaction mixture was refluxed at 60° C. for 1 to 3 hours, the solution was filtered and dried by rotary evaporation. The crude product was redissolved in MeOH and precipitated out from the solution by addition to diethyl ether. The pure product was characterized by NMR and SEC (molecular weight of about 35,000). Other generations of hyper comb-branched polymers with such primary amine modifications were prepared in a similar manner.

EXAMPLE 6

Hyper Comb-Branched Polymer-$NH_2$ (Chain Terminal Modified) [HCB G2 ($NH_2$ Terminated)]

A mixture of p-toluenesulfonic acid (0.754 g) in 150 ml of toluene was azeotroped to dryness with a distillation head. To this mixture was added 2-ethyloxazoline (39.28 g), and the mixture was allowed to reflux for 5 to 10 hours. To this mixture was added G1 PEI polymer (0.20 g, molecular weight of about 130,000) dried by azeotropic distillation from toluene, followed by immediate addition of i-$Pr_2$NEt (1 to 2 eq.). The mixture was refluxed for 1 hour, and then cooled to room temperature. The pure product (G2) was obtained by fractionation with a methanol/diethyl ether mixture, and was characterized by NMR, DSC, TGA, and SEC (molecular weight of about 3,900,000, molecular weight distribution of about 1.33).

To a 250 ml round bottom flask containing hyper comb-branched G2 PEOX polymer (5 g in 150 ml of $H_2O$) was added 1 eq. 50% $H_2SO_4$. The mixture was allowed to reflux for 3 hours, and then was neutralized to a pH of from about 10 to about 11. After heating, an oil layer was formed on the bottom and was separated immediately. The pure product (white solid) was dried by rotary evaporation and high vacuum, and was characterized by NMR, DSC, TGA, titration, and SEC (molecular weight of about 2,600,000, molecular weight distribution of about 1.50). Other generations of hyper comb-branched polymers with primary amines at the polymer chain ends were prepared in a similar manner.

EXAMPLE 7

Hyper Comb-Branched Polymer-COOH [HCB G0 (Propionic Acid)]

To a 100 ml round bottom flask containing ester-functionalized hyper comb-branched G0 polymer was added 1N NaOH (about 2 eq.) and water. The reaction mixture was refluxed for 1 to 5 hours. The solution was then cooled and neutralized by 1N HCl until white precipitate was formed (pH about 1). The pure product was obtained by filtration, followed by dryness with vacuum drying (>60% yield).

EXAMPLE 8

Hyper Comb-Branched Polymer-COOH [H CB G0 (Acetic Acid)]

To a 100 ml round bottom flask containing hyper comb-branched G0 PEI polymer in water and MeOH mixture was added bromoacetic acid (1 eq.) and about 2 eq. NaOH. The mixture was refluxed for 6 hours. The solution was cooled and then neutralized by 1 N HCl until a white precipitate was formed. The solution was filtered and the solid was dried in a vacuum oven at 45° C. for 6 hours. The product was analyzed by NMR and SEC.

EXAMPLE 9

Antibody—Hyper Comb-Branched Polymer Conjugate

Iodoacetyl Hyper Comb-branched Polymer

To a test tube containing 1 ml of 10 to 50 mg/ml of hyper comb-branched polymer functionalized with —$NH_2$ terminal groups, in water was added 0.2 ml of 0.5 M sodium phosphate (pH 7.0), and the solution pH adjusted up to 7.6 using 1N HCl. This solution was then added to freshly dissolved sulfo-SIAB (20 mg/ml in water), and gently vortexed. After incubation at 30° C. for one hour (or at room temperature for 2 hours), the pure product was obtained by passing the reaction mixture through a G-25 Sephadex column. The concentration of the polymer was determined using a fluorescamine assay monitored with a fluorimeter and the iodo content was quantified with DTT and 4,4'-dithiodipyridine.

Preparation of protein with SH groups

An anti-CKMB IgG protein was buffer exchanged into a reduction buffer (0.1M sodium phosphate, 5 mM EDTA, (pH 6)) and the resulting concentration was adjusted to 5 mg/ml. To this solution was added a solution of 11.4 mg/ml of DTT equal to ⅕ of the volume of the protein solution. After incubation at 37° C. for one hour, the free sulfhydryl groups were formed and the product was purified from low molecular reagents by a passage through a G-25 Sephadex column. The protein concentration was determined by UV absorption at 280 nm.

Antibody Hyper Comb-Branched Polymer Conjugate

To a test tube was added iodoacetyl modified hyper comb-branched polymer and IgG-SH at a challenge ratio of 3:1 (pH of 7.6, protein concentration of 5 mg/ml). After incubation at 2 to 8° C. for 16 to 24 hours, the reaction was quenched by addition of 20 mg/ml N-ethyl maleimide in dimethyl formamide at 2 to 8% for 2 hours. The pure conjugate was obtained by gel filtration (Ultrogel AcA, Pharmacia Sephadex or Sepharose gels) or by ultrafiltration with YM-100 Amicon Membrane.

Drug Encapsulation

Since drugs, both human and agricultural, are generally hydrophobic, a hydrophobic interior of a hyper comb-branched polymer performs like a well-defined, covalently-fixed micelle. Associating or linking a hydrophobic drug within that region provides a novel mechanism for solubilizing or delivering such drugs.

Interior hydrophobically modified hyper comb-branched polymers can be produced through three general synthetic methods. The first method is to utilize a functionalized hydrophobic, linear or branched polymeric core (i.e. chloroethyl or bromoethyl functionalized linear or branched polystyrene) as an initiator to polymerize 2-ethyloxazoline and form an amphiphilic hyper comb-branched (PS-PEOX) polymer. The second method is to first functionalize hyper comb-branched PEI polymers with an appropriate percentage of linear water soluble polymers. Due to steric effects, the grafting polymeric chains can only react with the readily available exterior secondary amines, thereby shielding the interior secondary amines. The resulting water soluble polymer is then reacted with hydrophobic monomers in the interior to provide an amphiphilic hyper comb-branched polymer. The third approach involves a combination of the above methods, in which an amphiphilic block copolymer is grafted onto a functionalized linear or branched polymeric core. In all three schemes, higher generation hyper comb-branched amphiphilic polymers can be produced by the same iteration steps utilized in the synthesis of hyper comb-branched PEOX and PEI polymers.

As described in Examples 10 and 11, hyper comb-branched polymers having hydrophobic interiors were formed by modifying the interior of exterior-functionalized, water soluble hyper comb-branched polymers with hydrophobic monomers such as epoxy hexane and methyl acrylate. In addition to the NMR evidence, where characteristic resonance of the alkyl chain or ester group could easily be identified, SEC measurements also indicated that the modified hyper comb-branched polymers shrunk in size when dissolved in water after the hydrophobic modification. This is primarily due to the shrinking of the hydrophobic interior.

An interior hydrophobically-modified hyper comb-branched polymer was also obtained through block copolymerization. In this case, homo poly(2-phenyloxazoline) (PPOX) is utilized as a hydrophobic segment, while homo PEOX is utilized as a hydrophilic segment, as depicted in FIG. 21. The block copolymer of PEOX-PPOX is, therefore, an amphiphilic polymer. By grafting such a block copolymer onto a linear or a branched PEI core, a hyper comb-branched polymer with a hydrophobic interior and a hydrophilic exterior can readily be obtained (Example 12). As measured by SEC, the apparent molecular weight of the polymer product increased upon addition of the second monomer. This increase indicates the formation of the desired block copolymer. The size of the hyper comb-branched polymer formed by utilizing block copolymer side chains is, however, smaller than that obtained with homo PEOX side chains, suggesting the formation of the hydrophobic interior.

If the last grafting PEOX side chains are produced with para-toluenesulfonic acid as an initiator, the resulting amphiphilic PEOX HCB polymer can be partially or fully hydrolyzed to generate an amphiphilic PEOX/PEI or PEI HCB polymer with primary amines at the chain ends of the exterior layer. These primary amines can then be utilized to conjugate with targeting moieties such as monoclonal antibodies while the hydrophobic interior is still able to carry a large amount of drugs. If the number of surface functional groups produced by this method is not large enough, the amphiphilic PEOX/PEI or PEI HCB polymer can then be further modified through standard PAMAM dendrimer synthesis techniques (i.e. the addition of methyl acrylate and DEA to generate amphiphilic HCB polymers with more primary amines or carboxylates at the surface).

Since acid hydrolysis of PEOX is much easier than that of PPOX, functional secondary amines can be preferentially formed at the exterior of the hyper comb-branched polymers, while the hydrophobic interior remains intact. The grafting of additional layers of the PEOX-PPOX block copolymers at higher generations can generate hyper comb-branched polymers with a PEOX-PPOX-PEI-PPOX-PEI-... -PEOX multilayered dendritic architecture. The intermediate PEI layers can then be conveniently converted into more hydrophilic layers by reaction with hydrophilic monomers such as ethylene oxide and bromoacetic acid. Thus, a multilayered amphiphilic hyper comb-branched polymer can be prepared by the same iteration steps described in Example 12.

Figure 22:
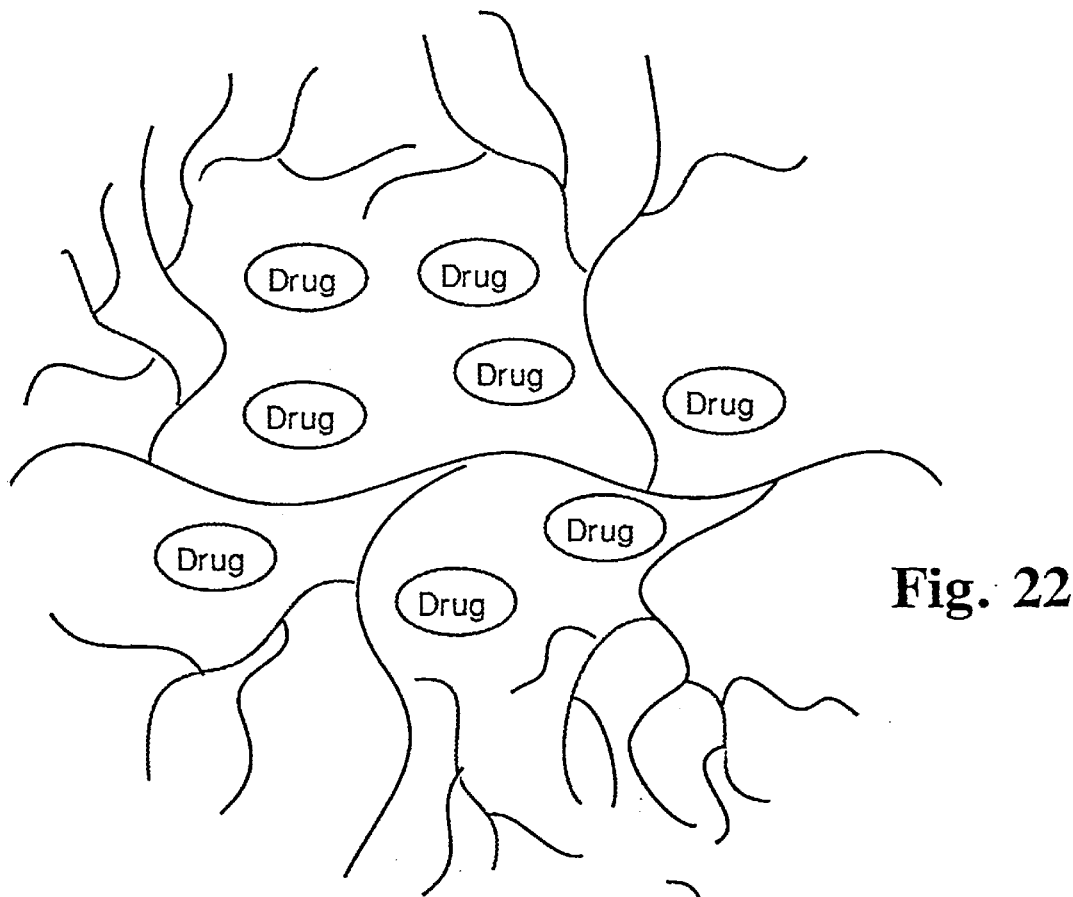
FIG. 22 illustrates a hyper comb-branched polymer conjugate comprising carried drug agents associated in the interior of the polymer.
Figure 23:
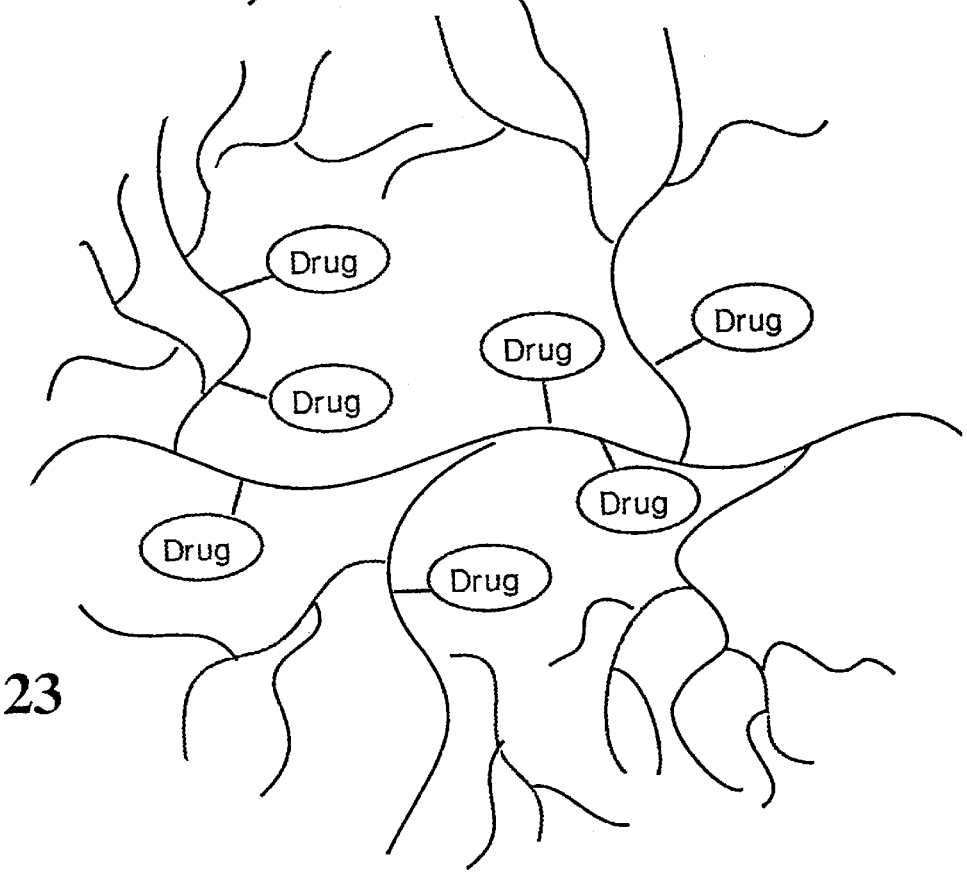
FIG. 23 illustrates a hyper comb-branched polymer conjugate comprising carried drug agents linked within the interior of the polymer.

In the case of utilizing hyper comb-branched polymers, drugs can be attached in the interior of the polymer through both physical and chemical methods, as illustrated in FIGS. 22 and 23. FIG. 22 illustrates carried drugs, or drug agents or intermediates, associated or encapsulated within the interior of a hyper comb-branched polymer. FIG. 23 illustrates such carried material chemically linked to the interior of a hyper comb-branched polymer. The release rate of the drug or carried material may be controlled by the thickness of the exterior layer for physically encapsulated drugs or by cleavage of chemical bonds for chemically linked drugs.

In Examples 13 and 14, it can be seen that hydrophobic drugs (i.e. 4-acetamidophenol) can be physically encapsulated or solubilized by hydrophobic interior modified hyper comb-branched polymers (i.e. $C_6$ and methyl acrylate modified) when dissolved in tris buffer (pH 7.4). In contrast, in the case of unmodified interior hyper comb-branched polymers (hyper comb-branched PEOX or hyper comb-branched terminal $NH_2$ polymers) or tris buffer alone, the drug was completely insoluble. These results suggest that the encapsulation is based on hydrophobic integration instead of an acid-base reaction or ionic interaction. The inventors contemplate that a wide array of pharmaceutical agents could be encapsulated within, or otherwise associated with hyper comb-branched polymers, such as antibiotics, analgesics, antihypertensives, cardiotonics, sedatives, antiepileptics, antipyretics, stimulants, immunosuppressives, and the like; examples are acetaminophen, acyclovir, alkeran, amikacin, ampicillin, amphotericin B, aspirin, bisantrene, bleomycin, neocardiostatin, chloroambucil, chloramphenicol, cytarabine, daunomycin, dilantin, doxorubicin, fluorouracil, gentamycin, ibuprofen, kanamycin, meprobamate, methotrexate, novantrone, nystatin, oncovin, phenobarbital, polymyxin, probucol, procarbazine, rifampin, streptomycin, spectinomycin, symmetrel, thioguanine, tobramycin, trimethoprim, and valban.

Figure 24:
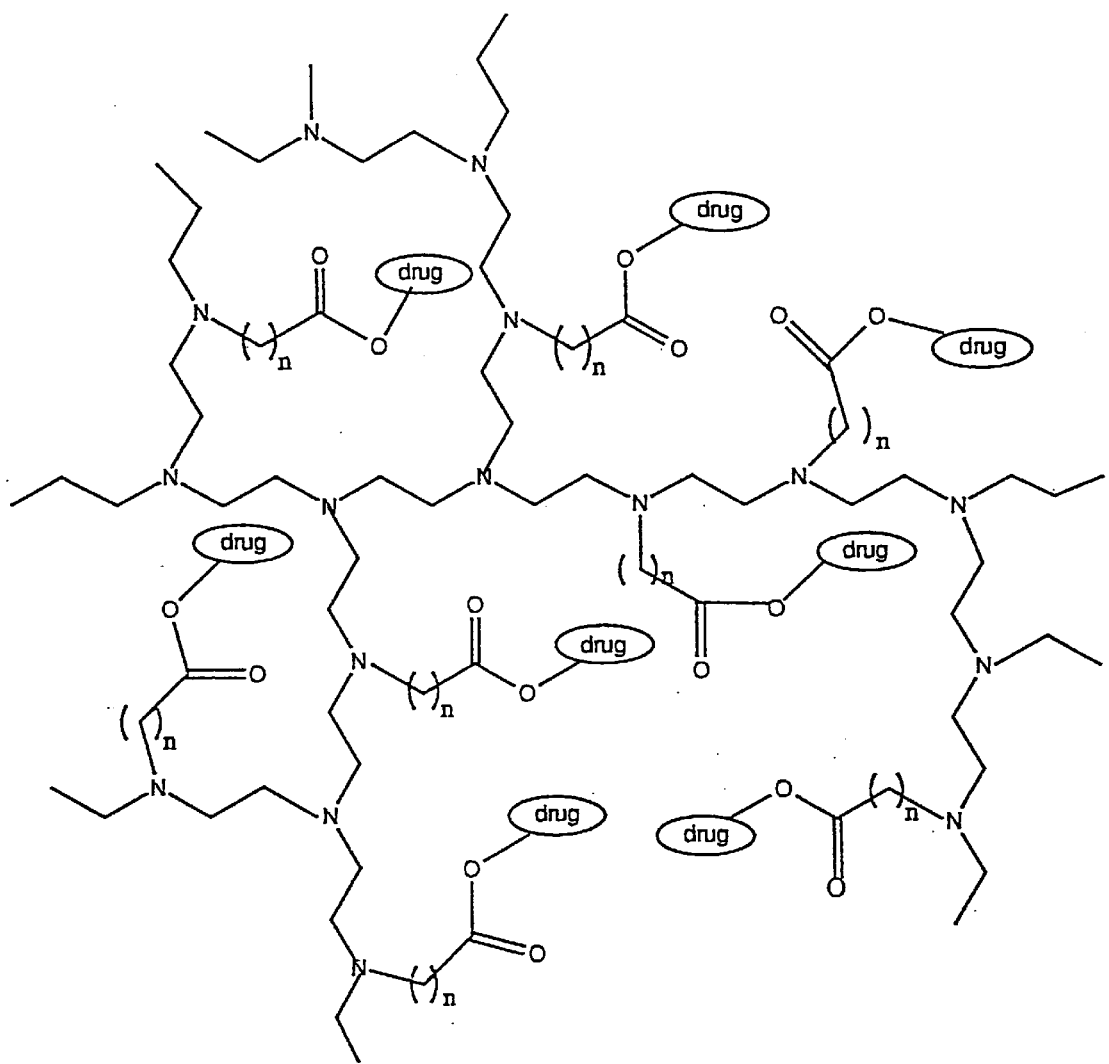
FIG. 24 illustrates a hyper comb-branched polymer conjugate comprising carried drug agents linked to the polymer via ester linkages.
Figure 25:
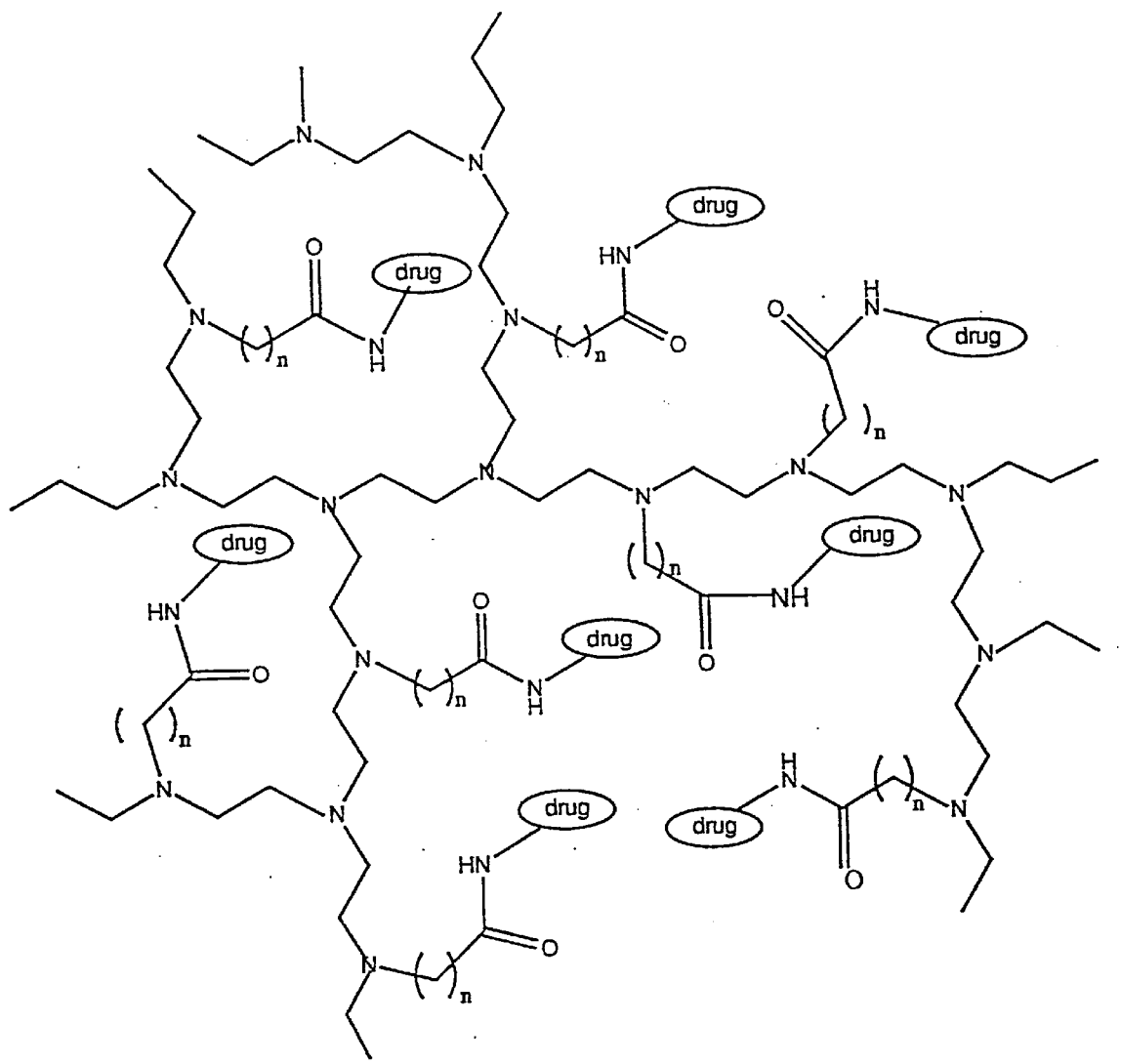
FIG. 25 illustrates a hyper comb-branched polymer conjugate comprising carried drug agents linked to the polymer via amide linkages.

Alternatively, drugs can be linked inside the hyper comb-branched polymers through chemical reactions. In Example 15, hydrophobic moieties such as fluorescein isothiocyanate (FITC) were chemically reacted with interior secondary or primary amines of hyper comb-branched polymers (FIGS. 18 and 19). Drug attachment can also be achieved through other chemical linkages such as ester, anhydride, or amide bonds. Therefore, the drug releasing rate can be controlled by hydrolysis of these chemical bonds under physiological conditions, as illustrated in FIGS. 24 and 25.

EXAMPLE 10

Hydrophilic—Hydrophobic Hyper Comb-Branched Polymer ($C_6$ Interior) [HCB G0 (50% PEOX-$C_6$)]

To a mixture of 50% functionalized PEOX-G0 (0.50 g in 20 ml MeOH) was added 1 g of epoxyhexane. The mixture was heated at 40° C. for 5 days. The solvent and unreacted monomers were removed by rotary evaporation and high vacuum at 80° C. The product was characterized by NMR and SEC.

EXAMPLE 11

Hydrophilic—Hydrophobic Hyper Comb-Branched Polymers (Ester Interior) [HCB G0 (50% PEOX Methyl Acrylate)]

To a mixture of 50% functionalized PEOX-G0 (0.475 g, 20 ml MeOH) was added methyl acrylate solution (0.5 g MA in 0.5 g MeOH) at 0° C. The mixture was allowed to react at 40° C. for 3 days. The pure product was obtained by rotary evaporation, dried by bubbling with $N_2$, and then characterized by NMR and SEC.

EXAMPLE 12

Hydrophilic—Hydrophobic Hyper Comb-Branched Block Copolymers [HCB G0 (PEOX-b-PPOX)]

The synthesis of PEOX100-b-polyphenyloxazoline (PPOX10)-g-PEI20 is provided as a general procedure for the preparation of hyper comb-branched PEOX-b-PPOX-g-PEI copolymers. A mixture of MeOTs (0.1845 g, 0.9906 mmol) in 150 ml of toluene was azeotroped to remove water with a distillation head under Ar for 10 minutes. After cooling to about 90° C., 2-ethyloxazoline (10 ml, 99.06 mmol) was cannulated in and the mixture was allowed to reflux for 5–10 hours. 2-phenyloxazoline (1.8 ml, 7.6 mmol) was then added and the reaction mixture was refluxed for 5 to 10 hours. To this mixture was added morpholine-terminated LPEI 20 (49.5 mg, 0.9906 mmol of NH), which was dried by azeotropic distillation from toluene, followed by immediate addition of i-$Pr_2$NEt (1 to 2 eq.). The mixture was refluxed for 1 hour, cooled, and then dissolved in methanol. After rotary evaporation of the solvents, the crude product was purified by fractionation by methanol/diethyl ether mixture to remove the unreacted monomers, oligomers and catalysts. The entire separation process was monitored by SEC. The purified product was rotary evaporated and lyophilized to produce a hyper comb-branched PEOX-b-PPOX-g-PEI polymer as a white powder. Such polymers were characterized by SEC and NMR. Other hyper comb-branched polymers with different grafting chain lengths, branched cores, and generations (i.e., multi hydrophilic-hydrophobic copolymers) can be prepared in a similar manner.

EXAMPLE 13

Drug Solubilization with $C_6$-Modified Hyper Comb-Branched Polymers

To a vial containing 19.7 mg 4-acetamidophenol in 1 ml tris buffer (pH=7.4) was added 0.12 ml of 7.7% (9 mg) $C_6$ modified hydrophobic interior hyper comb-branched polymer of Example 10. The solution became clear immediately, indicating that drug was solubilized completely. In the control vial, the white solid 4-acetamidophenol remained as a precipitate in tris buffer at the same concentration. Other water soluble hyper comb-branched polymers without hydrophobic interior modifications (i.e. hyper comb-branched G2 PEOX and terminal modified G2-$NH_2$ polymers) could only disperse, but not solubilize 4-acetamidophenol.

EXAMPLE 14

Drug Solubilization with Methyl Acrylate-Modified Hyper Comb-Branched Polymers

To a vial containing 18.7 mg 4-acetamidophenol in 1 ml tris buffer (pH=7.4) was added 0.11 ml of 6.3% (6.9 mg) methyl acrylate-modified hydrophobic interior hyper comb-branched polymer of Example 11. The solution became clear immediately, indicating that the drug was solubilized completely. In the control vial, the white solid 4-acetamidophenol remained as a precipitate in tris buffer at the same concentration. Other water soluble hyper comb-branched polymers without hydrophobic interior modifications (i.e. hyper comb-branched G2 PEOX and terminal modified G2-$NH_2$ polymers) could only disperse, but not solubilize 4-acetamidophenol.

Another aspect of the present invention relating to encapsulated conjugates is the encapsulation of fragrances. One of the benefits in encapsulating fragrant compounds is that their release rate can be significantly decreased and the time period of release can be significantly extended as described in Example 15. Furthermore, it is contemplated that specific release time periods and release rates can be provided by use of the hyper comb-branched polymers described herein.

EXAMPLE 15

Encapsulation and Release of Fragrances

To a glass vial was added 73.4 mg of fragrance (Lagerfeld) and 0.15 mg of $C_6$ interior modified hyper comb-branched polymer in 0.2 ml of water or pH 7.4 buffer. The control solution was formulated by adding 74.6 mg of fragrance in 0.2 mg of water or pH 7.4 buffer. These solutions (5 µl) were then deposted onto AccuWipe™ papers or into open vials to allow slow evaporation in air. In all cases, the fragrance release rates of fragrances encapsulated by hypdrophobically modified hyper comb-branched polymers were much slower than the controls, as evidenced by longer lasting odors (3–4 weeks for hydrophobically modified HCBPs and less than 5 days for controls). The experiments were also performed in an ethanol/water or buffer mixture. The release rates were observed to increase with the ethanol contents.

Signal Amplification

Signal amplification is very important for many in vitro and in vivo diagnostic applications, since carried materials can greatly enhance detection capabilities of nearly all types of measurement instrumentation that employ some type of measuring signal, such as light. In this aspect of the present invention, light reflecting or light absorbing moieties are preferably attached to the periphery of a hyper comb-branched polymer. The FITC experiment (Example 16) is an example of signal amplification, where a large number of chromophores were attached onto a hyper comb-branched polymer. As a result, the signal was greatly enhanced.

EXAMPLE 16

Signal Amplification/Drug Attachment

A mixture of 10 mg of HCB G0 (50% PEOX) in 5 ml sodium borate buffer (pH=9.5) was slowly added, dropwise, to a FITC/DMSO solution (7 mg FITC in 1 ml DMSO). The reaction mixture was shaken for 12 hours in the dark. After extensive ultrafiltration to remove the unreacted FITC, the solution remained yellow-red in color. The formation of the product could also be conveniently monitored by thin layer chromatography (TLC) to check for the formation of dye-modified polymer. Similar covalent chemistry could be used to covalently bond a drug to a hyper comb-branched polymer.

Metal Chelation

A variety of surface modification reactions can be performed upon the hyper comb-branched polymer system. Chelating groups such as —$NH_2$ and COONa were attached onto hyper comb-branched PEI polymers. In Example 17, $Cu^{2+}$ and $Co^{2+}$ were chelated with hyper comb-branched polymers, such as hyper comb-branched PEI polymers, and —COONa, or —$NH_2$ modified hyper comb-branched polymers (FIGS. 18 and 19). All of the hyper comb-branched polymers were able to strongly complex these metals as evidenced by the change of the solution color and/or solubility. The formation of the complexes was also supported by UV measurements, where significant wavelength changes were observed. In addition to $Cu^{2+}$ and $Co^{2+}$, it is contemplated that a wide array of other metal ions could be chelated utilizing the hyper comb-branched polymers described herein. Examples of such metal ions include, but are not limited to the metals in the Periodic Table Groups VIIIA (Fe, Ni, Ru, Rh, Pd, Os, Ir, Pt), IVB (Pb, Sn, Ge), IIIA (Sc, Y, lanthanides and actinides), IIIB (B, Al, Ga, In, Tl), IA alkali metals (Li, Na, K, Rb, Cs, Fr), and IIA alkaline-earth metals (Be, Mg, Ca, Sr, Ba, Ra) and other transition metals. This chelating property is useful not only in biomedical applications such as magnetic resonance imaging (MRI), protein separation, in vitro diagnosis, but also in industrial applications such as metal separation and nuclear waste recovery.

EXAMPLE 17

Metal Chelation

A stock solution containing 1.25 wt. % of $Cu^{2+}$ cupric sulfate in water was divided into five vials. To each of these solutions was added 5 mg each of HCB G0 (propionic acid), HCB G0 (50% acetic acid), HCB G0, HCB G1 (50% PEOX) and HCB G1 (PEOX). The solutions changed from light blue to blue or even deep blue, indicating the formation of the $Cu^{2+}$/hyper comb-branched polymer complexes. These complexes were also characterized by UV. The $Co^{2+}$/hyper comb-branched polymer complexes were prepared and characterized in a similar manner. In this case, solutions from light brown to dark brown were formed.

Gene Transfection

The hyper comb-branched polymers of the present invention may be complexed with genetic material and used for gene therapy in mammalian organisms, e.g., humans. Genetic materials are nucleotide based materials, including without limitation, viruses and viral fragments, plasmids, phages, cosmids, genes and gene fragments (i.e., exons, introns), deoxyribonucleic acid (DNA) both single and double stranded, ribonucleic acid (RNA), ribosomal RNA (rRNA), catalytic RNA (cRNA), small nuclear RNA (snRNA), messenger RNA (mRNA), transfer RNA (tRNA), DNA and RNA oligonucleotides (both single and double stranded) or oligomers and (anti-sense) oligonucleotides, protein nucleic acids (PNA), and substituted nucleic acid oligonucleotides.

A method for preventing or treating a disease comprises transfecting a mammalian cell with hyper comb-branched polymer complexed with genetic material. Genetic material may be transfected into cells for a variety of reasons including the production of proteins within cells, altering cell function, correcting genetic defects, function as drugs, and the like. Thus, genetic diseases or conditions, in particular, may be prevented or treated using the complex of the hyper comb-branched polymer and genetic material of the present invention.

The amount of genetic material used in the genetic material:hypes comb-branched polymer complex solution is sufficient to achieve the desired prophylactic, therapeutic or diagnostic effect. This amount will vary as a function of the effect sought, the ease with which target cells are successfully transfected, the efficiency of any target director attached to the dendrimer, and the mode of administration of the complex, i.e., in vitro, ex vivo, in vivo, and, if in vivo, intravenous, topical or direct injection into a particular tumor, organ, gland or other tissue.

Once the amount of genetic material and its charge has been determined, the amount of hypes comb-branched polymer used is then determined as a function of the genetic material:hypes comb-branched polymer charge ratio selected. Sufficient hypes comb-branched polymer is used in the solution to give the desired charge ratio. The charge ratio selected will vary as a function of the same variables which affect the solution concentration of genetic material, as well as with whether DEA-dextran or glycerol is used to enhance transfection. The "charge ratio" refers to the number of unit positive charges on the hyper comb-branched polymer carrier relative to the number of unit negative charges on the carried genetic material. For purposes of determining this ratio, only the positive charges on the last generation of added branches are included, where the genetic material is to be carried on the surface of the polymer. If the genetic material were to be carried on an interior generation of branches, only the positive charges on that interior generation of branches would be included. The generation of branches primarily responsible for carrying the genetic material are sometimes referred to herein as the "carrier generation branches."

The number of charges on the carrier generation branches in one molecule of a hyper comb-branched polymer can be obtained by measuring the absolute molecular weights of the hyper comb-branched polymers with their carrier generation branches, and without their carrier generation branches, and the absolute molecular weight of the carrier generation linear branches by multi angle laser light scattering. The number of charges were calculated based upon the following equations:

$$N = \text{number of charges} = \frac{MW(G) - MW(G-1)}{MW(br)} \times DP(br) \quad (1)$$

$$\text{Charge density (charges}/\mu g) = \frac{N}{MW(G)} \times 6.02 \times 10^{17} \text{ charges}/\mu g \quad (2)$$

MW(G) is the absolute molecular weight of hyper comb-branched polymer generation G polymer i.e. with the carrier generation branches attached.

MW(G—1) is the absolute molecular weight of hyper comb-branched polymer generation G—1 polymer i.e. without the carrier generation branches attached.

MW(br) is the absolute molecular weight of the linear carrier generation branches.

DP(br) is the degree of polymerization of the linear carrier generation branches.

It is assumed in this equation that each polymerization unit on each carrier generation branch has or will be modified to have a unit positive charge. Where the chemistry used is otherwise, the formula has to be modified accordingly.

Generally speaking, the genetic material:hypes comb-branched polymer charge ratio may be from about 1:10 to about 1:10,000 (possibly even lower), but more preferably from about 1:10 to 1:1,000, as a function of the above variables. Even more preferred are charge ratios of from about 1:100 to about 1:1000, with a charge ratio of about 1:200 being most preferred.

A complex or conjugate of a hyper comb-branched polymer and genetic material is prepared by reacting the hyper comb-branched polymer with the desired genetic material in a suitable solvent at a temperature which facilitates the complexing of the genetic material with the polymer. This method may further include placing the complex in a solution with DEAE-dextran, chloroquine, or glycerol as an enchancing agent. The preferred temperatures to facilitate complexing range from about 20° C. to about 40° C., however preparation techniques at both higher and lower temperatures are encompassed within the present invention. The preferred pH for the complexing solution range from about 5 to about 10, but higher and lower values may be appropriate. The hyper comb-branched polymer preferably has an outer periphery of positively charged sites to facilitate electrostatic attachment of genetic material.

In an alternate embodiment, a complex or conjugate of a hyper comb-branched polymer and genetic material that can be readily diluted for subsequent use, is prepared by mixing genetic material and hyper comb-branched polymer having a positive surface functionality, in water. The concentration of genetic material is about 1 $\mu$g to about 10 $\mu$g per 20 $\mu$L of mixture. The amount of polymer is primarily dependent upon the number of its available positively charge sites, but should be added to effect a genetic material: polymer charge ratio of from about 1:10 to about 1:10,000. The method preferably further comprises mixing the above described mixture at a pH of from about 5 to about 10 and a temperature of from about 20° C. to about 40° C.

A method for introducing human genes into mammalian cells to avoid substantial gene rearrangement or other alterations that may affect gene expression may be conducted by transfecting a mammalian cell with a hyper comb-branched polymer complexed with genetic material.

Gene transfer can be effected by transfecting a variety of cell types such as hematopoietic cells, skin fibroblasts, hepatocytes and the like. Thus, a method for preventing or treating a genetic disease may comprise transfecting a hyper comb-branched polymer complexed with genetic material into a hematopoietic stem cell, skin fibroblast cell, hepatocyte, or the like, administering the transfected cell into a mammalian organism and expressing said cell to obtain a prophylactic or therapeutic effect.

Cell transfecting can be effected in a variety of fashions. In one method, a complex of a hyper comb-branched polymer and genetic material is simply made available to cells to be transfected. This technique may be employed to transport genetic material through a cellular membrane and into a cellular nucleus.

In another embodiment, a method for protecting genetic material from digestion during transit to and transfection into a cell may be provided by complexing genetic material with hyper comb-branched polymer prior to exposing the genetic material to digestive enzymes.

Moreover, the hyper comb-branched polymers of the present invention can be utilized to stabilize and compact genetic material by complexing genetic material with the hyper comb-branched polymers described herein.

The transfection in the present invention can be used for a variety of purposes, including in vitro, in vivo and ex vivo uses. Further, the in vitro use of the complex of hyper comb-branched polymers and genetic material of the present invention can be useful in detecting or diagnosing various conditions. A method for diagnosing a disease or condition in a mammalian organism may be detected or diagnosed using the complex of the hyper comb-branched polymer and genetic material of the present invention.

Due to the convenient design and synthesis of hyper comb-branched polymers having different sizes, shapes, and functionalities, a variety of surface modified hyper comb-branched polymers were prepared and evaluated for gene transfection. Experiments were conducted in which the ability of hyper comb-branched polymers to transport carried genetic material was evaluated and compared to several known carriers, i.e. the controls, Starburst® polymers, which are the subject of U.S. Pat. Nos. 4,507,466 entitled DENSE STAR POLYMER BRANCHES HAVING CORE, CORE BRANCHES, TERMINAL GROUPS, 4,558,120 entitled DENSE STAR POLYMER, and 4,568,737 entitled DENSE STAR POLYMERS AND DENDRIMERS, and Lipofectamine™.

In all experiments, samples of carrier agent, i.e. hyper comb-branched polymers, Lipofectamine™, or Starburst® polymers, were complexed with genetic material. The hyper comb-branched polymers included —$NH_2$, —NH—, 100% PEOX, 50% PEOX, and chloroethylamine modified hyper comb-branched polymers. The inventors also contemplate that a wide array of amino acids, could be attached to the periphery of the polymer, such as but not limited to lysine or arginine. The conjugated samples included a large range of ratios of negatively charged genetic material to positively charged carrier agent, i.e. about 1:10 up to about 1:1000, respectively (ratios based upon the number of charge sites).

Testing also included the use of other known carrying agents to assist either the hyper comb-branched polymers of the present invention, or the control samples which utilized Starburst® polymers or Lipofectamine™. The medium utilized in all experiments was DMEM, Dulbecco's modified eagles medium. Ratios of genetic material to hyper comb-branched polymer were based on the calculation of the electrostic charge present on each component; the number of phosphate groups in the nucleic acid ratioed to the number of charges on the carrier branches in one molecule of a hyper comb-branched polymer.

The transfection efficiency, or genetic material carrying ability of the samples was quantified by measuring relative light units or RLU per 10 $\mu$g protein. In order to quantity the transfection efficiency, a reporter gene (pCMV LUC) was complexed to the hyper comb-branched polymer and transfected into the cells. The cells were lysed and the amount of light produced after addition of Luciferin™ was quantified in a luminometer. The experiments were performed on Cos1 and Rat2 cell lines. The CMV-luceferase gene was utilized as a reporter gene. The total protein concentration in the cell lysate was measured in a standard protein assay.

Due to the lower charge densities in the 100% PEOX and 50% PEOX modified hyper comb-branched samples, the binding between negatively charged DNA and positively charged hyper comb-branched polymers was very weak. Therefore, the transfection efficiency observed was the lowest for that system, as illustrated in FIGS. 29 and 33. Referring to both figures, it can be seen that the measured RLU was barely detectable for hyper comb-branched polymers (designated as HCB in the accompanying figures) HCB G1 PEOX 100G0 at charge ratios of 1:10 and 1:70; and HCB G1 50% PEOX 50G0 at charge ratios of 1:10; 1:100; and 1:200.

In contrast, when modified with primary amines, hyper comb-branched polymers were found to transfect genes very efficiently. As shown in FIGS. 29 and 30, the transfection efficiency of polyamidoamine (PAMAM) modified hyper comb-branched polymer in Cos1 cells was better than not only the Starburst® G5 and G10 dendrimers, but also Lipofectamine™, which is recognized as a premier standard for gene transfection. That is, the RLU measurements for HCB G3 (PAMAM) in FIGS. 29 and 30 (including conjugation ratios of 1:10, 1:100, 1:200, and 1:500), were significantly greater than the RLU measurement for the corresponding control samples presented in those figures.

Since Starburst® dendrimers are formed by a series of reiterative or generational reactions, they are typically identified by the number of generations to which they have been reacted, e.g. G5, G10, etc. Under current nomenclature, a Starburst® dendrimer core with a first set of branches attached thereto is referred to as a "zero generation" or G0 dendrimer. Once the second set of branches it attached to the first set of branches, it is a first generation or G1 Starburst® dendrimer. Starburst® dendrimers are identified herein in accordance with this generational nomenclature scheme.

Much of the prior patent literature involving Starburst® dendrimers uses a variation on this nomenclature in which a core with a first set of branches emanating therefrom is referred to as a first generation or G1 dendrimer, instead of a zero generation or G0 dendrimer. Thus, the same Starburst® dendrimer will have a different "G" number, depending upon whether the whole nomenclature literature is followed, or whether the current nomenclature is utilized. The current nomenclature, in which the core and first set of branches are referred to a "G0" Starburst® dendrimer, is used herein.

In addition, it is even more remarkable that in one of the experiments, illustrated in FIG. 30, the highest transfection utilizing the hyper comb-branched polymers was obtained with Dulbecco's modified eagles medium (DMEM) alone without the help of "boosters" such as DEAE-dextran which is cytotoxic, and chloroquine, which blocks endosomal localization of the complexes and subsequent DNA degradation. This suggests that hyper comb-branched polymers enhance transfection in certain cells by apparently blocking endosomal uptake of complexed DNA; this is a unique characteristic of the hyper comb-branched polymer conjugated system not seen with Starburst® dendrimer mediated transfection.

Hyper comb-branched polymers have another important advantage in transfection. These polymers are minimally cytotoxic, at charge ratios of DNA:polymer up to 1:100. This is in contrast to randomly branched PEI polymers, which transfect cells but show marked toxicity at charge ratios as low as 1:50 for both the Rat2 and Cos1 cell lines. FIGS. 32 and 36 show these results in comparison to the G5 and G10 Starburst® dendrimers. Also by comparison, the level of transfection efficiency is very low with respect to the Starburst® dendrimer and therefore to the hyper comb-branched polymers of the present invention. This data demonstrates that it will not likely be feasible to utilize branched PEI polymers for gene transfection nor to safely deliver genetic material for therapeutic interest due to the relatively high cytotoxicity of the polymers.

Chloroethylamine modified hyper comb-branched polymers were also found to transfect genes reasonably well (FIGS. 31 and 35). Terminal primary amine modified hyper comb-branched polymers could not transfect genes efficiently, even though their sizes are larger than that of G10 dendrimers. This may be the result of an inability of these polymers to bind either the DNA or negatively charged phospholipids on the surface of cells (thereby failing to trigger transfection). Secondary amine modified hyper comb-branched polymers did show some transfection. However, the overall solubility of these types of polymers in physiological condition was very low.

In Rat2 cell line, primary amine modified (i.e. PAMAM modified) hyper comb-branched polymer (molecular weight of about 29,000) in DMEM also showed much higher gene transfection efficiency than that of the Starburst® G5 and G10 with DMEM alone. Referring to FIGS. 33 and 34, the RLU measurements for HCB G3 (PAMAM) at charge ratios of 1:10, 1:100, 1:200, 1:500, all in DMEM, were significantly higher than any of the control Starburst® samples in DMEM.

EXAMPLE 18

Hyper Comb-Branched Polymers as Gene Transfer Carriers

A hyper comb-branched polymer diluting buffer containing 20 mM HEPES (pH 7.9), 100 mM KCl, 0.2 mM EDTA, 0.5 mM DTT, and 20% (v/v) glycerol, was formed. A binding buffer including 10 mM EDTA, 40% (v/v) glycerol, 50 mM DTT, 100 mM TRIS HCl (pH 7.5), and 1000 mM NaCl was formed. To a sterile Eppendorf™ tube containing an appropriate volume of binding buffer was added appropriate amounts of hyper comb-branched polymers followed by CMV-Luc plasmid DNA at the desired ratios (i.e. from 1:1 to 1:1000). The complex spontaneously formed within about 15 minutes. The complex was applied to the cells at the conditions such as with Dulbecco's modified eagles medium (DMEM) alone, or with DEAE-dextran, or with chloroquine, or with both DEAE-dextran and chloroquine. The transfection efficiency was determined by luciferase assay. The assay reagent contained 2 mM TRIS glycine, 10.7 mM (MgCO3) Mg(OH)$_2$•5H$_2$O, 2.67 mM MgSO$_4$, 0.1 mM EDTA, 33.3 mM DTT, 270 $\mu$M Coenzyme A, 40 $\mu$M Luciferin™, 530 $\mu$M ATP, at a total solution pH of 7.8.

Hyper comb-branched polymers with different surfaces (i.e. PEOX, PEI, 50% PEOX, —NH$_2$, etc.) and sizes (i.e. from 3 to 50 nm) were utilized in the gene transfer experiments. The transfection experiment was performed on different cell lines. The optimized transfection results were observed with primary amine modified hyper comb-branched polymers in both Rat2 and Cos1 cell lines. Among the primary amine modified hyper comb-branched polymers, the PAMAM modified hyper comb-branched polymers gave the best result, particularly in the Cos1 cell line, where efficient transfection efficiency was obtained without the requirement for additional agents.

Congugates and Other Vehicles

The present invention is also directed to hyper comb-branched polymer conjugate compositions in which the conjugates are formulated with other suitable vehicles. The hyper comb-branched polymer conjugate compositions may optionally contain other active ingredients, additives and/or diluents. Injectable compositions of the present invention may be either in suspension or solution form. In solution form the complex is dissolved in a physiologically acceptable carrier. Such carriers comprise a suitable solvent, preservatives such as benzyl alcohol, if needed, and buffers. Useful solvents include, for example, water, aqueous alcohols, glycols, and phosphonate or carbonate esters. The hyper comb-branched polymer drug conjugate also could be incorporated in vesicles or liposomes. Also the conjugate could be encapsulated into a polymeric host system that could either be degradable (i.e., lactic-glycolic acid copooymers or a polyanhydride polymer) or nondegradable (ethylene-vinylacetate copolymer). Also the conjugate could be incorporated into a hydrogel matrix comprising either poly(hydroxylethylmethacrylate) or poly(vinylalcohol). A variety of enteric coating systems could be employed to help the hyper comb-branched polymer drug conjugate pass through the stomach.

The hyper comb-branched polymer drug conjugate could be formulated into a tablet using binders known to those skilled in the art. Such dosage forms are described in *Remington's Pharmaceutical Sciences*, 18th edition, 1990, Mack Publishing Company, Easton, Pa. Suitable tablets include compressed tablets, sugar coated tablets, film-coated tablets, enteric-coated tablets, multiple compressed tablets, controlled-release tablets, and the like.

Enteric-coated tablets are particularly advantageous in the practice of the present invention. Enteric coatings are those which remain intact in the stomach, but will dissolve and release the contents of the dosage form once it reached the small intestine. The purpose of an enteric coating is to delay the release of drugs which are inactivated by the stomach contents, or may cause nausea or bleeding by irritating the gastric mucosa. In addition, such coatings can be used to give a simple repeat-action effect where additional drug that has been applied over the enteric coat is released in the stomach, while the remainder, being protected by the coating, is released further down the gastrointestinal tract.

Useful polymers for the preparation of enteric coated tablets includes cellulose acetate phthalate, polyvinyl acetate phthalate, hydroxypropyl methylcellulose phthalate, methacrylic acid ester copolymers and the like.

In the agricultural materials embodiment of the invention, the hyper comb-branched polymer conjugates can be formulated with suitable vehicles useful in agriculture such as in treatment of crops or fallow land, or as pesticides, or in treatment of in vivo or in vitro testing of animals. An agriculturally acceptable carrier or diluent which may also be present with one or more hyper comb-branched polymer conjugates of the present invention includes those carriers or diluents customarily used in granular formulations, emulsifiable concentrates, solutions, or suspensions such as, for example, toluene, xylene, benzene, phenol, water, methane, hydrocarbons, naphthalene and the like.

Examples Relating to Producing Hyper Comb-branched Polymers

Example A

A 250 ml one-necked round-bottomed flask equipped with a magnetic stirring bar and a Dean-Stark trap that was surmounted with a reflux condenser was charged with 2.84 gm (15.3 mmole) of methyl tosylate and 125 ml of toluene. The mixture was heated at reflux and solvent was collected until all water had been removed. At this time, 30.0 gm (303 mmoles) of freshly distilled 2-ethyl-2-oxazoline was added all at once and the mixture was refluxed for approximately 4 hours. During this time, in a separate flask, 1.64 gm (38.1 mmole of repeat units) of linear poly(ethyleneimine) (LPEI) was azeotropically dried with toluene. When the poly (ethyleneimine) was dry it was added to the round-bottomed flask containing the oxazoline oligomer and then allowed to reflux for an additional 3 hours. Any ungrafted living poly(2-ethyl-2-oxazoline) chains were neutralized by the addition of 20 ml of water with refluxing for an additional 1 hour. Toluene was removed under reduced pressure to leave a yellowish oily solid that was dissolved in chloroform and precipitated dropwise into diethyl ether. The yellow solid was filtered from solution and dried overnight in a vacuum oven to yield 29.7 gm (94% yield) of grafted poly(2-ethyl-2-oxazoline) (PEOX) as a yellow powder.

Example B

Into a 500 ml one-necked round-bottomed flask was placed 21.6 gm of the PEOX from Example A and 350 ml of water. When the polymer had completely dissolved, 35 ml of concentrated sulfuric acid was added. The flask was equipped with a distillation head and the mixture was heated at reflux and distillate was collected until propionic acid could not be detected. Water was added to the distilling pot when the volume was reduced to less than approximately 75 ml. Upon removal of the propionic acid the distillation head was replaced with a reflux condenser surmounted with a pressure equalized addition funnel charged with 5N NaOH. The base was slowly dripped into the reaction mixture maintained at reflux. When the pH of the reaction mixture was approximately 12, heating was discontinued. While standing at room temperature a solid formed at the surface of the aqueous mixture. This solid was removed and placed in a 250 ml round-bottomed flask with 175 ml of toluene. The water was removed from the water-toluene azeotrope by distillation. When water removal was complete, the solid became soluble in the refluxing toluene. The hot toluene solution was poured into a 250 ml round-bottomed flask leaving behind insoluble salts. Toluene was removed under reduced pressure to leave a brownish, waxy solid. The sample was dried for approximately 24 hours under vacuum to give 9.14 gm (97% yield) of polymer sample.

Example C

Using the general method of Example B, hydrolysis of the graft polymers, was carried out on a separate batch of the graft polymers in the following manner. Five grams (5.0 gm) of the graft copolymer were placed in a 250 ml round-bottomed flask with 100 ml of water and 10 gm of sulfuric acid. The flask was heated with a heating mantle to give a slow distillation of the propionic acid/water azeotrope. The distillation was continued for 2 days, with water being added as necessary to maintain the reaction volume. Approximately 200 ml of distillate was collected over the course of the hydrolysis. The heating was discontinued and 50% NaOH was added slowly to bring the pH to 10. The free polyamine was insoluble in the saturated salt solution, giving a separate phase on top of the aqueous solution. The phases were separated and the polyamine was placed in a 250 ml round-bottomed flask. One hundred fifty ml of toluene was added and a Dean-Stark trap was attached. After reflux overnight (about 16 hours), no more water was removed and the polyamine had dissolved in the hot toluene. The hot solution was filtered and the solvent was removed from the filtrate using vacuum and agitation to give branched poly(ethyleneimine) weighing 2.2 gm (100% of theory) as an orange oil. The $^{13}$C-NMR spectrum showed a peak for linear poly(ethyleneimine) (49.4 ppm/intensity 8075), residual unhydrolyzed propionamide (9.5 ppm/ intensity 156), (26.3 ppm/intensity 180), and primary amine end group (41.7 ppm/intensity 61). No peak for a hydroxy terminal group was observed. While the intensities may not be interpreted as a quantitative measure of the groups present, qualitatively, hydrolysis was 80% to 90% complete and grafting was complete within the limits of detection.

Example D

A 2-liter, 3-necked, round-bottomed, glass flask was used with a shaft driven stirrer, instead of magnetic stirring. The initial loading was: water –250 ml, material prepared essentially by the method of example 3—125 gm, sulfuric acid—150 gm. Additional sulfuric acid, 100 gm was added halfway through the hydrolysis to improve solubility. Internal flask temperature was monitored and a solenoid valve was rigged to add water whenever the temperature rose above 107° C. Thus, constant attention was not necessary and the distillation could be left unattended overnight. The heating mantle was also set to shut off at the same temperature so that the flask would not overheat if the water reservoir ran out of water. After 2 days of continuous distillation, 1.6 liters of distillate was collected. The reaction mixture was neutralized and the polymer phase was separated. The crude polymer was purified by dissolving in hot water (1 liter) and precipitated by slow addition to cold water. After two precipitations, the supernatant solution was neutral to Hydrion® paper. The resulting hydrated polymer was dehydrated via toluene azeotrope as described above to give LPEI (51 gm 94% yield). The $^{13}$C-NMR spectrum showed LPEI with residual amide carbon intensities 0.5% of the LPEI intensity. Primary amine end group intensity was 0.4% of the LPEI intensity.

Example E

Into a 250 ml round-bottomed glass flask was placed p-toluenesulfonic acid monohydrate (2.0 gm, 11 mmole) and toluene (100 ml). A Dean-Stark trap was attached and the mixture was heated at reflux until water removal was complete. Ethyl oxazoline (10 gm, 100 mmole) was added all at once and the reflux was continued for 2 hours. LPEI (1.0 gm, 23 meq.) was placed in toluene (25 ml) and the mixture was heated to boiling to dissolve the polymer and azeotropically remove trace water in the polymer. The hot LPEI solution was added all at once, to the cloudy oligomer suspension. An orange oil began to precipitate immediately. After 1 hour at reflux, the mixture was cooled and the solvent stripped using vacuum. The residue was dissolved in $CH_2Cl_2$ (40 ml) and precipitated by a slow addition to ether (500 ml). The solid was collected by filtration and dried in a vacuum oven at 40° C. to 50° C. to give the grafted polymer (12 gm, 92% yield) as a yellow powder. At higher M/I ratios, the oligomerization time had to be increased to allow complete conversion of the ethyl oxazoline. For example, intermediated degree of polymerization runs (M/I= 200, olig. time=3 hours. or M/I=400, olig. time=6 hours) had low yields due to incomplete conversion. Increasing the reaction time to 12 hours and 24 hours respectively, gave higher conversions and yields. The highest M/I (1000) run, had an oligomerization time of 36 hours, which was not long enough for complete conversion. This gave a material with actual oligomer dp of 700. The $^{13}$C-NMR spectrum of the poly-branched polymer derived from this material showed a peak for primary amine end groups which was approaching the limits of detection for the signal/noise ratio. No hydroxyl terminal group was detectable.

Example F

Preparation of Morpholine Terminated Linear Polyethyleneimine Having a Degree of Polymerization (dp) of 20

A mixture of methyl tosylate (7.46 g, 40 mmol) in 200 ml of toluene was azeotroped to dryness with a Dean-Stark trap for about 10 to 15 minutes. To this mixture which had cooled to about 90° C. was added ethyl oxazoline (79.3 g, 800 mmol) and the mixture was refluxed for 18 hours. After this time, morpholine (14 g, 161 mmol) was added. This mixture was refluxed for 16 hours. This mixture was evaporated of volatiles on a rotary evaporator. This crude mixture was hydrolyzed with 400 ml of 50% $H_2SO_4$ by azeotroping the water-propionic acid mixture with a Dean-Stark trap until about 500 ml were collected or until the pH of the distillate was neutral. This hot mixture was slowly poured into a 50% KOH mixture under an atmosphere of $N_2$. The resulting heterogenous mixture was made homogeneous by heating to reflux. The product floated to the top of this mixture as a clear liquid. This hot mixture was allowed to cool under $N_2$ to room temperature. The solid cake that formed on the surface of this mixture was dissolved in 600 ml of deionized water by heating to reflux, allowed to cool and ultracentrifuge (8000 rpm) for 10 minutes. The clear liquid was decanted and the remaining white solid-water mixture was mixed with toluene. This mixture was azeotroped of water to form a dry toluene-LPEI mixture. The toluene was removed from this mixture by a rotary evaporator followed by high vacuum (0.2 mm Hg) at 80° C. for 2 hours to give 34 g (88% yield) of the title compound.

Example G

Preparation of Comb-Branched PEI Wherein $N_c$ is 20, $N_b$ is 5 and G is 0

A mixture of methyl tosylate (MeTOs) (3.7 g 20 mmol) in 50 ml of toluene was azeotroped to dryness with a Dean-Stark trap under nitrogen for 10 minutes. To this mixture cooled to 90° C. was added ethyl oxazoline (10 g, 100 mmol). This mixture was stirred for 10 hours at 90° C. To this mixture was added N-morpholine terminated LPEI (dp of 20) (0.53 g, 0.55 mmol, 11 mmol NH) dissolved in 20 ml of hot (90° C.) toluene which had been dried by azeotropic distillation for about 15 minutes. This was immediately followed by the addition of diisopropylethylamine (12 g, 93 mmol, 8 equivalents of amine per NH). This mixture was refluxed for 48 hours. The volatiles were removed from this mixture and the resulting residue dissolved in deionized water. After ultrafiltration (MW>1000), the retentate was refluxed in 400 ml of 50% $H_2SO_4$ for 18 hours. The cooled reaction mixture was made basic to a pH≦14 with KOH to produce a clear colorless liquid that floated to the top of the mixture. Upon cooling the liquid solidified. The solid was removed from the mixture and dissolved in 500 ml of hot deionized water. This mixture was allowed to cool forming a white suspension. This resulting mixture was ultracentrifuge at about 8000 rpm for about 10 minutes. The clear liquid was decanted from the white precipitate. The white precipitate was refluxed with toluene with an attached Dean-Stark trap to dry the product. The toluene mixture was evaporated of volatiles on a rotary evaporator. The remaining volatiles were removed at 0.1 mm Hg at 50° C. to give 1.8 g (70%) of the title compound. A $^{13}$C-NMR spectrum of this mixture in CDCl$_3$ indicated at 65% grafting of PEOX onto LPEI as shown by integration of the terminal methyl signals versus the methylene carbon signals.

Example H

Preparation of a Hyper Comb-Branched Polymer PEI Wherein $N_c$ is 20, $N_b$ is 5 and G is 1

The compound dendrimer was prepared in the same manner as in Example G using MeOTs (3.7 g, 20 mmol), 300 ml of toluene, ethyl oxazoline, (10 g, 100 mmol), diisopropylethylamine (12 g, 93 mmol) and comb-branched PEI where $N_c$ is 20, $N_b$ is 10 and G is zero (1.0 g, 23 mmol NH maximum). Ultrafiltration, hydrolysis and drying gave 5.0 g (80% yield) of the title compound. The $^{13}$C-NMR spectrum was consistent with the proposed structure.

Example I

Preparation of a Hyper Comb-Branched Polymer PEI Wherein $N_c$ is 20, $N_b$ is 5 and G is 2

This example shows the use of the material formed in Example H which was refluxed with two equivalents of PEOX having a dp of 5 per NH and 11 equivalents of diisopropylethylamine for two days. This mixture was worked up differently than the previous example. The crude PEOX-hyper comb-branched polymer PEI was hydrolyzed directly, without ultrafiltration, to give 8.6 g of a hyper comb-branched polymer and linear Polyethyleneimine (PEI). This mixture was dissolved in hot deionized water. Upon cooling the product crystallized from the mixture. The mixture was ultracentrifuged at 8000 rpm and the white precipitate was azeotropically dried with toluene to give 4.5 g for a yield of 72%.

Example J

Preparation of a Hyper Comb-Branched Polymer PEI Wherein $N_c$ is 20, $N_b$ is 5 and G is 3

The preparation of hyper comb-branched polymer PEI where G is 3 incorporated improvements in the grafting step by using two equivalents of PEOX per NH and 26 mmols of diisopropylethylamine per NH. The crude material was hydrolyzed as before and the resulting mixture precipitated from PEI by making basic with KOH. Recrystallization of the cake of product floating on the KOH mixture from deionized water followed by ultracentrifugation at 8000 rpm and azeotropic drying of the white solid with toluene gave 5.6 g for a 90% yield.

Example K

Preparation of a Hyper Comb-Branched Polymer PEI Wherein $N_c$ is 20, $N_b$ is 5 and G is 4

The hyper comb-branched polymer PEI was prepared in a manner similar to the previous example, using two equivalents of PEOX per NH, and 23 equivalents of diisopropylethylamine per NH and refluxing two days. The crude mixture was not ultrafiltered by hydrolyzed with H$_2$SO$_4$, removed from solution by KOH and recrystallized twice from deionized water. Each recrystallization involved dissolving the product in hot water, allowing the mixture to cool to 25° C. and ultracentrifugation at 8000 rmp 10 minutes. The clear supernatant was decanted from the white solid and the white solid was azeotropically dried with toluene. The isolated yield from the second recrystallization came to 4.9 g for a yield of 78%. The first recrystallization gave 5.5 g, for a yield of 87%.

Example L

Preparation of a Hyper Comb-Branched Polymer PEI Wherein $N_c$ is 20, $N_b$ is 5 and G is 5

The next generation (G) was prepared at twice the scale of all the other grafting experiments (2.0 g starting material versus 1.0 g of starting material). Only 4 to 5 equivalents of diisopropylethylamine per NH were used along with two equivalents of PEOX per NH and refluxing 2 days. After evaporating the volatiles the crude mixture was dissolved in deionized water and ultrafiltered using a spiral wound cartridge Amicon S1Y3 (3000 MWCO). Hydrolysis of the retentate gave an 85% yield of the title compound. The ultrafiltration with this membrane was not tried on earlier generations of G=1 to 4.

Example M

Preparation of a Hyper Comb-Branched Polymer PEI Wherein $N_c$ is 20, $N_b$ is 5 and G is 6

This generation was prepared in a similar manner as before using two equivalents of PEOX per NH, six equivalents of diisopropylethylamine per NH and refluxing 2 days. The workup again was done by ultrafiltration in deionized water using a spiral wound S1Y3 membrane. The isolated yield of PEOX-hyper comb-branched polymer after ultrafiltration came to one-half the amount normally obtained from an 80% to 90% grafting experiment. Hydrolysis of the mixture as before followed by treatment with NaOH and azeotropic drying with toluene gave only a 32% yield of the G=6 product. A repeat of this same experiment except with two recrystallizations in water instead of an ultrafiltration gave a 38% yield of the title compound.

Example N

Preparation of a Hyper Comb-Branched Polymer PEI Wherein $N_c$ is 20, $N_b$ is 10 and G is 0

A mixture of MeOTs (7.4 g, 40 mmol) in 100 ml of toluene was azeotroped to dryness with a Dean-Stark trap under nitrogen for 10 to 15 minutes. To this mixture, cooled to about 90° C., was added ethyl oxazoline (39.7 g, 400 mmol). This mixture was refluxed under nitrogen for 18 hours. To this mixture was added N-morpholine terminated LPEI having a dp of 20 (1.0 g, 1.1 mmol, 23 mmol of NH) dissolved in 50 ml of hot (100° C.) toluene which had been dried by azeotropic distillation for 15 minutes. This was immediately followed by the addition of diisopropylethylamine (24 g, 186 mmol, 8 equivalents amine per NH). This mixture was refluxed for 48 hours. The mixture was cooled, dissolved in methanol and evaporated of volatiles on a rotary evaporator and the resulting mixture was dissolved in deionized water (about 60 ml). This mixture was ultrafiltered using an Amicon spiral wound cartridge S1Y3 with the above volume as a retentate until 12 liters of permeate had been obtained (20 recirculations). This retentate was refluxed in 400 ml of 50% H$_2$SO$_4$ with a Dean-Stark trap collecting about 400 to 500 ml of distillate (replenishing the equivalent water) until the distillate was neutral to pH paper. This hot mixture was made basic by pouring slowly into a 50% KOH mixture under a blanket of nitrogen. The heterogenous mixture was heated to a homogeneous mixture that produces a liquid that floats to the top of the mixture. Upon cooling the liquid solidified. The solid was removed from the mixture and dissolved in 500 ml of hot deionized water. This mixture was allowed to cool forming a white suspension. This resulting mixture was ultracentrifuged at 8000 rpm for about 10 minutes. The clear liquid was decanted from the white precipitate. The white precipitate was refluxed with toluene with an attached Dean-Stark trap to dry the product. The toluene mixture was evaporated of volatiles on a rotary evaporator. The remaining volatiles were removed at 0.1 mm Hg at 50° C. to give 1.8 g (70%) of the title compound. A $^{13}$C-NMR spectrum of this mixture in $CDCl_3$ indicated a 65% grafting of PEOX onto LPEI as shown by integration of the terminal methyl signals versus the methylene carbon signals.

Example O

Preparation of a Comb-Branched PEI Wherein $N_c$ is 20, $N_b$ is 10 and G is 0

A mixture of morpholine-terminated LPEI having a dp of 20 (1.04 g, 22 mmol), PEOX oligomers having a dp of 10 (47.5 g, 40 mmol) and diisopropylethylamine (20 g, 6 to 7 equivalents per NH) were refluxed under nitrogen obtained from a nitrogen cylinder (constant pressure and no flow) and a Hg bubbler for 48 hours. The volatiles were removed from the mixture and the resulting yellow orange residue was dissolved in 1 liter of deionized water. The mixture was ultrafiltered with an Amicon spiral wound cartridge using 700 ml of retentate and 8.5 liters of permeate to give 24 grams of the PEOX-Comb-Branched PEI copolymer. The material was hydrolyzed with 50% $H_2SO_4$ and the resulting mixture added to an excess of 50% KOH. The cake floating on the KOH was mixed with toluene and azeotropically dried under nitrogen to give 10.1 g (90%) of the Comb-Branched PEI dendrimer.

Example P

Preparation of a Hyper Comb-Branched Polymer PEI Wherein $N_c$ is 20, $N_b$ is 10 and G is 1

The preparation of G=1 of this hyper comb-branched polymer PEI series was identical in all respects to the preparation of G=0. The isolated yield of the title compound from 1.1 g of G=0 Comb-Branched PEI was 10.5 g (84%). The $^{13}$C-NMR system showed a little more of the carbinol signal at 60.1 ppm than before, plus a signal at 59.46 ppm.

Example Q

Preparation of a Hyper Comb-Branched Polymer PEI Wherein $N_c$ is 20, $N_b$ is 10 and G is 2

This material was prepared as described in the previous preparations utilizing an Amicon S1Y10 spiral wound ultrafiltration cartridge (10,000 MWCO) (600 ml retentate/9 liters of permeate). From 1.1 g of hyper comb-branched polymer PEI wherein G=1, there was obtained 10.8 g (86%) of the title product. The $^{13}$C-NMR spectrum indicated more of the signal at 60.1 ppm than at 59.67 ppm.

Example R

Preparation of a Hyper Comb-Branched Polymer PEI Wherein $N_c$ is 20, $N_b$ is 10 and G is 3

The material was prepared as described before using an Amicon S1Y10 spiral wound ultrafiltration cartridge (10,000 MWCO) and filtration volumes as described before. From 1.1 g (25 mmol NH) of hyper comb-branched polymer PEI dendrimer wherein $N_c$ is 20, $N_b$ is 10 and G is 2 there was obtained 10.3 g (82%) of the hyper comb-branched polymer PEI dendrimer wherein $N_c$ is 20, $N_b$ is 10, and G is 3. The $^{13}$C-NMR spectrum of the material again indicated carbinol signals at 60.1 ppm and 57 ppm.

Example S

Preparation of a Hyper Comb-Branched Polymer PEI Wherein $N_c$ is 20, $N_b$ is 10 and G is 4

This material was prepared as described above using an Amicon S1Y10 spiral wound ultrafiltration cartridge with the volumes indicated above. From 1.1 g (25 mmol NH maximum) of hyper comb-branched polymer PEI dendrimer wherein $N_c$ is 20, $N_b$ is 10 and G is 3, there was obtained 10.1 g of the title compound (80% yield).

Example T

Preparation of a Hyper Comb-Branched Polymer PEI Wherein $N_c$ is 20, $N_b$ is 10 and G is 5

The material was prepared as described above utilizing 1.1 g (25.5 mmol NH) of hyper comb-branched polymer PEI wherein $N_c$ is 20, $N_b$ is 10 and G is 4, 47.5 g (40 mmol) of PEOX oligomer, and 25 g (8 equivalents of amine per NH) of diisopropylethylamine. Workup as before using an Amicon S1Y10 spiral wound cartridge (700 ml of retentate, and 9 liters of permeate) gave 18 g of the PEOX-hyper comb-branched polymer copolymer. Hydrolysis with 50% $H_2SO_4$ and treatment with excess NaOH gave a cake of material that floated on the caustic mixture with a lot of trapped NaOH and sodium sulfate salts. The cake was heated in 300 ml of deionized water to boiling and allowed to cool giving a white precipitate. This mixture was ultracentrifuged at 8000 rpm for 10 minutes and the resulting clear liquid was poured from the settled white solid. This white solid was mixed with toluene and dried by azeotropic distillation to give 7.0 g (56%) of the title compound.

Example U

Preparation of a Hyper Comb-Branched Polymer PEI Wherein $N_c$ is 20, $N_b$ is 20 and G is 0

A PEOX oligomer having a dp of 20 was prepared from MeOTs (7.5 g, 40 mmol) and ethyl oxazoline (80 g, 800 mmol) by refluxing under tank nitrogen using a Hg bubbler. The LPEI (0.5 g, 0.52 mmol, 10 mmol per NH) in hot toluene was added to the PEOX oligomer followed by diisopropylethylaimine (74 g, 574 mmol, 29 mmol per NH). This mixture was refluxed for 72 hours. The volatiles were removed and the resulting residue was dissolved in deionized water. This mixture was ultrafiltered using a S1Y3 cartridge. Workup as before gave 9.8 g of a PEI product (theory 9.1 g). The $^{13}$C-NMR spectrum of this material indicated a significant amount of a carbinol signal at 60.2 ppm.

Example V

Preparation of a Comb-Branched PEI Polymer Wherein $N_c$ is 20, $N_b$ is 20 and G is 0

In this experiment, two equivalents of PEOX oligomer per NH of the PEI and diisopropylethylamine (30 equivalents per NH of PEI) were refluxed for five days. A very large stir bar was used to get more efficient stirring of the mixture than was obtained in the above experiment. The mixture was stripped of volatiles and the resulting residue dissolved in deionized water. Ultrafiltration of this mixture using the S1Y3 spiral wound cartridge gave no separations as determined by SEC. The SEC plot indicated two peaks. Upon co-injection with authentic PEOX oligomer having a dp of 20, one of the peaks was enhanced. The ultrafiltration was then carried out on a S1Y10 (10,000 MWCO) spiral wound cartridge. The SEC plot of the retentate was identical to the S1Y3 cartridge retentate.

The ultrafiltration was switched to an Amicon flat stock stirred cell system using YM10 (10,000 MWCO) cartridge. After 1.5 liters of permeate only a small amount of the presumed PEOX oligomer having a dp of 20 had been ultrafiltered.

The material was then ultrafiltered with the flate stock stirred cell using a YM 30 membrane (30,000 MWCO) (100 ml, retentate; 2000 ml, permeate) to give a good separation by SEC. The retentate evaporated to 18 g (42%) of the PEOX-Comb-Branched PEI copolymer. This material hydrolyzed to 7.0 g (38%) of the Comb-Branched PEI. The $^{13}$C-NMR spectrum of the Comb-Branched PEI indicated only a minor amount (about 10%) of the carbinol signal at 60.1 ppm relative to the methyl terminate signal at 36.5 ppm.

Example W

Preparation of a Hyper Comb-Branched Polymer PEI Polymer Wherein $N_c$ is 20, $N_b$ is 20 and G is 1

This material was prepared with two equivalents of PEOX oligomer having a dp of 20 and refluxing with diisopropylethylamine for three days. The reaction parameters were to be held constant to permit a reasonable analysis of the chemistry. An analysis of the crude reaction mixture by SEC at 48 hours, 72 hours and 96 hours indicated a progressive increase in molecular weight. Ultrafiltration of the crude material in water with the Amicon flat stock stirred cell using a YM30 (30,000 MWCO) membrane as before (100 ml, retentate; 2000 ml permeate) gave a 74% yield of the PEOX-hyper comb-branched polymer PEI copolymer. Hydrolysis and treatment with NaOH, recrystallization from water, and azeotropic drying in toluene, gave a 68% yield of the title compound.

Example X

Preparation of a Comb-Branched PEI Polymer Wherein $N_c$ is 20, $N_b$ is 100 and G is 0

Further exploration of the PEOX chain length on the grafting efficiency was done. A PEOX having a dp of 100 was prepared (24 hrs at reflux) and refluxed 65 hour with PEI (1 equivalent PEOX per NH) with 11 equivalents of diisopropylethylamine per NH. The mixture was evaporated of volatiles, dissolved in deionized water and ultrafiltered with an S1Y30 (30,000 MWCO) cartridge. Hydrolysis of the retentate and workup gave a 31% yield of a white amorphous powder. Hydrolysis of the permeate gave a white crystalline material, LPEI having a dp of 100.

Example Y

Preparation of a Styrene Core Polymer

The styrene core polymer precursor was prepared by polymerization of 20 g (192 mmol) of styrene in benzene (20 ml), initiated by s-butyl lithium (4 mmol). After 4 hours, the reaction was terminated by addition of methanol (1 ml). Chloromethylation of the product polymer (10 g polystyrene, 60 ml chloromethyl methyl ether, and 1 ml stannic chloride in 500 ml of carbon tetrachloride for 48 hours) gave the chloromethylated core polymer.

Example Z

Preparation of a Comb-Branched Polystyrene Wherein G is 0

Living polystyrene oligomer was generated by initiation of 20 g of styrene by 4 mmol of s-butyl lithium, as in Example AA. After 4 hours at room temperature, 6 mmol of diphenylethylene in 350 ml of tetrahydrofuran was added. The chloromethylated polystyrene core was added portionwise, over 30 minutes, until most of the orange color of the carbanion had disappeared. After an additional 30 minutes, residual carbanions were terminated by the addition of 1 ml of methanol. Evaporation of the solvent and fractionation in toluene/methanol gave an 80% yield of the title compound.

Example AA

Preparation of a Hyper Comb-Branched Polymer Polystyrene Polymer Wherein G is Equal to 1

The product of Example Z was chloromethylated as described in Example Y. Grafting was carried out as described in Example Z, substituting the chloromethylated-comb-branched material for the linear-chloromethylated-polystyrene core.

Example BB

Preparation of a Hyper Comb-Branched Polymer Polystyrene Polymer Wherein G is 2

The product of Example AA was chloromethylated as described in Example Y. Grafting was carried out as described in Example Z, substituting the chloromethylated-comb-burst material for the linear-chloromethylated-polystyrene core.

Example CC

Preparation of Rod-Shaped Hyper Comb-Branched Polymer PEI Wherein $N_c$ is 200, $N_b$ is 5 and G is 3

This material was prepared as described above using N-morpholine terminated PEI as an initiator core. Repeated grafting (4 times) with methyl tosylate (3.7 g, 20 mmol) and ethyl oxazoline (10 g, 100 mmol) in 100 ml of toluene, followed by hydrolysis with 150 ml of 50% $H_2SO_4$ gave the dendrimers in a 70% to 80% yields. These products were characterized by $^{13}$C-NMR spectroscopy, titration and electrophoresis and shown to be the titled material.

Example DD

Preparation of Spherically-Shaped Hyper Comb-Branched Polymer PEI Wherein $N_c$ is 10, $N_b$ is 100 and G is 3

This material was prepared in the same manner as the rod-shaped dendrimer using LPEI (dp of 10) as an initiator core. The branches were constructed with PEOX (dp of 100), initiated as shown in the examples above.

Example EE

Synthesis of Ring Core Hyper Comb-Branched Polymers

AZACROWN™ (1,4,7,10-tetraazacyclododecane, cyclen) was obtained from The Dow Chemical Company, and was further recrystallized from toluene. The purified AZACROWN™ is a white needle-like crystal.

A mixture of methyl tosylate (MeOTs)(0.922 g, 4.95 mmol) in 100 ml of toluene was azeotroped to remove water with a distillation head under Ar for 10 minutes. After cooling to ~90° C., 2-ethyloxazoline (10 ml, 99.06 mmol) was cannulated in and the mixture was allowed to reflux for 5 hours. To this mixture was added AZACROWN™ core (0.214 g, 4.95 mmol of NH), which was dried by azeotropic distillation from toluene, followed by immediate addition of diisopropylethylamine (i-$Pr_2$NEt) (2–4 eq.). The mixture was refluxed for 1 hour, cooled, and then dissolved in methanol (~100% grafting yield as determined by SEC). After rotary-evaporation of the solvents, the crude product was either purified by ultrafiltration with Amicon spiral wound cartridges S1Y3 (3000 MWCO), or fractionated by methanol/diethyl ether mixture to remove the unreacted monomers, oligomers, and catalysts. The entire separation process was monitored by size exclusion chromatography (SEC). The purified product was rotary-evaporated and lyophilized to give a ring-branched polyethyloxazoline-polyethyleneimine (PEOX-PEI) polymer as a white powder. The higher generations of the ring core comb-burst polymers can be prepared in a similar manner as described in the linear core case as described above. All the products were analyzed by size exclusion chromatography (SEC), capillary electrophoresis (CE), nuclear magnetic resonance (NMR), and electrospray mass spectroscopy (ES-MS).

Example FF

Synthesis of Hyper-Terminally Branched Core Hyper Comb-Branched Polymers

A mixture of MeOTs (0.39 g, 1.98 mmol) in 100 ml of toluene was azeotroped to remove water with a distillation head under Ar for 10 minutes. After cooling to ~90° C., 2-ethyloxazoline (10 ml, 99.06 mmol) was cannulated in and the mixture was allowed to reflux for 5 hours. To this mixture was added a hyper-branched polyethylene amine core (0.214 g, 4.95 mmol of NH), which was dried by azeotropic distillation from toluene, followed by immediate addition of i-$Pr_2$NEt (large excess). The mixture was refluxed for 3 hours, cooled, and the top toluene solution was decanted off. The remaining viscous oil was redissolved in a small amount of MeOH and reprecipitated out in diethyl ether ($Et_2O$). After the top $Et_2O$ solution was decanted, the bottom precipitate was redissolved in methanol (MeOH) and dried over rotary evaporator and high vacuum to give a light yellow polyethyloxazoline-polyethyleneamine (PEOX-PEA) polymer. The higher generations of the hyper-branched core comb-burst polymers can be prepared in a similar manner as described in the linear core case described above. All the products were analyzed by SEC and NMR.

Instrumental for Examples EE and FF

SEC measurements were performed on a series of Beckman TSK 4000 PW (or POLY-OH, Polymer Laboratory), 3000 PW, and 2000 PW columns using Waters 510 HPLC pump, Thermo Separation Products AS 3000 Autosampler, Wyatt DAWN DSP-F Multi Angle Laser Light Scattering Detector, and Wyatt interferometer refractometer (Optilab 903). $^1$H and $^{13}$C-NMR spectra were obtained on Brucker 360 MHz or Varian Unity 300 MHz NMR spectrometer using either $CDCl_3$ or MeOD as solvents. Purity of monomers was checked by GC (HP 5890, He as carrier gas). Ultrafiltration was achieved using either an Amicon 3,000 or 10,000 molecular weight cutoff (MWCO) membrane. CE was performed on Beckman P/ACE System 2050 (Software System Gold). The polymer MWs were also measured by ES-MS (Finnigan Mat TSQ 700).

Example GG

Preparation of Poly (2-Ethyloxazoline) and Polyethyleneimine Linear Polymers (DP=10, 20, 50, 100, and 200)

Methyl p-toluenesulfonate, 2-ethyloxazoline, morpholine and diisopropylethylamine were purchased from Aldrich. Methyl p-toluenesulfonate was purified by distillation, while 2-ethyloxazoline, morpholine, diisopropylethylamine and toluene were stirred over $CaH_2$ and distilled prior to use. All the reactions were performed under an ultra pure Ar atmosphere.

The synthesis of poly(2-ethyloxazoline), (PEOX20, DP=20) is described to illustrate the general procedure for the preparation of linear PEOX. To a 250 ml two-neck round-bottom flask was added methyl p-toluenesulfonate (7.45 g, 40 mmol) and dry toluene (150 ml). A distillation head (vacuum type) was attached and trace amounts of water in the mixture were removed by azeotroping with toluene for 10–15 minutes. After cooling to about 90° C., ethyloxazoline (80.8 ml, 800 mmol) was cannulated in, and the mixture was allowed to reflux for 10 hours before termination with excess morpholine. During the polymerization, a cloudy PEOX suspension was formed. After the termination with morpholine, the solution became clear again. The crude mixture was rotary-evaporated and then hydrolyzed with 500 ml of 50% $H_2SO_4$, followed by azeotroping the water-propionic acid mixture with a Dean-Stark trap until the pH of the distillate was neutral. This hot acidic solution was slowly added (with a separatory funnel) into a 50% NaOH solution cooled by an ice bath. This solution (pH≧11) was heated to boil under $N_2$, and the product (linear PEI) floated on top as an oily layer. After cooling to room temperature, the top layer became a solid cake on the surface which was subsequently removed and redissolved in 600 ml deionized, boiling water. After slow sedimentation overnight, the white precipitate was filtered by suction funnel.

In order to completely remove excess NaOH, cold water was used to exhaustively wash the precipitate until pH of the filtrate solution was neutral. Pure polymer was obtained by azeotropic removal of water from a toluene solution of the polymer, followed by a gravity filtration and then rotary evaporating the toluene at 60° C. Such polymer was further dried under high vacuum overnight (33 g, 85.8% yield, MW=1,130, MWD=1.05). Linear PEOX and PEI 10, 50, 100, and 200 were prepared in a similar manner (PEOX yield ≧90%, PEI yield ≧80%). All the polymers were analyzed by SEC, ES-MS, NMR, CE, and PAGE.

Example HH

Synthesis of Comb-Branched Polymers (G0)

The synthesis of PEOX10-g-PEI20 is provided as a general procedure for the preparation of Comb-Branched PEOX-PEI and PEI polymers. A mixture of MeOTs (7.38 g, 39.62 mmol) in 150 ml of toluene was azeotroped to remove water with a distillation head under Ar for 10 minutes. After cooling to about 90° C., 2-ethyloxazoline (40 ml, 396.24 mmol) was cannulated in and the mixture was allowed to reflux for 5 hours. To this mixture was added morpholine terminated LPEI 20 (1.90 g, 39.62 mmol of NH), which was dried by azeotropic distillation from toluene, followed by immediate addition of i-Pr$_2$NEt (1 to 2 eq.). The mixture was refluxed for 1 hour, cooled, and then dissolved in methanol (about 75% grafting yield as determined by SEC). After rotary-evaporation of the solvents, the crude product was either purified by ultrafiltration with Amicon spiral wound cartridges S1Y3 (3,000 MWCO), or fractionated by methanol/diethyl ether mixture to remove the unreacted monomers, oligomers, and catalysts. The entire separation process was monitored by SEC. The purified product was rotary-evaporated and lyophilized to give a comb-branched PEOX-PEI polymers as a white powder. This white powder was further hydrolyzed in 50% H$_2$SO$_4$ at 100° C. and purified as described before to provide a PEI comb-branched polymer as a white viscous oil (MW=2,50 WD=1.22). Comb-branched PEOX20-g-PEI20, PEOX10-g-PEI50, PEOX50-g-PEI20, PEOX100-g-PEI50, PEOX200-g-PEI50, and PEOX20-g-1,4,7,10-Tetraazacylododecane) (PEOX20-g-AZACROWN™) were also prepared in a similar manner. All the products were analyzed by SEC-multi angle laser light scattering, CE, NMR, ES-MS and PAGE.

Example II

Synthesis of Comb-Branched Polymers (G1)

A mixture of MeOTs (0.738 g, 3.962 mmol) in 150 ml of toluene was azeotroped to dryness with a distillation head under Ar for 10 minutes. After cooling to about 90° C., 2-ethyloxazoline (40 ml, 396.24 mmol) was cannulated in and the mixture was allowed to reflux for 10 hours. To this mixture was added Comb-branched PEI (0.209 g, about 3.962 mmol of NH) dried by azeotropic distillation from toluene, followed by immediate addition of i-Pr$_2$NEt (1–2 eq.). The mixture was refluxed for 1 hour, and then cooled to room temperature. The top toluene solution was decanted off and the bottom polymer product was redissolved in methanol. This crude product was purified by refractionation with a methanol/diethyl ether mixture to remove the unreacted monomers, oligomers, and catalysts. The entire separation was monitored by SEC. The purified product was rotary-evaporated and lyophilized to give the Comb-branched PEOX-PEI polymer as a white powder (MW=260,000, MWD=1.10). The grafting yield depends on the length of the side chains (normally around 40%–80% as determined by SEC). Shorter side chains give a higher grafting yield. This white powder was further hydrolyzed in 50% H$_2$SO$_4$ at 100° C. and purified as described before to provide a PEI Comb-branched polymer as a white solid (80% yield, MW=138,800, MWD=1.34).

Example JJ

Synthesis of Comb-branched (G2)

A mixture of MeOTs (0.738 g, 3.962 mmol) in 150 ml of toluene was azeotroped to dryness with a distillation head under Ar for 10 minutes. After cooling to about 90° C., 2-ethyloxazoline (40 ml, 396.24 mmol) was cannulated in and the mixture was allowed to reflux for 10 hours. To this mixture was added Comb-branched PEI polymer (0.200 g, about 3.962 mmol of NH) dried by azeotropic distillation from toluene, followed by immediate addition of i-Pr$_2$NEt (1–2 eq.). The mixture was refluxed for 1 hour, and then cooled to room temperature. The top toluene solution was decanted off and the bottom polymer product was redissolved in methanol. This crude product was purified by refractionation with a methanol/diethyl ether mixture to remove the unreacted monomers, oligomers, and catalysts. The entire separation was monitored by SEC. The purified product was rotary-evaporated and lyophilized to give the Comb-branched PEOX-PEI polymer as a white powder (MW=2,182,000, MWD=1.50). This white powder was further hydrolyzed in 50% H$_2$SO$_4$ at 100° C. and purified as described before to provide PEI Comb-branched polymers as a white solid (85% yield, MW=1,078,000, MWD=1.47). All the products were analyzed by SEC, CE, NMR and PAGE, viscometry, TGA, and DSC.

Example KK

Synthesis of Comb-Branched (G3)

The G3 Comb-Branched polymer was synthesized in a similar manner as above. The molecular weight of the resulting product was 10,400,000 and the molecular weight distribution was 1.20. The higher generation Comb-Branched polymers and other Comb-Branched polymers with different shapes due to the different side chains and initiator cores used were prepared in a similar manner.

Instrumental For Examples GG–KK

SEC measurements were performed on a series of Beckman TSK 4000 PW (or POLY-OH, Polymer Laboratory), 3000 PW, and 2000 PW columns using Waters 510 HPLC pump, Thermo Separation Products AS 3000 Autosampler, Wyatt DAWN DSP-F Multi Angle Laser Light Scattering Detector, and Wyatt interferometer refractometer (Optilab 903). $^1$H and $^{13}$C-NMR spectra were obtained on Brucker 360 MHz or Varian Unity 300 MHz NMR spectrometer using either CDCl$_3$ or MeOD as solvents. Purity of monomers was checked by GC (HP 5890, He as carrier gas). Ultrafiltration was achieved using an Amicon 3,000, 10,000, or 100,000 molecular weight cutoff (MWCO) membrane. Thermal analysis was performed on DuPont Thermal Gravimetric Analyzer (Model 951) with TA Instrumental Software (2000 Series). CE was performed on Beckman P/ACE System 2050 (Software System Gold). The polymer MWs were also measured by ES-MS (Finnigan Mat TSQ 700). PAGE analysis was performed on Gradipore gradient microgel (5–40% T) with a BioRad 500/200 power supply. The viscosity measurements were achieved on a Cannon-Ubbelohde semi-micro viscometer.

Example LL

Release of Salicylic Acid from Hyper Comb-Breached Polymer

In these experiments, the interaction of salicylic acid with hyper comb-breached polymer was investigated. Since salicylic acid contains a carboxylic acid group and hyper comb-branched polymers contain secondary amines, the charge interaction between the two could slow down the transport of the acid across a dialysis membrane. This would demonstrate that hyper comb-branched polymers could be used as slow-release or drug delivery agents.

The experiments were carried out at room temperature, using equilibrium static dialysis cell methodology. The dialysis apparatus consisted of a Spectrum Spectra/Por MacroDialyzer (half cell volume of 10 mL; part no. 132 377), with a pre-soaked Spectra/Por 1 membrane disk (molecular weight cutoff-6-8000) separating the two half-cells.

Ten mL of a solution containing salicylic acid (1.0 mg/mL) and hyper comb-branched polymer (7.5 mg/mL; 50% PEOX and PEI comb, G 1.0, lot #9124193), and adjusted to pH 6.65 with HCl solution, was placed in the donor compartment of the dialysis cell. An equal volume of pure water, adjusted to pH 6.65, was placed in the receptor compartment. Transport of salicylic acid into the receptor compartment was monitored at various time intervals by removing a small aliquot from the receptor phase and assaying the concentration by absorption at 296 nm.

The control experiment was carried out with an identical procedure to that described above, except that the donor solution contained no hyper comb-branched polymer. The results are shown in FIG. 37. The hyper comb-branched polymer release data is represented by squares, while the control experiment data is represented by diamonds. Note that although the absorbance values are mostly greater than one, the aliquots were appropriately diluted (to bring the absorbance below one) before their absorbances were measured. The absorbance of the undiluted aliquot could then be calculated from the dilution factor.

It can be seen from FIG. 37 that the presence of hyper comb-branched polymer caused the salicylic acid to be released more slowly (i.e., the control had a steeper slope) and less total salicylic acid was transported within the time frame of the experiments (3 days). Also, there appears to be sustained release characteristics caused by the presence of hyper comb-branched polymer, since the levels of released salicylic acid continued to slowly rise after the approximate 12-hour equilibrium point seen in the control study. These experiments therefore demonstrate that hyper comb-branched polymer has the potential to be used as a slow-release or drug delivery agent.

Of course, it is understood that the foregoing are merely preferred embodiments of the invention and that various changes and alterations can be made without departing from the spirit and broader aspects thereof as set forth in the appended claims, which are to be interpreted in accordance with the principals of patent law including the Doctrine of Equivalents.

The embodiments of the invention in which an exclusive property or privilege is claimed are defined as follows:

1. A hyper comb-branched polymer conjugate of the formula:

wherein H is a hyper comb-branched polymer, said hyper comb-branched polymer including at least a core, a plurality of zero generation linear oligomeric branch chains grafted to the core, and a plurality of first generation linear oligomeric branch chains grafted to zero generation linear oligomeric branch chains;

M is a carried material;

v is an integer of at least 1; and b is an integer of at least 1.

2. The conjugate of claim 1 wherein M is selected from the group consisting of diagnostic agents, agricultural agents, bioactive agents, industrial agents, environmental agents, consumer product agents, and combinations thereof.

3. The conjugate of claim 2 wherein M is an agricultural agent selected from the group consisting of biological response modifiers, scavenging agents, agricultural materials, pheromones, pesticides, herbicides, genetic materials, and combinations thereof.

4. The conjugate of claim 2 wherein M is a bioactive agent selected from the group consisting of pharmaceutical agents, drugs, pharmaceutical intermediaries, radioprotective agents, toxins, antibodies, antibody fragments, hormones, biological response modifiers, scavenging agents, imunopotentiating agents, genetic materials, antigens, polypeptides, and combinations thereof.

5. A hyper comb-branched polymer conjugate comprising a hyper comb-branched polymer and a carried material, said hyper comb-branch polymer including at least a core, a plurality of zero generation linear oligomeric branch chains grafted to the core, and a plurality of first generation linear oligomeric branch chains grafted to zero generation linear oligomeric branch chains, wherein said hyper comb-branched polymer has a grafting density of from about 0.1% to about 90%.

6. A hyper comb-branched polymer conjugate comprising a hyper comb-branched polymer and a carried material, said hyper comb-branch polymer including at least a core, a plurality of zero generation linear oligomeric branch chains grafted to the core, and a plurality of first generation linear oligomeric branch chains grafted to zero generation linear oligomeric branch chains, wherein said hyper comb-branched polymer has an interior void volume of from about 10 angstroms to about 500 angstroms.

7. A hyper comb-branched polymer conjugate comprising a hyper comb-branched polymer and a carried material, said hyper comb-branch polymer including at least a core, a plurality of zero generation linear oligomeric branch chains grafted to the core, and a plurality of first generation linear oligomeric branch chains grafted to zero generation linear oligomeric branch chains wherein said hyper comb-branched polymer comprises alternating regions of (i) a first region having a grafting density of less than about 50%, and (ii) a second region having a grafting density of more than about 50%.

8. A hyper comb-branched polymer conjugate comprising a hyper comb-branched polymer and a carried material, said hyper comb-branch polymer including at least a core, a plurality of zero generation linear oligomeric branch chains grafted to the core, and a plurality of first generation linear oligomeric branch chains grafted to zero generation linear oligomeric branch chains, wherein said hyper comb-branch polymer has at least one chemical moiety disposed about the periphery of said polymer, said moiety selected from the group consisting of —NH$_2$, —COOH, —COOMe, —NH$_4$, —PEOX, —PEG, —PEO, and combinations thereof.

9. The conjugate of claim 1 wherein H has the formula:

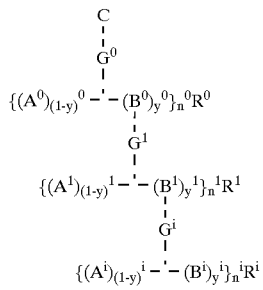

wherein

C is a core molecule; each R is the residual moiety of an initiator selected from a group consisting of free radical initiators, cationic initiators, anionic initiators, coordination polymerization initiators and group transfer initiators;

A and B are polymerizable monomers or comonomers capable of withstanding the conditions required for branching therefrom or grafting thereto, at least during the polymerization of the {(A)—(B)} linear polymer chain and during its grafting to a prior {(A)—(B)} branch or the {(A)—(B)} core branch;

each G is a grafting component, and the designation

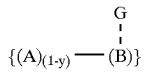

indicates that G can attach to either an (A) unit or a (B) unit;

n is the degree of polymerization of the indicated generation comb branches;

y is the fraction of B units in the indicated generation branch, and has a value of 0.01 to 1;

the superscripts 0, 1 and i designate the comb-branch generation level, with i beginning at "2" and continuing for the number of reiterative branch set generations in the polymer; and at least $n^\circ$ and $n'$ are $\geq 2$.

10. The conjugate of claim 9 wherein M is selected from the group consisting of diagnostic agents, agricultural agents, bioactive agents, industrial agents, environmental agents, consumer product agents, and combinations thereof.

11. The conjugate of claim 9 wherein said hyper comb-branched polymer has a hydrophobic exterior formed by grafting hydrophobic polymers selected from the group consisting of polyethylene, polydimethylsiloxane, polybutadiene, polystyrene, polymethylmethacrylate, perfluoropolymer, poly(2-alkyl or phenyl oxazolines), and combinations thereof, at the last grafting step.

12. The conjugate of claim 9 wherein said hyper comb-branched polymer has a hydrophilic exterior formed by grafting hydrophilic polymers selected from the group consisting of poly(2-ethyloxazoline), poly(2-methyloxazoline), polyethylene glycol, polyethylene oxide, polyacrylic acid, polyacrylic amide, polyvinyl pyrrolidone, and combinations thereof.

13. The conjugate of claim 9 wherein said hyper comb-branched polymer includes at least one molecule which has a molecular weight of from about 10,000 to about 100,000,000.

14. The conjugate of claim 13 wherein said hyper comb-branched polymer includes at least one molecule which has a molecular weight of from about 10,000 to about 10,000,000.

15. The conjugate of claim 9 wherein n has a value of from about 2 to about 10,000.

16. The conjugate of claim 9 wherein A is selected from the group consisting of $-CH_2CH_2-$, $-CH_2CH=CHCH_2-$, $-CH_2C(CH_3)_2-$, $-CH_2CH(CN)-$,

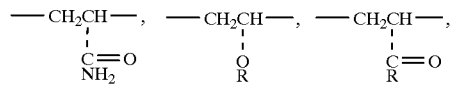

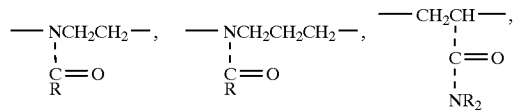

-continued

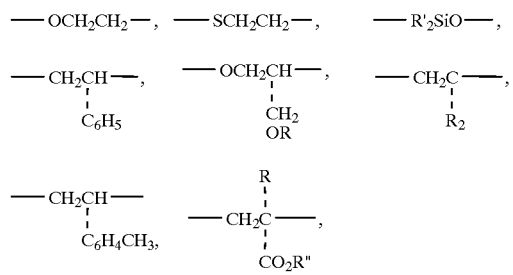

and combinations thereof, wherein R' is an alkyl group, aryls, arylalkyl, hydrogen, or carboalkoxy; R is an alkyl group, aryls, or hydrogen; and R" is an alkyl group.

17. The conjugate of claim 9 wherein B is selected from the group consisting of

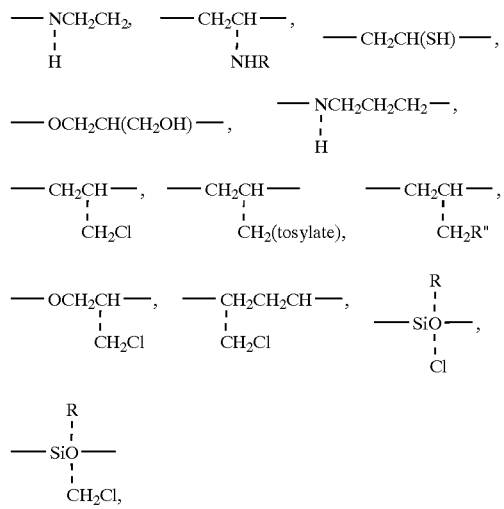

and combinations thereof, wherein R is an alkyl group, aryls, or hydrogen, and R" is an alkyl group.

18. The conjugate of claim 1 wherein said hyper comb-branched polymer has an outer periphery functionalized with ethylene diamine or chloroethylamine.

19. A hyper comb-branched polymer conjugate of the formula:

$$H_v—M_b—T_z$$

wherein H is a hyper comb-branched polymer, said hyper comb-branched polymer including at least a core, a plurality of zero generation linear oligomeric branch chains grafted to the core, and a plurality of first generation linear oligomeric branch chains grafted to zero generation linear oligomeric branch chains;

M is a carried material;

T is a target director;

v is an integer of at least 1;

b is an integer of at least 1; and z is an integer of at least 1.

20. The conjugate of claim 19 wherein M is selected from the group consisting of diagnostic agents, agricultural agents, bioactive agents, industrial agents, environmental agents, consumer product agents, and combinations thereof.

21. The conjugate of claim 20 wherein M is a diagnostic agent selected from the group consisting of metal ions, radioactive drugs, radioactive tracers, radio-opaques, radionuclides, signal generators, signal reflectors, signal absorbers, diagnostic opacifier agents, fluorescent moieties, dye moieties, and combinations thereof.

22. The conjugate of claim 20 wherein M is an agricultural agent selected from the group consisting of biological response modifiers, scavenging agents, agricultural materials, pheromones, pesticides, herbicides, genetic materials, and combinations thereof.

23. The conjugate of claim 20 wherein M is a bioactive agent selected from the group consisting of pharmaceutical agents, drugs, pharmaceutical intermediaries, radioprotective agents, toxins, antibodies, antibody fragments, hormones, biological response modifiers, scavenging agents, imuno-potentiating agents, genetic materials, antigens, polypeptides, and combinations thereof.

24. A hyper comb-branched polymer conjugate comprising a hyper comb-branched polymer and a carried material wherein said hyper comb-branched polymer has a maximum diameter of about 100 nm, said hyper comb-branch polymer including at least a core, a plurality of zero generation linear oligomeric branch chains grafted to the core, and a plurality of first generation linear oligomeric branch chains grafted to zero generation linear oligomeric branch chains.

25. A hyper comb-branched polymer conjugate comprising a hyper comb-branched polymer and a carried material, said hyper comb-branch polymer including at least a core, a plurality of zero generation linear oligomeric branch chains grafted to the core, and a plurality of first generation linear oligomeric branch chains grafted to zero generation linear oligomeric branch chains, wherein said hyper comb-branched polymer has a hydrophobically-modified region, said region being at least one of an interior region or an exterior region.

26. A hyper comb-branched polymer conjugate comprising a hyper comb-branched polymer and a carried material, said hyper comb-branch polymer including at least a core, a plurality of zero generation linear oligomeric branch chains grafted to the core, and a plurality of first generation linear oligomeric branch chains grafted to zero generation linear oligomeric branch chains, wherein said hyper comb-branched polymer has a hydrophilically-modified region, said region being at least one of an interior region or an exterior region.

27. The conjugate of claim 19 wherein H has the formula:

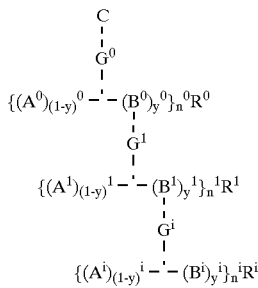

wherein
C is a core molecule; each R is the residual moiety of an initiator selected from a group consisting of free radical initiators, cationic initiators, anionic initiators, coordination polymerization initiators and group transfer initiators;
A and B are polymerizable monomers or comonomers capable of withstanding the conditions required for branching therefrom or grafting thereto, at least during the polymerization of the {(A)—(B)} linear polymer chain and during its grafting to a prior {(A)—(B)} branch or the {(A)—(B)} core branch; each G is a grafting component, and the designation

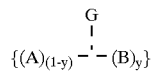

indicates that G can attach to either an (A) unit or a (B) unit;
n is the degree of polymerization of the indicated generation comb branches;
y is the fraction of B units in the indicated generation branch, and has a value of 0.01 to 1;
the superscripts 0, 1 and i designate the comb-branch generation level, with i beginning at "2" and continuing for the number of reiterative branch set generations in the polymer; and at least $n^0$ and $n^1$ are $\geq 2$.

28. The conjugate of claim 27 wherein M is selected from the group consisting of diagnostic agents, agricultural agents, bioactive agents, industrial agents, environmental agents, consumer product agents, and combinations thereof.

29. The conjugate of claim 27 wherein said hyper comb-branched polymer has a hydrophobic exterior formed by grafting hydrophobic polymers selected from the group consisting of polyethylene, polydimethylsiloxane, polybutadiene, polystyrene, polymethylmethacrylate, perfluoropolymer, poly(2-alkyl or phenyl oxazolines), and combinations thereof, at the last grafting step, wherein the alkyl group of said poly(2-alkyl oxazoline) has about 4 or more carbon atoms.

30. The conjugate of claim 27 wherein said hyper comb-branched polymer has a hydrophilic exterior formed by grafting hydrophilic polymers selected from the group consisting of poly(2-ethyloxazoline), poly(2-methyloxazoline), polyethylene glycol, polyethylene oxide, polyacrylic acid, polyacrylic amide, polyvinyl pyrrolidone, and combinations thereof.

31. The conjugate of claim 27 wherein said hyper comb-branched polymer includes at least one molecule which has a molecular weight of from about 10,000 to about 100,000,000.

32. The conjugate of claim 31 wherein said hyper comb-branched polymer includes at least one molecule which has a molecular weight of from about 10,000 to about 10,000,000.

33. The conjugate of claim 27 wherein n has a value of from about 2 to about 10,000.

34. The conjugate of claim 27 wherein A is selected from the group consisting of $-CH_2CH_2-$, $-CH_2CH=CHCH_2-$, $-CH_2C(CH_3)_2-$, $-CH_2CH(CN)-$,

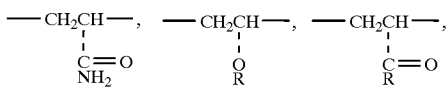

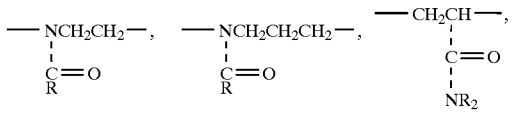

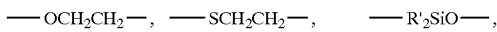

-continued

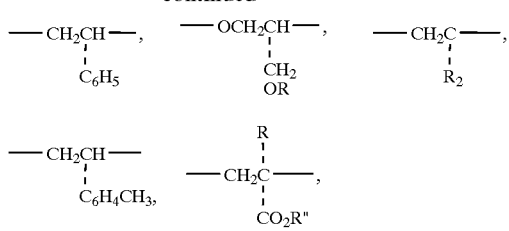

and combinations thereof, wherein R' is an alkyl group, aryls, arylalkyl, hydrogen, or carboalkoxy; R is an alkyl group, aryls, or hydrogen; and R" is an alkyl group.

35. The conjugate of claim 27 wherein B is selected from the group consisting of

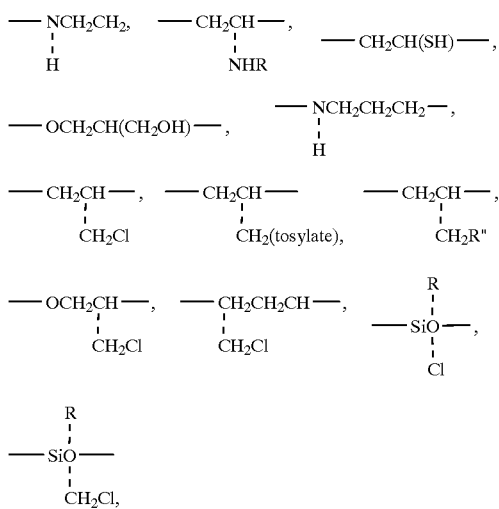

and combinations thereof, wherein R is an alkyl group, aryls, or hydrogen, and R" is an alkyl group.

36. The conjugate of claim 19 wherein T is selected from the group consisting of bioactive agents, proteins, antibodies, antibody fragments, saccharides, and oligosaccharides.

37. A hyper comb-branched polymer conjugate of the formula:

$$H_v\text{—}M_b\text{—}M'_a$$

wherein H is a hyper comb-branched polymer, said hyper comb-branched polymer including at least a core, a plurality of zero generation linear oligomeric branch chains grafted to the core, and a plurality of first generation linear oligomeric branch chains grafted to zero generation linear oligomeric branch chains;

M is a first carried material;

M' is a second carried material different than said first carried material;

v is an integer of at least 1;

b is an integer of at least 1; and a is an integer of at least 1.

38. The conjugate of claim 37 wherein one of M or M' is selected from the group consisting of diagnostic agents, agricultural agents, bioactive agents, industrial agents, environmental agents, consumer product agents, and combinations thereof.

39. The conjugate of claim 38 wherein one of M or M' is an agricultural agent selected from the group consisting of biological response modifiers, scavenging agents, agricultural materials, pheromones, pesticides, herbicides, genetic materials, and combinations thereof.

40. The conjugate of claim 38 wherein one of M or M' is a bioactive agent selected from the group consisting of pharmaceutical agents, drugs, pharmaceutical intermediaries, radioprotective agents, toxins, antibodies, antibody fragments, hormones, biological response modifiers, scavenging agents, imuno-potentiating agents, genetic materials, antigens, polypeptides, and combinations thereof.

41. The conjugate of claim 37 further comprising a target director T.

42. The conjugate of claim 41 wherein T is selected from the group consisting of bioactive agents, proteins, antibodies, antibody fragments, saccharides, and oligosaccharides.

43. A composition comprising a hyper comb-branched polymer conjugate of the formula:

$$H_v\text{—}M_b$$

wherein H is a hyper comb-branched polymer, said hyper comb-branched polymer including at least a core, a plurality of zero generation linear oligomeric branch chains grafted to the core, and a plurality of first generation linear oligomeric branch chains grafted to zero generation linear oligomeric branch chains;

M is a first carried material;

v is an integer of at least 1; and b is an integer of at least 1.

44. The composition of claim 43 wherein said hyper comb-branched polymer H has the general formula:

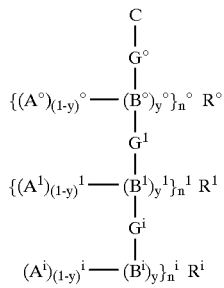

wherein

C is a core molecule;

each R is the residual moiety of an initiator selected from a group consisting of free radical initiators, cationic initiators, anionic initiators, coordination polymerization initiators and group transfer initiators;

A and B are polymerizable monomers or comonomers capable of withstanding the conditions required for branching therefrom or grafting thereto, at least during the polymerization of the {(A)—(B)} linear polymer chain and during its grafting to a prior {(A)—(B)} branch or the {(A)—(B)} core branch;

each G is a grafting component, and the designation

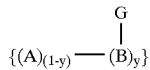

indicates that G can attach to either an (A) unit or a (B) unit;

n is the degree of polymerization of the indicated generation comb branches;

y is the fraction of B units in the indicated generation branch, and has a value of 0.01 to 1;

the superscripts 0, 1 and i designate the comb-branch generation level, with i beginning at "2" and continuing for the number of reiterative branch set generations in the polymer; and at least $n^\circ$ and n' are $\geq 2$.

45. The composition of claim 44 wherein M is selected from the group consisting of diagnostic agents, agricultural agents, bioactive agents, industrial agents, environmental agents, consumer product agents, and combinations thereof.

46. The composition of claim 44 wherein said hyper comb-branched polymer includes at least one molecule which has a molecular weight of from abut 10,000 to about 100,000,000.

47. The conjugate of claim 37 wherein H has the formula:

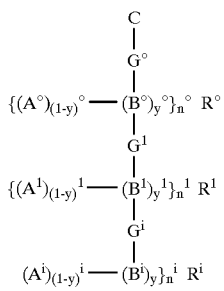

wherein

C is a core molecule;

each R is the residual moiety of an initiator selected from a group consisting of free radical initiators, cationic initiators, anionic initiators, coordination polymerization initiators and group transfer initiators;

A and B are polymerizable monomers or comonomers capable of withstanding the conditions required for branching therefrom or grafting thereto, at least during the polymerization of the {(A)—(B)} linear polymer chain and during its grafting to a prior {(A)—(B)} branch or the {(A)—(B)} core branch;

each G is a grafting component, and the designation

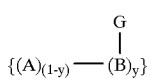

indicates that G can attach to either an (A) unit or a (B) unit;

n is the degree of polymerization of the indicated generation comb branches;

y is the fraction of B units in the indicated generation branch, and has a value of 0.01 to 1;

the superscripts 0, 1 and i designate the comb-branch generation level, with i beginning at "2" and continuing for the number of reiterative branch set generations in the polymer; and at least $n^\circ$ and $n^1$ are $\geq 2$.

48. The conjugate of claim 47 wherein one of M or M' is selected from the group consisting of diagnostic agents, agricultural agents, bioactive agents, industrial agents, environmental agents, consumer product agents, and combinations thereof.

49. The conjugate of claim 47 wherein said hyper comb-branched polymer has hydrophobic exterior formed by grafting hydrophobic polymers selected from the group consisting of polyethylene, polydimethylsiloxane, polybutadiene, polystyrene, polymethylmethacrylate, perfluoropolymer, poly(2-alkyl or phenyl oxazolines), and combinations thereof.

50. The conjugate of claim 47 wherein said hyper comb-branched polymer has a hydrophilic exterior formed by grafting hydrophilic polymers selected from the group consisting of poly(2-ethyloxazoline), poly(2-methyloxazoline), polyethylene glycol, polyethylene oxide, polyacrylic acid, polyacrylic amide, polyvinyl pyrrolidone, and combinations thereof.

51. The conjugate of claim 47 wherein said hyper comb-branched polymer includes at least one molecule which has a molecular weight of from abut 10,000 to about 100,000, 000.

52. The conjugate of claim 51 wherein said hyper comb-branched polymer includes at least one molecule which has a molecular weight of from about 10,000 to about 10,000, 000.

53. The conjugate of claim 47 wherein n has a value of from about 2 to about 10,000.

54. The conjugate of claim 47 wherein A is selected from the group consisting of $-CH_2CH_2-$, $-CH_2CH=CHCH_2-$, $-CH_2C(CH_3)_2-$, $-CH_2CH(CN)-$,

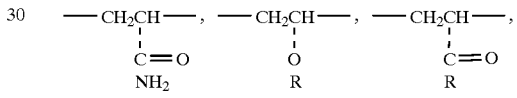

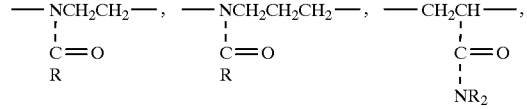

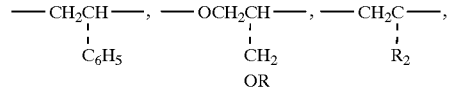

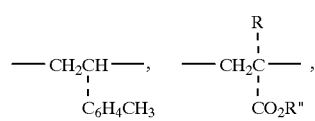

and combinations thereof, wherein R' is an alkyl group, aryls, arylalkyl, hydrogen, or carboalkoxy; R is an alkyl group, aryls or hydrogen; and R" is an alkyl group.

55. The conjugate of claim 47 wherein B is selected from the group consisting of

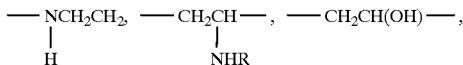

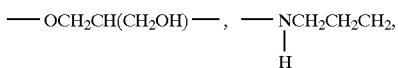

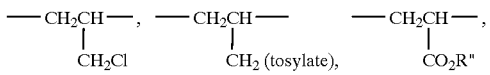

57

-continued

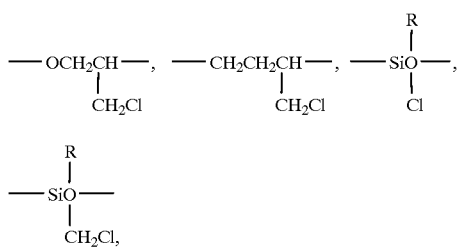

and combinations thereof, wherein R is an alkyl group, aryls, or hydrogen, and R" is an alkyl group.

56. The composition of claim 44 wherein said hyper comb-branched polymer includes at least one molecule which has a molecular weight of from about 10,000 to about 10,000,000.

57. A method of carrying genetic material, said method comprising:

providing a hyper comb-branched polymer having a plurality of positively charged sites, said hyper comb-branched polymer including at least a core, a plurality of zero generation linear oligomeric branch chains grafted to the core, and a plurality of first generation linear oligomeric branch chains grafted to zero generation linear oligomeric branch chains; and conjugating said polymer with genetic material having a plurality of negatively charged sites.

58. The method of claim 57 wherein the ratio of said negatively charged sites to said positively charged sites ranges from about 1:10 to about 1:1000.

59. The method claim 57 wherein said hyper comb-branched polymer is modified with a moiety selected from the group consisting of —NH$_2$, —NH—, poly(ethyloxazoline), chloroethylamine, and combinations thereof.

60. The conjugate product of claim 57.

61. A process for preparing a complex of hyper comb-branched polymer and genetic material comprising:

reacting said hyper comb-branched polymer with said genetic material in a solvent at a temperature which facilitates the complexing of said genetic material with said hyper comb-branched polymer, said hyper comb-branched polymer including at least a core, a plurality of zero generation linear oligomeric branch chains grafted to the core, and a plurality of first generation linear oligomeric branch chains grafted to the zero generation linear oligomeric branch chains.

62. The process of claim 61 which includes attaching a target director to said hyper comb-branched polymer before complexing it with genetic material.

63. The process of claim 62 wherein said target director is selected from the group consisting of bioactive agents, proteins, antibodies, antibody fragments, saccharides, and oligosaccharides.

64. The process of clam 62 wherein said hyper comb-branched polymer has a predominantly cationic surface, said process comprising electrostatically attaching genetic material to said polymer to create said complex.

65. A process for forming a genetic material: hyper comb-branched polymer complex comprising:

mixing, in water, sufficient genetic material to yield a final concentration from about 1 to about 10 μg per mL, with sufficient hyper comb-branched polymer, having positive surface functionality, to yield a genetic material:

58 polymer charge ratio from about 1:10 to about 1:10,000, said hyper comb-branched polymer including at least a core, a plurality of zero generation linear oligomeric branch chains grafted to the core, and a plurality of first generation linear oligomeric branch chains grafted to zero generation linear oligomeric branch chains;

said mixing being done at a pH of about 5 to about 10 and at a temperature from about 20 to about 40° C.

66. The process of claim 65 wherein said charge ratio is from about 1:10 to about 1:1,000.

67. The process of claim 65 wherein said charge ratio is from about 1:100 to about 1:1000.

68. The process of claim 65 wherein said charge ratio is about 1:200.

69. The process of claim 65 wherein said hyper comb-branched polymer comprises amino acids over a portion of its surface.

70. A composition comprising a hyper comb-branched polymer conjugate of the formula:

$$H_v\text{---}M_b\text{---}T_z$$

wherein H is a hyper comb-branched polymer, said hyper comb-branched polymer including at least a core, a plurality of zero generation linear oligomeric branch chains grafted to the core, and a plurality of first generation linear oligomeric branch chains grafted to zero generation linear oligomeric branch chains;

M is a carried material;

T is a target director;

v is an integer of at least 1;

b is an integer of at least 1; and z is an integer of at least 1.

71. The composition of claim 70 wherein said hyper comb-branched polymer H has the general formula:

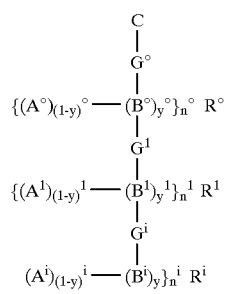

wherein

C is a core molecule;

each R is the residual moiety of an initiator selected from a group consisting of free radical initiators, cationic initiators, anionic initiators, coordination polymerization initiators and group transfer initiators;

A and B are polymerizable monomers or comonomers capable of withstanding the conditions required for branching therefrom or grafting thereto, at least during the polymerization of the {(A)—(B)} linear polymer chain and during its grafting to a prior {(A)—(B)} branch or the {(A)—(B)} core branch;

each G is a grafting component, and the designation

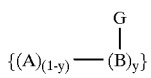

indicates that G can attach to either an (A) unit or a (B) unit;

n is the degree of polymerization of the indicated generation comb branches;

y is the fraction of B units in the indicated generation branch, and has a value of 0.01 to 1;

the superscripts 0, 1 and i designate the comb-branch generation level, with i beginning at "2" and continuing for the number of reiterative branch set generations in the polymer; and at least $n°$ and $n^1$ are $\geq 2$.

72. The composition of claim 71 wherein M is selected from the group consisting of diagnostic agents, agricultural agents, bioactive agents, industrial agents, environmental agents, consumer product agents, and combinations thereof.

73. The composition of claim 71 wherein said hyper comb-branched polymer includes at least one molecule which has a molecular weight of from abut 10,000 to about 100,000,000.

74. The composition of claim 71 wherein said hyper comb-branched polymer includes at least one molecule which has a molecular weight of from about 10,000 to about 10,000,000.

75. The conjugate of claim 70 wherein T is selected from the group consisting of bioactive agents, proteins, antibodies, antibody fragments, saccharides, and oligosaccharides.

76. A composition comprising a hyper comb-branched polymer conjugate of the formula:

$$H_v—M_b—M'_a$$

wherein H is a hyper comb-branched polymer, said hyper comb-branched polymer including at least a core, a plurality of zero generation linear oligomeric branch chains grafted to the core, and a plurality of first generation linear oligomeric branch chains grafted to zero generation linear oligomeric branch chains;

M is a first carried material;

M' is a second carried material different than said first carried material;

v is an integer of at least 1;

b is an integer of at least 1; and a is an integer of at least 1.

77. The composition of claim 76 wherein said hyper comb-branched polymer H has the general formula:

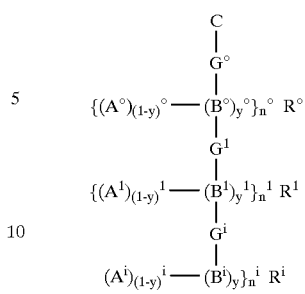

wherein

C is a core molecule;

each R is the residual moiety of an initiator selected from a group consisting of free radical initiators, cationic initiators, anionic initiators, coordination polymerization initiators and group transfer initiators;

A and B are polymerizable monomers or comonomers capable of withstanding the conditions required for branching therefrom or grafting thereto, at least during the polymerization of the {(A)—(B)} linear polymer chain and during its grafting to a prior {(A)—(B)} branch or the {(A)—(B)} core branch;

each G is a grafting component, and the designation

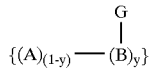

indicates that G can attach to either an (A) unit or a (B) unit;

n is the degree of polymerization of the indicated generation comb branches;

y is the fraction of B units in the indicated generation branch, and has a value of 0.01 to 1;

the superscripts 0, 1 and i designate the comb-branch generation level, with i beginning at "2" and continuing for the number of reiterative branch set generations in the polymer; and at least $n°$ and $n^1$ are $\geq 2$.

78. The composition of claim 77 wherein M or M' is selected from the group consisting of diagnostic agents, agricultural agents, bioactive agents, industrial agents, environmental agents, consumer product agents, and combinations thereof.

79. The composition of claim 77 wherein said hyper comb-branched polymer includes at least one molecule which has a molecular weight of from abut 10,000 to about 100,000,000.

80. The composition of claim 76 wherein said hyper comb-branched polymer includes at least one molecule which has a molecular weight of from about 10,000 to about 10,000,000.

81. The composition of claim 76 wherein said conjugate further comprises a target director T.

82. The composition of claim 81 wherein T is selected from the group consisting of bioactive agents, proteins, antibodies, antibody fragments, saccharides, and oligosaccharides.

83. The process of claim 69 wherein said amino acid is lysine or arginine.

84. The process of claim 65 wherein said polymer particles include target director moieties attached thereto.

85. A process for forming a concentrated genetic material: hyper comb-branched polymer complex which can be diluted for use comprising:

mixing, in water, sufficient genetic material to yield a concentration from about 1 to about 10 µg per 20 µL, with sufficient hyper comb-branched polymer, having positive surface functionality, to yield a genetic material: polymer charge ratio from about 1:10 to about 1:10,000, said hyper comb-branched polymer including at least a core, a plurality of zero generation linear oligomeric branch chains grafted to the core, and a plurality of first generation linear oligomeric branch chains grafted to zero generation linear oligomeric branch chains;

said mixing being done at a pH from about 5 to about 10 and at a temperature from about 20 to about 40° C.

86. The process of claim 85 wherein said charge ratio is from about 1:10 to about 1:1,000.

87. The process of claim 85 wherein said charge ratio is from about 1:100 to about 1:1000.

88. The process of claim 85 wherein said charge ratio is about 1:200.

89. A method of effecting cell transfection and bioavailability of genetic material comprising providing a complex of a hyper comb-branched polymer and genetic material, and making said complex available to cells to be transfected, said hyper comb-branch polymer including at least a core, a plurality of zero generation linear oligomeric branch chains grafted to the core, and a plurality of first generation linear oligomeric branch chains grafted to zero generation linear oligomeric branch chains.

90. A method for transporting genetic material through a cellular membrane and into a cellular nucleus comprising:

complexing said genetic material with hyper comb-branched polymer, said hyper comb-branch polymer including at least a core, a plurality of zero generation linear oligomeric branch chains grafted to the core, and a plurality of first generation linear oligomeric branch chains grafted to zero generation linear oligomeric branch chains;

followed by making said complex available to cells to be transfected.

91. A method for protecting genetic material from digestion during transit to and transfection into a cell comprising:

complexing said genetic material with hyper comb-branched polymer prior to exposing said genetic material to digestive enzymes, said hyper comb-branch polymer including at least a core, a plurality of zero generation linear oligomeric branch chains grafted to the core, and a plurality of first generation linear oligomeric branch chains grafted to zero generation linear oligomeric branch chains.

92. A method for stabilizing and compacting genetic material comprising complexing said genetic material with hyper comb-branched polymer, said hyper comb-branch polymer including at least a core, a plurality of zero generation linear oligomeric branch chains grafted to the core, and a plurality of first generation linear oligomeric branch chains grafted to zero generation linear oligomeric branch chains.

* * * * *